(12) United States Patent
Wakasa et al.

(10) Patent No.: US 6,388,174 B1
(45) Date of Patent: May 14, 2002

(54) GENE ENCODING α-SUBUNIT OF RICE ANTHRANILATE SYNTHASE AND DNA RELATING THERETO

(75) Inventors: Kyo Wakasa, Machida; Yuzuru Tozawa, Tsukuba; Teruhiko Terakawa; Hisakazu Hasegawa, both of Atsugi, all of (JP)

(73) Assignees: Hokko Chemical Industry Co., Ltd., Tokyo; National Agricultural Research Organization (NARO), Ibaraki, both of (JP)

( * ) Notice: Subject to any disclaimer, the term of this patent is extended or adjusted under 35 U.S.C. 154(b) by 0 days.

(21) Appl. No.: 09/486,382

(22) PCT Filed: Aug. 31, 1998

(86) PCT No.: PCT/JP98/03883

§ 371 Date: Apr. 25, 2000

§ 102(e) Date: Apr. 25, 2000

(87) PCT Pub. No.: WO99/11800

PCT Pub. Date: Mar. 11, 1999

(30) Foreign Application Priority Data

Aug. 29, 1997 (JP) .............................................. 9-235049

(51) Int. Cl.[7] .......................... C12N 15/79; C12N 5/14; C12N 1/21; C12N 15/29; C12N 15/82

(52) U.S. Cl. .................... 800/300; 800/278; 435/320.1; 435/252.33; 435/418; 536/23.6

(58) Field of Search .............................. 536/23.2, 23.6; 435/468, 418, 320.1, 71.1, 252.33; 800/278, 300

(56) References Cited

U.S. PATENT DOCUMENTS 6,118,047 A * 9/2000 Anderson et al.

* cited by examiner

*Primary Examiner*—Amy J. Nelson
*Assistant Examiner*—David H Kruse
(74) *Attorney, Agent, or Firm*—Larson & Taylor PLC

(57) ABSTRACT

A DNA sequence is provided, which encodes an enzyme that is the α-subunit of the first isozyme of rice anthranilate synthase (ASA). Transformed plants having a high tryptophan content can be regenerated by culturing the plant cells having introduced therein such a recombinant vector which contains, at a position downstream of a promoter, an inserted DNA fragment carrying the above DNA sequence. In addition, methods of selecting transformed plant cells are disclosed, wherein plant cells transformed with the discloses DNA are resistant to inhibitory concentrations of tryptophan or tryptophan analogues.

10 Claims, 3 Drawing Sheets

SEQUENCE LISTING

<160> NUMBER OF SEQ ID NOS: 19

<210> SEQ ID NO 1
<211> LENGTH: 1734
<212> TYPE: DNA
<213> ORGANISM: Oryza sativa
<220> FEATURE:
<221> NAME/KEY: CDS
<222> LOCATION: (1)..(1734)

<400> SEQUENCE: 1

```
atg gcc agc ctc gtg ctc tcc ctg cgc atc g cc cgt tcc acg ccg ccg        48
Met Ala Ser Leu Val Leu Ser Leu Arg Ile A la Arg Ser Thr Pro Pro
  1               5                  10                  15 ctg ggg ctg ggc ggg ggg cga ttc cgc ggc c ga cga ggg gcc gtc gcc        96
Leu Gly Leu Gly Gly Gly Arg Phe Arg Gly A rg Arg Gly Ala Val Ala
             20                  25                  30 tgc cgc gcc gcc acg ttc cag cag ctc gac g cc gtc gcg gtg agg gag       144
Cys Arg Ala Ala Thr Phe Gln Gln Leu Asp A la Val Ala Val Arg Glu
         35                  40                  45 gag gag tcc aag ttc aag gcg ggg gcg gcg g ag ggt tgc aac atc ctg       192
Glu Glu Ser Lys Phe Lys Ala Gly Ala Ala G lu Gly Cys Asn Ile Leu
     50                  55                  60 ccg ctc aag cga tgc atc ttc tcc gac cac c tc acg ccg gtg ctc gcg       240
Pro Leu Lys Arg Cys Ile Phe Ser Asp His L eu Thr Pro Val Leu Ala
 65                  70                  75                  80 tac cgc tgc ctc gtc agg gag gac gac cgc g ag gcg ccc agc ttc ctg       288
Tyr Arg Cys Leu Val Arg Glu Asp Asp Arg G lu Ala Pro Ser Phe Leu
                 85                  90                  95
```

```
ttt gag tcc gtc gag cag gga tcc gag ggc a cc aat gtg ggg agg tac        336
Phe Glu Ser Val Glu Gln Gly Ser Glu Gly T hr Asn Val Gly Arg Tyr
                100                 105                 110 agt gtg gtt ggg gca cag cct gcg atg gag a tc gta gcc aag gcc aac        384
Ser Val Val Gly Ala Gln Pro Ala Met Glu I le Val Ala Lys Ala Asn
            115                 120                 125 cat gtg act gtc atg gat cat aag atg aag t ct agg agg gag caa ttt        432
His Val Thr Val Met Asp His Lys Met Lys S er Arg Arg Glu Gln Phe
        130                 135                 140 gcg cct gac ccg atg aag ata cca agg agc a tt atg gaa cag tgg aac        480
Ala Pro Asp Pro Met Lys Ile Pro Arg Ser I le Met Glu Gln Trp Asn
145                 150                 155                 160 cca cag att gtt gaa ggc ctc cct cat gca t tt tgt gga gga tgg gtt        528
Pro Gln Ile Val Glu Gly Leu Pro His Ala P he Cys Gly Gly Trp Val
                165                 170                 175 gga ttc ttc tct tac gac aca gtg cgt tat g tt gaa aca aag aag ctt        576
Gly Phe Phe Ser Tyr Asp Thr Val Arg Tyr V al Glu Thr Lys Lys Leu
            180                 185                 190 cca ttt tct aac gcg cca gag gat gat agg a ac ctt cct gac atc cat        624
Pro Phe Ser Asn Ala Pro Glu Asp Asp Arg A sn Leu Pro Asp Ile His
        195                 200                 205 tta ggc ctc tac aat gac ata gtt gtg ttt g at cat gtt gaa aag aaa        672
Leu Gly Leu Tyr Asn Asp Ile Val Val Phe A sp His Val Glu Lys Lys
    210                 215                 220 aca cat gtt ata cat tgg gtg agg gta gat t gc cat gag tca gtt gac        720
Thr His Val Ile His Trp Val Arg Val Asp C ys His Glu Ser Val Asp
225                 230                 235                 240 gaa gcg tat gag gac ggg aag aat cag ctg g aa gct ttg tta tca aga        768
Glu Ala Tyr Glu Asp Gly Lys Asn Gln Leu G lu Ala Leu Leu Ser Arg
                245                 250                 255 tta cat agt gtt aat gtg cca act ctt act g ct ggt tct gta aaa ctt        816
Leu His Ser Val Asn Val Pro Thr Leu Thr A la Gly Ser Val Lys Leu
            260                 265                 270 aac gtt ggg caa ttt ggg tca gca cta cag a aa tca tca atg tca agg        864
Asn Val Gly Gln Phe Gly Ser Ala Leu Gln L ys Ser Ser Met Ser Arg
        275                 280                 285 gag gac tat aag aaa gct gtt gtt caa gca a aa gag cac att cta gct        912
Glu Asp Tyr Lys Lys Ala Val Val Gln Ala L ys Glu His Ile Leu Ala
    290                 295                 300 ggt gac att ttt caa gta gtc tta agc cag c gt ttt gag agg cgt aca        960
Gly Asp Ile Phe Gln Val Val Leu Ser Gln A rg Phe Glu Arg Arg Thr
305                 310                 315                 320 ttt gct gac ccc ttt gag gtg tac cgt gca t tg cgt att gtc aat cct       1008
Phe Ala Asp Pro Phe Glu Val Tyr Arg Ala L eu Arg Ile Val Asn Pro
                325                 330                 335 agt cct tat atg gcc tat cta cag gct cgt g gt tgt att ctg gta gca       1056
Ser Pro Tyr Met Ala Tyr Leu Gln Ala Arg G ly Cys Ile Leu Val Ala
            340                 345                 350 tca agt cct gaa att ctt acc cgg gtg gaa a ag agg aca att gtc aac       1104
Ser Ser Pro Glu Ile Leu Thr Arg Val Glu L ys Arg Thr Ile Val Asn
        355                 360                 365 agg cca ctt gct gga aca att aga aga gga a aa tcg aaa gca gaa gac       1152
Arg Pro Leu Ala Gly Thr Ile Arg Arg Gly L ys Ser Lys Ala Glu Asp
    370                 375                 380 aaa gtt tta gaa caa ctg ctg ttg agt gat g ga aag cag tgt gct gag       1200
Lys Val Leu Glu Gln Leu Leu Leu Ser Asp G ly Lys Gln Cys Ala Glu
385                 390                 395                 400 cat att atg tta gta gat ctt gga cgg aat g at gtt gga aag gtg tcc       1248
His Ile Met Leu Val Asp Leu Gly Arg Asn A sp Val Gly Lys Val Ser
```

```
                    405                 410                 415
aaa cca ggt tca gta aag gtg gag aaa ctg a tg aac gtt gaa cga tat    1296
Lys Pro Gly Ser Val Lys Val Glu Lys Leu M et Asn Val Glu Arg Tyr
            420                 425                 430 tca cat gtc atg cac att agc tca aca gtt a ct gga gag ttg cgt gat    1344
Ser His Val Met His Ile Ser Ser Thr Val T hr Gly Glu Leu Arg Asp
                435                 440                 445 gat ctg act tgt tgg gat gct ctt cga gca g ca ttg ccc gtt gga aca    1392
Asp Leu Thr Cys Trp Asp Ala Leu Arg Ala A la Leu Pro Val Gly Thr
        450                 455                 460 gtt agt ggt gca cca aag gtg aga gcg atg g ag ctg att gac cag atg    1440
Val Ser Gly Ala Pro Lys Val Arg Ala Met G lu Leu Ile Asp Gln Met
465                 470                 475                 480 gaa ggg aag atg cgt ggg ccg tac agt ggt g gc ttt gga ggg gtt tct    1488
Glu Gly Lys Met Arg Gly Pro Tyr Ser Gly G ly Phe Gly Gly Val Ser
                485                 490                 495 ttc cgt gga gac atg gac atc gca ctt gct c tc cgt acc atc gtc ttc    1536
Phe Arg Gly Asp Met Asp Ile Ala Leu Ala L eu Arg Thr Ile Val Phe
            500                 505                 510 ccc acg gga tct cgc ttc gac acc atg tac t cc tac act gac aag aat    1584
Pro Thr Gly Ser Arg Phe Asp Thr Met Tyr S er Tyr Thr Asp Lys Asn
        515                 520                 525 gct cgt cag gag tgg gtg gct cac ctt cag g ct gga gct ggg atc gtc    1632
Ala Arg Gln Glu Trp Val Ala His Leu Gln A la Gly Ala Gly Ile Val
530                 535                 540 gct gac agc aag cct gac gat gag cat cag g ag tgc ttg aac aag gct    1680
Ala Asp Ser Lys Pro Asp Asp Glu His Gln G lu Cys Leu Asn Lys Ala
                545                 550                 555                 560 gct ggc ctt gct cgt gcc atc gat ctt gcc g ag tct aca ttc gta gat    1728
Ala Gly Leu Ala Arg Ala Ile Asp Leu Ala G lu Ser Thr Phe Val Asp
            565                 570                 575 gag tag                                                              1734
Glu

<210> SEQ ID NO 2
<211> LENGTH: 577
<212> TYPE: PRT
<213> ORGANISM: Oryza sativa

<400> SEQUENCE: 2

Met Ala Ser Leu Val Leu Ser Leu Arg Ile A la Arg Ser Thr Pro Pro
  1               5                  10                  15

Leu Gly Leu Gly Gly Arg Phe Arg Gly A rg Arg Gly Ala Val Ala
             20                  25                  30

Cys Arg Ala Ala Thr Phe Gln Gln Leu Asp A la Val Ala Val Arg Glu
         35                  40                  45

Glu Glu Ser Lys Phe Lys Ala Gly Ala G lu Gly Cys Asn Ile Leu
     50                  55                  60

Pro Leu Lys Arg Cys Ile Phe Ser Asp His L eu Thr Pro Val Leu Ala
 65                  70                  75                  80

Tyr Arg Cys Leu Val Arg Glu Asp Asp Arg G lu Ala Pro Ser Phe Leu
                 85                  90                  95

Phe Glu Ser Val Glu Gln Gly Ser Glu Gly T hr Asn Val Gly Arg Tyr
            100                 105                 110

Ser Val Val Gly Ala Gln Pro Ala Met Glu I le Val Ala Lys Ala Asn
        115                 120                 125

His Val Thr Val Met Asp His Lys Met Lys S er Arg Arg Glu Gln Phe
    130                 135                 140
```

```
Ala Pro Asp Pro Met Lys Ile Pro Arg Ser Ile Met Glu Gln Trp Asn
145                 150                 155                 160

Pro Gln Ile Val Glu Gly Leu Pro His Ala Phe Cys Gly Gly Trp Val
            165                 170                 175

Gly Phe Ser Tyr Asp Thr Val Arg Tyr Val Glu Thr Lys Lys Leu
        180                 185                 190

Pro Phe Ser Asn Ala Pro Glu Asp Asp Arg Asn Leu Pro Asp Ile His
        195                 200                 205

Leu Gly Leu Tyr Asn Asp Ile Val Val Phe Asp His Val Glu Lys Lys
    210                 215                 220

Thr His Val Ile His Trp Val Arg Val Asp Cys His Glu Ser Val Asp
225                 230                 235                 240

Glu Ala Tyr Glu Asp Gly Lys Asn Gln Leu Glu Ala Leu Leu Ser Arg
            245                 250                 255

Leu His Ser Val Asn Val Pro Thr Leu Thr Ala Gly Ser Val Lys Leu
            260                 265                 270

Asn Val Gly Gln Phe Gly Ser Ala Leu Gln Lys Ser Ser Met Ser Arg
        275                 280                 285

Glu Asp Tyr Lys Lys Ala Val Val Gln Ala Lys Glu His Ile Leu Ala
290                 295                 300

Gly Asp Ile Phe Gln Val Val Leu Ser Gln Arg Phe Glu Arg Arg Thr
305                 310                 315                 320

Phe Ala Asp Pro Phe Glu Val Tyr Arg Ala Leu Arg Ile Val Asn Pro
            325                 330                 335

Ser Pro Tyr Met Ala Tyr Leu Gln Ala Arg Gly Cys Ile Leu Val Ala
            340                 345                 350

Ser Ser Pro Glu Ile Leu Thr Arg Val Glu Lys Arg Thr Ile Val Asn
        355                 360                 365

Arg Pro Leu Ala Gly Thr Ile Arg Arg Gly Lys Ser Lys Ala Glu Asp
        370                 375                 380

Lys Val Leu Glu Gln Leu Leu Leu Ser Asp Gly Lys Gln Cys Ala Glu
385                 390                 395                 400

His Ile Met Leu Val Asp Leu Gly Arg Asn Asp Val Gly Lys Val Ser
            405                 410                 415

Lys Pro Gly Ser Val Lys Val Glu Lys Leu Met Asn Val Glu Arg Tyr
        420                 425                 430

Ser His Val Met His Ile Ser Ser Thr Val Thr Gly Glu Leu Arg Asp
    435                 440                 445

Asp Leu Thr Cys Trp Asp Ala Leu Arg Ala Ala Leu Pro Val Gly Thr
    450                 455                 460

Val Ser Gly Ala Pro Lys Val Arg Ala Met Glu Leu Ile Asp Gln Met
465                 470                 475                 480

Glu Gly Lys Met Arg Gly Pro Tyr Ser Gly Phe Gly Gly Val Ser
            485                 490                 495

Phe Arg Gly Asp Met Asp Ile Ala Leu Ala Leu Arg Thr Ile Val Phe
        500                 505                 510

Pro Thr Gly Ser Arg Phe Asp Thr Met Tyr Ser Tyr Thr Asp Lys Asn
        515                 520                 525

Ala Arg Gln Glu Trp Val Ala His Leu Gln Ala Gly Ala Gly Ile Val
    530                 535                 540

Ala Asp Ser Lys Pro Asp Asp Glu His Gln Glu Cys Leu Asn Lys Ala
545                 550                 555                 560
```

```
Ala Gly Leu Ala Arg Ala Ile Asp Leu Ala G lu Ser Thr Phe Val Asp
            565                 570                 575
Glu

<210> SEQ ID NO 3
<211> LENGTH: 1498
<212> TYPE: DNA
<213> ORGANISM: Oryza sativa
<220> FEATURE:
<221> NAME/KEY: promoter
<222> LOCATION: (1)..(1101)
<221> NAME/KEY: CDS
<222> LOCATION: (1102)..(1233)
<223> OTHER INFORMATION: exon 1
<221> NAME/KEY: intron
<222> LOCATION: (1234)..(1318)
<221> NAME/KEY: CDS
<222> LOCATION: (1319)..(1498)
<223> OTHER INFORMATION: Partial sequence of ex on 2

<400> SEQUENCE: 3
```

| | |
|---|---|
| gaattcaaat tttttatata gagtatttct atacatgaat ttttctaact t tttgttttt | 60 |
| taaaaaaaat ttgtgtggtg tactgtaata ggaagagaag aaggggagga g gaaggaggg | 120 |
| agaagaggga ggagtatatg gggaggggggg gatgaactga tcgcccagcg t gatagctgg | 180 |
| cgatcgagca cccattagaa gggcccaata aaccctggaa aattgtcatt g agtggcacc | 240 |
| tttcattgag aagacgttat taggaattgt agaagtggaa aattatgcta t ctgttgtat | 300 |
| tgagtgtcac tgtcaccgat aaagctttgc tggttaatgc attgtatttc t ccatcaacg | 360 |
| cttcatgata caatggtatt tggacgtgtt tataaaataa tatacgtata a tgtgggtgg | 420 |
| cctagcggcg gccggttaca catagcagcg atcggtccga tgctagtctt c attcattca | 480 |
| ggtatgtatt caggtatcag tgtgtgggtg atagttttttt tttttcgttt t tctagttac | 540 |
| gatatctcat atctcatagt tgtgatctta taaacttttt catgtttatc a atataaatt | 600 |
| tcgtgttatc tagtcgttaa aagaaccgta taatgtggca aaaaaaatgt a taatgtgtc | 660 |
| agagtttgca cgtgtttatc ttgctgcccc gaaacgatta attcagtgat t tggcaacaa | 720 |
| caaaatgtcg tggcggataa gcatatccgt cccaaaagga aaaaaagaaa a ggaaaaata | 780 |
| atctttagaa ataaagccct tactttttcc aagaagcaga ggtaaccgta g ctggtattc | 840 |
| cgcggctaac tcaatcccctt tctctggagt cttggagcgg cacggcggct g cgcacccga | 900 |
| cctcgcccac cacctgctcg gcgaaacgcc cggctcggcc gcgacgtgtc c caccgcacc | 960 |
| gcgcgcgcac ccgcgcgccc cgagcccctc gccgcctccg cgcgggcgcc g cacctatt | 1020 |
| aaatgcggcc ccgatcccgc attctctcaa ctgcactagt ccccaccaac g gctcggtcc | 1080 |

| | |
|---|---|
| agtagagttt atcccccacc t atg gcc agc ctc gtg ctc tcc ctg cgc atc | 1131 |
|   Met Ala Ser Leu Val Leu Ser Leu Arg Ile | |
|   1               5                   10 | |
| gcc cgt tcc acg ccg ccg ctg ggg ctg ggc g gg ggg cga ttc cgc ggc | 1179 |
| Ala Arg Ser Thr Pro Pro Leu Gly Leu Gly G ly Gly Arg Phe Arg Gly | |
|         15                  20                  25 | |
| cga cga ggg gcc gtc gcc tgc cgc gcc gcc a cg ttc cag cag ctc gac | 1227 |
| Arg Arg Gly Ala Val Ala Cys Arg Ala Ala T hr Phe Gln Gln Leu Asp | |
|     30                  35                  40 | |
| gcc gtc ggtgagtctc cgtatcaaat gtgggggggc atgtcttggt t gcggattg | 1283 |
| Ala Val | |
| gtgggttgat ttgaatgtgt gttctcgtgg ccgca gcg gtg agg gag gag gag | 1336 |
|                                      Ala Val Arg Glu Glu Glu | |
|                                         45               50 | |

```
tcc aag ttc aag gcg ggg gcg gcg gag ggt t gc aac atc ctg ccg ctc    1384
Ser Lys Phe Lys Ala Gly Ala Ala Glu Gly C ys Asn Ile Leu Pro Leu
                55                  60                  65 aag cga tgc atc ttc tcc gac cac ctc acg c cg gtg ctc gcg tac cgc    1432
Lys Arg Cys Ile Phe Ser Asp His Leu Thr P ro Val Leu Ala Tyr Arg
                70                  75                  80 tgc ctc gtc agg gag gac gac cgc gag gcg c cc agc ttc ctg ttt gag    1480
Cys Leu Val Arg Glu Asp Asp Arg Glu Ala P ro Ser Phe Leu Phe Glu
            85                  90                  95 tcc gtc gag cag gga tcc                                              1498
Ser Val Glu Gln Gly Ser
        100
```

<210> SEQ ID NO 4
<211> LENGTH: 104
<212> TYPE: PRT
<213> ORGANISM: Oryza sativa

<400> SEQUENCE: 4

```
Met Ala Ser Leu Val Leu Ser Leu Arg Ile A la Arg Ser Thr Pro Pro
 1               5                  10                  15

Leu Gly Leu Gly Gly Gly Arg Phe Arg Gly A rg Arg Gly Ala Val Ala
                20                  25                  30

Cys Arg Ala Ala Thr Phe Gln Gln Leu Asp A la Val Ala Val Arg Glu
            35                  40                  45

Glu Glu Ser Lys Phe Lys Ala Gly Ala Ala G lu Gly Cys Asn Ile Leu
        50                  55                  60

Pro Leu Lys Arg Cys Ile Phe Ser Asp His L eu Thr Pro Val Leu Ala
 65                  70                  75                  80

Tyr Arg Cys Leu Val Arg Glu Asp Asp Arg G lu Ala Pro Ser Phe Leu
                85                  90                  95

Phe Glu Ser Val Glu Gln Gly Ser
                100
```

<210> SEQ ID NO 5
<211> LENGTH: 44
<212> TYPE: PRT
<213> ORGANISM: Oryza sativa

<400> SEQUENCE: 5

```
Met Ala Ser Leu Val Leu Ser Leu Arg Ile A la Arg Ser Thr Pro Pro
 1               5                  10                  15

Leu Gly Leu Gly Gly Gly Arg Phe Arg Gly A rg Arg Gly Ala Val Ala
                20                  25                  30

Cys Arg Ala Ala Thr Phe Gln Gln Leu Asp A la Val
            35                  40
```

<210> SEQ ID NO 6
<211> LENGTH: 60
<212> TYPE: PRT
<213> ORGANISM: Oryza sativa

<400> SEQUENCE: 6

```
Ala Val Arg Glu Glu Glu Ser Lys Phe Lys A la Gly Ala Ala Glu Gly
 1               5                  10                  15

Cys Asn Ile Leu Pro Leu Lys Arg Cys Ile P he Ser Asp His Leu Thr
                20                  25                  30

Pro Val Leu Ala Tyr Arg Cys Leu Val Arg G lu Asp Asp Arg Glu Ala
            35                  40                  45
```

```
Pro Ser Phe Leu Phe Glu Ser Val Glu Gln Gly Ser
    50                  55                  60
```

<210> SEQ ID NO 7
<211> LENGTH: 1101
<212> TYPE: DNA
<213> ORGANISM: Oryza sativa
<220> FEATURE:
<221> NAME/KEY: promoter
<222> LOCATION: (1)..(1101)

<400> SEQUENCE: 7

```
gaattcaaat ttttatata gagtatttct atacatgaat ttttctaact t tttgttttt       60
taaaaaaaat ttgtgtggtg tactgtaata ggaagagaag aagggagga g gaaggaggg     120
agaagaggga ggagtatatg gggagggggg gatgaactga tcgcccagcg t gatagctgg    180
cgatcgagca cccattagaa gggcccaata aaccctggat aattgtcatt g agtggcacc    240
tttcattgag aagacgttat taggaattgt agaagtggat aattatgcta t ctgttgtat   300
tgagtgtcac tgtcaccgat aaagctttgc tggttaatgc attgtatttc t ccatcaacg   360
cttcatgata caatggtatt tggacgtgtt tataaaataa tatacgtata a tgtgggtgg   420
cctagcggcg gccggttaca catagcagcg atcggtccga tgctagtctt c attcattca   480
ggtatgtatt caggtatcag tgtgtgggtg atagtttttt tttttcgttt t tctagttac   540
gatatctcat atctcatagt tgtgatctta taaactttt catgtttatc a atataaatt    600
tcgtgttatc tagtcgttaa aagaaccgta taatgtggca aaaaaaatgt a taatgtgtc   660
agagtttgca cgtgtttatc ttgctgcccc gaaacgatta attcagtgat t tggcaacaa   720
caaaatgtcg tggcggataa gcatatccgt cccaaaagga aaaaagaaa a ggaaaaata   780
atctttagaa ataaagccct tacttttttcc aagaagcaga ggtaaccgta g ctggtattc   840
cgcggctaac tcaatccctt tctctggagt cttggagcgg cacggcggct g cgcacccga   900
cctcgcccac cacctgctcg gcgaaacgcc cggctcggcc gcgacgtgtc c caccgcacc   960
gcgcgcgcac ccgcgcgccc cgagcccctc gccgcctccg cgcgggcgcc g cacctattt  1020
aaatgcggcc ccgatcccgc attctctcaa ctgcactagt ccccaccaac g gctcggtcc  1080
agtagagttt atcccccacc t                                              1101
```

<210> SEQ ID NO 8
<211> LENGTH: 21
<212> TYPE: DNA
<213> ORGANISM: Artificial Sequence
<220> FEATURE:
<223> OTHER INFORMATION: Designed base sequence based on known sequence
    of alpha-subunit gene (asa1, EMBL#M92353) of
    Arabidopsis thaliana anthranilate synt hase to act
    a primer

<400> SEQUENCE: 8

```
catatgtctt cctctatgaa c                                                21
```

<210> SEQ ID NO 9
<211> LENGTH: 24
<212> TYPE: DNA
<213> ORGANISM: Artificial Sequence
<220> FEATURE:
<223> OTHER INFORMATION: Designed base sequence based on known sequence
    of alpha-subunit gene (asa1, EMBL#M92353) of
    Arabidopsis thaliana anthranilate synt hase to act
    as a primer

<400> SEQUENCE: 9

```
ggatcctcat tttttcacaa atgc                                              24

<210> SEQ ID NO 10
<211> LENGTH: 1821
<212> TYPE: DNA
<213> ORGANISM: Oryza sativa
<220> FEATURE:
<221> NAME/KEY: CDS
<222> LOCATION: (1)..(1821)

<400> SEQUENCE: 10 atg gag tcc atc gcc gcc gcc acg ttc acg c cc tcg cgc ctc gcc gcc       48
Met Glu Ser Ile Ala Ala Ala Thr Phe Thr P ro Ser Arg Leu Ala Ala
 1               5                  10                  15 cgc ccc gcc act ccg gcg gcg gcg gcg gcc c cg gtt aga gcg agg gcg       96
Arg Pro Ala Thr Pro Ala Ala Ala Ala Ala P ro Val Arg Ala Arg Ala
             20                  25                  30 gcg gta gcg gca gga ggg agg agg agg acg a gt agg cgc ggc ggc gtg      144
Ala Val Ala Ala Gly Gly Arg Arg Arg Thr S er Arg Arg Gly Gly Val
         35                  40                  45 agg tgc tcc gcg ggg aag cca gag gca agc g cg gtg atc aac ggg agc      192
Arg Cys Ser Ala Gly Lys Pro Glu Ala Ser A la Val Ile Asn Gly Ser
 50                  55                  60 gcg gcg gcg cgg gcg gcg gag gag gac agg a gg cgc ttc ttc gag gcg      240
Ala Ala Ala Arg Ala Ala Glu Glu Asp Arg A rg Arg Phe Phe Glu Ala
 65                  70                  75                  80 gcg gag cgt ggg agc ggg aag ggc aac ctg g tg ccc atg tgg gag tgc      288
Ala Glu Arg Gly Ser Gly Lys Gly Asn Leu V al Pro Met Trp Glu Cys
             85                  90                  95 atc gtc tcc gac cac ctc acc ccc gtg ctc g cc tac cgc tgc ctc gtc      336
Ile Val Ser Asp His Leu Thr Pro Val Leu A la Tyr Arg Cys Leu Val
            100                 105                 110 ccc gag gac aac atg gag acg ccc agc ttc c tc ttc gag tcc gtc gag      384
Pro Glu Asp Asn Met Glu Thr Pro Ser Phe L eu Phe Glu Ser Val Glu
        115                 120                 125 cag ggg ccc gag ggc acc acc aac gtc ggt c gc tat agc atg gtg gga      432
Gln Gly Pro Glu Gly Thr Thr Asn Val Gly A rg Tyr Ser Met Val Gly
    130                 135                 140 gcc cac cca gtg atg gag gtc gtg gca aag g ag cac aag gtc aca atc      480
Ala His Pro Val Met Glu Val Val Ala Lys G lu His Lys Val Thr Ile
145                 150                 155                 160 atg gac cac gag aag ggc aag gtg acg gag c ag gtc gtg gat gat cct      528
Met Asp His Glu Lys Gly Lys Val Thr Glu G ln Val Val Asp Asp Pro
                165                 170                 175 atg cag atc ccc agg agc atg atg gaa gga t gg cac ccg cag cag atc      576
Met Gln Ile Pro Arg Ser Met Met Glu Gly T rp His Pro Gln Gln Ile
            180                 185                 190 gat cag ctc ccc gat tcc ttc acc ggt gga t gg gtc ggg ttc ttt tcc      624
Asp Gln Leu Pro Asp Ser Phe Thr Gly Gly T rp Val Gly Phe Phe Ser
        195                 200                 205 tat gat aca gtc cgt tat gtt gaa aag aag a ag ctg ccc ttc tcc ggt      672
Tyr Asp Thr Val Arg Tyr Val Glu Lys Lys L ys Leu Pro Phe Ser Gly
    210                 215                 220 gct ccc cag gac gat agg aac ctt cct gat g tt cac ctt ggg ctt tat      720
Ala Pro Gln Asp Asp Arg Asn Leu Pro Asp V al His Leu Gly Leu Tyr
225                 230                 235                 240 gat gat gtt ctc gtc ttc gac aat gtc gag a ag aaa gta tat gtc atc      768
Asp Asp Val Leu Val Phe Asp Asn Val Glu L ys Lys Val Tyr Val Ile
                245                 250                 255 cat tgg gta aat ctt gat cgg cat gca acc a cc gag gat gca ttc caa      816
```

```
                His Trp Val Asn Leu Asp Arg His Ala Thr T hr Glu Asp Ala Phe Gln
                                260                 265                 270 gat ggc aag tcc cgg ctg aac ctg ttg cta t ct aaa gtg cac aat tca          864
Asp Gly Lys Ser Arg Leu Asn Leu Leu Leu S er Lys Val His Asn Ser
            275                 280                 285 aat gta ccc aag ctt tct cca gga ttt gta a ag tta cac act cgg cag          912
Asn Val Pro Lys Leu Ser Pro Gly Phe Val L ys Leu His Thr Arg Gln
        290                 295                 300 ttt ggt aca cct ttg aac aaa tca acc atg a ca agt gat gag tac aag          960
Phe Gly Thr Pro Leu Asn Lys Ser Thr Met T hr Ser Asp Glu Tyr Lys
305                 310                 315                 320 aat gct gtt atg cag gct aag gag cat att a tg gct ggt gat att ttc         1008
Asn Ala Val Met Gln Ala Lys Glu His Ile M et Ala Gly Asp Ile Phe
                325                 330                 335 cag att gtt tta agc cag agg ttt gag agg c ga aca tac gcc aat cca         1056
Gln Ile Val Leu Ser Gln Arg Phe Glu Arg A rg Thr Tyr Ala Asn Pro
            340                 345                 350 ttt gaa gtc tat cga gct tta cga att gtg a ac cca agt cca tac atg         1104
Phe Glu Val Tyr Arg Ala Leu Arg Ile Val A sn Pro Ser Pro Tyr Met
        355                 360                 365 gca tat gta cag gca aga ggc tgt gtc ctg g ta gca tct agt cca gaa         1152
Ala Tyr Val Gln Ala Arg Gly Cys Val Leu V al Ala Ser Ser Pro Glu
370                 375                 380 att ctt act cgt gtg agg aag ggt aaa att a tt aac cgt cca ctt gct         1200
Ile Leu Thr Arg Val Arg Lys Gly Lys Ile I le Asn Arg Pro Leu Ala
385                 390                 395                 400 ggg act gtt cga agg ggc aag aca gag aag g aa gat gaa atg caa gag         1248
Gly Thr Val Arg Arg Gly Lys Thr Glu Lys G lu Asp Glu Met Gln Glu
                405                 410                 415 caa caa cta cta agt gat gaa aaa cag tgt g ct gaa cat att atg ctt         1296
Gln Gln Leu Leu Ser Asp Glu Lys Gln Cys A la Glu His Ile Met Leu
            420                 425                 430 gta gat ttg gga agg aat gat gtt gga aag g tc tcc aaa cct gga tct         1344
Val Asp Leu Gly Arg Asn Asp Val Gly Lys V al Ser Lys Pro Gly Ser
        435                 440                 445 gtg aag gtg gag aaa tta atg aac att gaa c gc tac tcc cat gtc atg         1392
Val Lys Val Glu Lys Leu Met Asn Ile Glu A rg Tyr Ser His Val Met
450                 455                 460 cac atc agt tcc acg gtg agt gga gag ttg g at gat cat ctc caa agt         1440
His Ile Ser Ser Thr Val Ser Gly Glu Leu A sp Asp His Leu Gln Ser
465                 470                 475                 480 tgg gat gcc ctg cga gcc gcg ttg cct gtt g ga aca gtt agt gga gca         1488
Trp Asp Ala Leu Arg Ala Ala Leu Pro Val G ly Thr Val Ser Gly Ala
                485                 490                 495 cca aag gtg aaa gcc atg gag ctg ata gac g ag cta gag gtc aca aga         1536
Pro Lys Val Lys Ala Met Glu Leu Ile Asp G lu Leu Glu Val Thr Arg
            500                 505                 510 cga gga cca tac agt ggc ggc ctt gga ggg a ta tca ttt gac ggg gac         1584
Arg Gly Pro Tyr Ser Gly Gly Leu Gly Gly I le Ser Phe Asp Gly Asp
        515                 520                 525 atg ctt atc gct ctt gca ctc cgc acc att g tg ttc tca aca gcc cca         1632
Met Leu Ile Ala Leu Ala Leu Arg Thr Ile V al Phe Ser Thr Ala Pro
530                 535                 540 agc cac aac acg atg tac tca tac aaa gac a cc gag agg cgc cgg gag         1680
Ser His Asn Thr Met Tyr Ser Tyr Lys Asp T hr Glu Arg Arg Arg Glu
545                 550                 555                 560 tgg gtc gct cac ctt cag gct ggt gct ggc a tt gtc gct gat agc agc         1728
Trp Val Ala His Leu Gln Ala Gly Ala Gly I le Val Ala Asp Ser Ser
                565                 570                 575
```

```
cca gac gac gag caa cgt gaa tgc gag aac aag gca gcc gct ctg gct    1776
Pro Asp Asp Glu Gln Arg Glu Cys Glu Asn Lys Ala Ala Ala Leu Ala
        580                 585                 590 cga gcc atc gat ctt gct gaa tca gct ttc gta gac aag gaa tag        1821
Arg Ala Ile Asp Leu Ala Glu Ser Ala Phe Val Asp Lys Glu
        595                 600                 605
```

<210> SEQ ID NO 11
<211> LENGTH: 606
<212> TYPE: PRT
<213> ORGANISM: Oryza sativa

<400> SEQUENCE: 11

```
Met Glu Ser Ile Ala Ala Ala Thr Phe Thr Pro Ser Arg Leu Ala Ala
 1               5                  10                  15

Arg Pro Ala Thr Pro Ala Ala Ala Ala Pro Val Arg Ala Arg Ala
            20                  25                  30

Ala Val Ala Ala Gly Gly Arg Arg Thr Ser Arg Arg Gly Gly Val
         35                  40                  45

Arg Cys Ser Ala Gly Lys Pro Glu Ala Ser Ala Val Ile Asn Gly Ser
     50                  55                  60

Ala Ala Arg Ala Ala Glu Glu Asp Arg Arg Arg Phe Phe Glu Ala
 65              70                  75                  80

Ala Glu Arg Gly Ser Gly Lys Gly Asn Leu Val Pro Met Trp Glu Cys
             85                  90                  95

Ile Val Ser Asp His Leu Thr Pro Val Leu Ala Tyr Arg Cys Leu Val
                100                 105                 110

Pro Glu Asp Asn Met Glu Thr Pro Ser Phe Leu Phe Glu Ser Val Glu
            115                 120                 125

Gln Gly Pro Glu Gly Thr Thr Asn Val Gly Arg Tyr Ser Met Val Gly
        130                 135                 140

Ala His Pro Val Met Glu Val Val Ala Lys Glu His Lys Val Thr Ile
145                 150                 155                 160

Met Asp His Glu Lys Gly Lys Val Thr Glu Gln Val Val Asp Asp Pro
                165                 170                 175

Met Gln Ile Pro Arg Ser Met Met Glu Gly Trp His Pro Gln Gln Ile
            180                 185                 190

Asp Gln Leu Pro Asp Ser Phe Thr Gly Gly Trp Val Gly Phe Phe Ser
        195                 200                 205

Tyr Asp Thr Val Arg Tyr Val Glu Lys Lys Lys Leu Pro Phe Ser Gly
    210                 215                 220

Ala Pro Gln Asp Asp Arg Asn Leu Pro Asp Val His Leu Gly Leu Tyr
225                 230                 235                 240

Asp Asp Val Leu Val Phe Asp Asn Val Glu Lys Lys Val Tyr Val Ile
                245                 250                 255

His Trp Val Asn Leu Asp Arg His Ala Thr Thr Glu Asp Ala Phe Gln
            260                 265                 270

Asp Gly Lys Ser Arg Leu Asn Leu Leu Ser Lys Val His Asn Ser
        275                 280                 285

Asn Val Pro Lys Leu Ser Pro Gly Phe Val Lys Leu His Thr Arg Gln
    290                 295                 300

Phe Gly Thr Pro Leu Asn Lys Ser Thr Met Thr Ser Asp Glu Tyr Lys
305                 310                 315                 320

Asn Ala Val Met Gln Ala Lys Glu His Ile Met Ala Gly Asp Ile Phe
                325                 330                 335
```

-continued

```
Gln Ile Val Leu Ser Gln Arg Phe Glu Arg Arg Thr Tyr Ala Asn Pro
        340                 345                 350

Phe Glu Val Tyr Arg Ala Leu Arg Ile Val Asn Pro Ser Pro Tyr Met
        355                 360                 365

Ala Tyr Val Gln Ala Arg Gly Cys Val Leu Val Ala Ser Ser Pro Glu
        370                 375                 380

Ile Leu Thr Arg Val Arg Lys Gly Lys Ile Ile Asn Arg Pro Leu Ala
385                 390                 395                 400

Gly Thr Val Arg Arg Gly Lys Thr Glu Lys Glu Asp Glu Met Gln Glu
                405                 410                 415

Gln Gln Leu Leu Ser Asp Glu Lys Gln Cys Ala Glu His Ile Met Leu
        420                 425                 430

Val Asp Leu Gly Arg Asn Asp Val Gly Lys Val Ser Lys Pro Gly Ser
        435                 440                 445

Val Lys Val Glu Lys Leu Met Asn Ile Glu Arg Tyr Ser His Val Met
450                 455                 460

His Ile Ser Ser Thr Val Ser Gly Glu Leu Asp Asp His Leu Gln Ser
465                 470                 475                 480

Trp Asp Ala Leu Arg Ala Ala Leu Pro Val Gly Thr Val Ser Gly Ala
                485                 490                 495

Pro Lys Val Lys Ala Met Glu Leu Ile Asp Glu Leu Glu Val Thr Arg
        500                 505                 510

Arg Gly Pro Tyr Ser Gly Gly Leu Gly Gly Ile Ser Phe Asp Gly Asp
        515                 520                 525

Met Leu Ile Ala Leu Ala Leu Arg Thr Ile Val Phe Ser Thr Ala Pro
        530                 535                 540

Ser His Asn Thr Met Tyr Ser Tyr Lys Asp Thr Glu Arg Arg Arg Glu
545                 550                 555                 560

Trp Val Ala His Leu Gln Ala Gly Ala Gly Ile Val Ala Asp Ser Ser
                565                 570                 575

Pro Asp Asp Glu Gln Arg Glu Cys Glu Asn Lys Ala Ala Ala Leu Ala
        580                 585                 590

Arg Ala Ile Asp Leu Ala Glu Ser Ala Phe Val Asp Lys Glu
        595                 600                 605

<210> SEQ ID NO 12
<211> LENGTH: 1734
<212> TYPE: DNA
<213> ORGANISM: Artificial Sequence
<220> FEATURE:
<223> OTHER INFORMATION: Modified DNA sequence of Sequence No.1
<221> NAME/KEY: CDS
<222> LOCATION: (1)..(1734)

<400> SEQUENCE: 12 atg gcc agc ctc gtg ctc tcc ctg cgc atc gcc cgt tcc acg ccg ccg      48
Met Ala Ser Leu Val Leu Ser Leu Arg Ile Ala Arg Ser Thr Pro Pro
1               5                   10                  15 ctg ggg ctg ggc ggg ggg cga ttc cgc ggc cga cga ggg gcc gtc gcc      96
Leu Gly Leu Gly Gly Gly Arg Phe Arg Gly Arg Arg Gly Ala Val Ala
            20                  25                  30 tgc cgc gcc gcc acg ttc cag cag ctc gac gcc gtc gcg gtg agg gag     144
Cys Arg Ala Ala Thr Phe Gln Gln Leu Asp Ala Val Ala Val Arg Glu
        35                  40                  45 gag gag tcc aag ttc aag gcg ggg gcg gcg gag ggt tgc aac atc ctg     192
Glu Glu Ser Lys Phe Lys Ala Gly Ala Ala Glu Gly Cys Asn Ile Leu
    50                  55                  60
```

| | |
|---|---|
| ccg ctc aag cga tgc atc ttc tcc gac cac c tc acg ccg gtg ctc gcg<br>Pro Leu Lys Arg Cys Ile Phe Ser Asp His L eu Thr Pro Val Leu Ala<br>65                        70                     75                    80 | 240 |
| tac cgc tgc ctc gtc agg gag gac gac cgc g ag gcg ccc agc ttc ctg<br>Tyr Arg Cys Leu Val Arg Glu Asp Asp Arg G lu Ala Pro Ser Phe Leu<br>                85                              90                        95 | 288 |
| ttt gag tcc gtc gag cag gga tcc gag ggc a cc aat gtg ggg agg tac<br>Phe Glu Ser Val Glu Gln Gly Ser Glu Gly T hr Asn Val Gly Arg Tyr<br>        100                          105                       110 | 336 |
| agt gtg gtt ggg gca cag cct gcg atg gag a tc gta gcc aag gcc aac<br>Ser Val Val Gly Ala Gln Pro Ala Met Glu I le Val Ala Lys Ala Asn<br>             115                      120                      125 | 384 |
| cat gtg act gtc atg gat cat aag atg aag t ct agg agg gag caa ttt<br>His Val Thr Val Met Asp His Lys Met Lys S er Arg Arg Glu Gln Phe<br>130                       135                     140 | 432 |
| gcg cct gac ccg atg aag ata cca agg agc a tt atg gaa cag tgg aac<br>Ala Pro Asp Pro Met Lys Ile Pro Arg Ser I le Met Glu Gln Trp Asn<br>145                       150                      155                   160 | 480 |
| cca cag att gtt gaa ggc ctc cct cat gca t tt tgt gga gga tgg gtt<br>Pro Gln Ile Val Glu Gly Leu Pro His Ala P he Cys Gly Gly Trp Val<br>                   165                      170                      175 | 528 |
| gga ttc ttc tct tac gac aca gtg cgt tat g tt gaa aca aag aag ctt<br>Gly Phe Phe Ser Tyr Asp Thr Val Arg Tyr V al Glu Thr Lys Lys Leu<br>                  180                          185                    190 | 576 |
| cca ttt tct aac gcg cca gag gat gat agg a ac ctt cct gac atc cat<br>Pro Phe Ser Asn Ala Pro Glu Asp Asp Arg A sn Leu Pro Asp Ile His<br>             195                      200                      205 | 624 |
| tta ggc ctc tac aat gac ata gtt gtg ttt g at cat gtt gaa aag aaa<br>Leu Gly Leu Tyr Asn Asp Ile Val Val Phe A sp His Val Glu Lys Lys<br>        210                          215                      220 | 672 |
| aca cat gtt ata cat tgg gtg agg gta gat t gc cat gag tca gtt gac<br>Thr His Val Ile His Trp Val Arg Val Asp C ys His Glu Ser Val Asp<br>225                       230                      235                   240 | 720 |
| gaa gcg tat gag gac ggg aag aat cag ctg g aa gct ttg tta tca aga<br>Glu Ala Tyr Glu Asp Gly Lys Asn Gln Leu G lu Ala Leu Leu Ser Arg<br>                  245                      250                    255 | 768 |
| tta cat agt gtt aat gtg cca act ctt act g ct ggt tct gta aaa ctt<br>Leu His Ser Val Asn Val Pro Thr Leu Thr A la Gly Ser Val Lys Leu<br>             260                      265                      270 | 816 |
| aac gtt ggg caa ttt ggg tca gca cta cag a aa tca tca atg tca agg<br>Asn Val Gly Gln Phe Gly Ser Ala Leu Gln L ys Ser Ser Met Ser Arg<br>        275                          280                      285 | 864 |
| gag gac tat aag aaa gct gtt gtt caa gca a aa gag cac att cta gct<br>Glu Asp Tyr Lys Lys Ala Val Val Gln Ala L ys Glu His Ile Leu Ala<br>290                       295                      300 | 912 |
| ggt gac att ttt caa gta gtc tta agc cag c gt ttt gag agg cgt aca<br>Gly Asp Ile Phe Gln Val Val Leu Ser Gln A rg Phe Glu Arg Arg Thr<br>305                       310                      315                   320 | 960 |
| ttt gct aac ccc ttt gag gtg tac cgt gca t tg cgt att gtc aat cct<br>Phe Ala Asn Pro Phe Glu Val Tyr Arg Ala L eu Arg Ile Val Asn Pro<br>                  325                          330                    335 | 1008 |
| agt cct tat atg gcc tat cta cag gct cgt g gt tgt att ctg gta gca<br>Ser Pro Tyr Met Ala Tyr Leu Gln Ala Arg G ly Cys Ile Leu Val Ala<br>             340                      345                      350 | 1056 |
| tca agt cct gaa att ctt acc cgg gtg gaa a ag agg aca att gtc aac<br>Ser Ser Pro Glu Ile Leu Thr Arg Val Glu L ys Arg Thr Ile Val Asn<br>        355                          360                      365 | 1104 |
| agg cca ctt gct gga aca att aga aga gga a aa tcg aaa gca gaa gac<br>Arg Pro Leu Ala Gly Thr Ile Arg Arg Gly L ys Ser Lys Ala Glu Asp<br>370                       375                      380 | 1152 |

-continued

| | |
|---|---|
| aaa gtt tta gaa caa ctg ctg ttg agt gat g ga aag cag tgt gct gag<br>Lys Val Leu Glu Gln Leu Leu Leu Ser Asp G ly Lys Gln Cys Ala Glu<br>385                    390                   395                 400 | 1200 |
| cat att atg tta gta gat ctt gga cgg aat g at gtt gga aag gtg tcc<br>His Ile Met Leu Val Asp Leu Gly Arg Asn A sp Val Gly Lys Val Ser<br>                     405                   410                   415 | 1248 |
| aaa cca ggt tca gta aag gtg gag aaa ctg a tg aac gtt gaa cga tat<br>Lys Pro Gly Ser Val Lys Val Glu Lys Leu M et Asn Val Glu Arg Tyr<br>          420                   425                   430 | 1296 |
| tca cat gtc atg cac att agc tca aca gtt a ct gga gag ttg cgt gat<br>Ser His Val Met His Ile Ser Ser Thr Val T hr Gly Glu Leu Arg Asp<br>               435                   440                   445 | 1344 |
| gat ctg act tgt tgg gat gct ctt cga gca g ca ttg ccc gtt gga aca<br>Asp Leu Thr Cys Trp Asp Ala Leu Arg Ala A la Leu Pro Val Gly Thr<br>450                    455                   460 | 1392 |
| gtt agt ggt gca cca aag gtg aga gcg atg g ag ctg att gac cag atg<br>Val Ser Gly Ala Pro Lys Val Arg Ala Met G lu Leu Ile Asp Gln Met<br>465                    470                   475                 480 | 1440 |
| gaa ggg aag atg cgt ggg ccg tac agt ggt g gc ttt gga ggg gtt tct<br>Glu Gly Lys Met Arg Gly Pro Tyr Ser Gly G ly Phe Gly Gly Val Ser<br>                     485                   490                   495 | 1488 |
| ttc cgt gga gac atg gac atc gca ctt gct c tc cgt acc atc gtc ttc<br>Phe Arg Gly Asp Met Asp Ile Ala Leu Ala L eu Arg Thr Ile Val Phe<br>500                    505                   510 | 1536 |
| ccc acg gga tct cgc ttc gac acc atg tac t cc tac act gac aag aat<br>Pro Thr Gly Ser Arg Phe Asp Thr Met Tyr S er Tyr Thr Asp Lys Asn<br>               515                   520                   525 | 1584 |
| gct cgt cag gag tgg gtg gct cac ctt cag g ct gga gct ggg atc gtc<br>Ala Arg Gln Glu Trp Val Ala His Leu Gln A la Gly Ala Gly Ile Val<br>530                    535                   540 | 1632 |
| gct gac agc aag cct gac gat gag cat cag g ag tgc ttg aac aag gct<br>Ala Asp Ser Lys Pro Asp Asp Glu His Gln G lu Cys Leu Asn Lys Ala<br>545                    550                   555                 560 | 1680 |
| gct ggc ctt gct cgt gcc atc gat ctt gcc g ag tct aca ttc gta gat<br>Ala Gly Leu Ala Arg Ala Ile Asp Leu Ala G lu Ser Thr Phe Val Asp<br>               565                   570                   575 | 1728 |
| gag tag<br>Glu | 1734 |

<210> SEQ ID NO 13
<211> LENGTH: 577
<212> TYPE: PRT
<213> ORGANISM: Artificial Sequence
<220> FEATURE:
<223> OTHER INFORMATION: Modified amino acid se quence of Sequence No. 2

<400> SEQUENCE: 13

Met Ala Ser Leu Val Leu Ser Leu Arg Ile A la Arg Ser Thr Pro Pro
1               5                   10                   15

Leu Gly Leu Gly Gly Gly Arg Phe Arg Gly A rg Arg Gly Ala Val Ala
               20                   25                   30

Cys Arg Ala Ala Thr Phe Gln Gln Leu Asp A la Val Ala Val Arg Glu
               35                   40                   45

Glu Glu Ser Lys Phe Lys Ala Gly Ala Ala G lu Gly Cys Asn Ile Leu
        50                   55                   60

Pro Leu Lys Arg Cys Ile Phe Ser Asp His L eu Thr Pro Val Leu Ala
65                    70                   75                 80

Tyr Arg Cys Leu Val Arg Glu Asp Asp Arg G lu Ala Pro Ser Phe Leu
               85                   90                   95

-continued

```
Phe Glu Ser Val Glu Gln Gly Ser Glu Gly Thr Asn Val Gly Arg Tyr
            100                 105                 110
Ser Val Val Gly Ala Gln Pro Ala Met Glu Ile Val Ala Lys Ala Asn
        115                 120                 125
His Val Thr Val Met Asp His Lys Met Lys Ser Arg Arg Glu Gln Phe
    130                 135                 140
Ala Pro Asp Pro Met Lys Ile Pro Arg Ser Ile Met Glu Gln Trp Asn
145                 150                 155                 160
Pro Gln Ile Val Glu Gly Leu Pro His Ala Phe Cys Gly Gly Trp Val
                165                 170                 175
Gly Phe Phe Ser Tyr Asp Thr Val Arg Tyr Val Glu Thr Lys Lys Leu
            180                 185                 190
Pro Phe Ser Asn Ala Pro Glu Asp Asp Arg Asn Leu Pro Asp Ile His
        195                 200                 205
Leu Gly Leu Tyr Asn Asp Ile Val Val Phe Asp His Val Glu Lys Lys
    210                 215                 220
Thr His Val Ile His Trp Val Arg Val Asp Cys His Glu Ser Val Asp
225                 230                 235                 240
Glu Ala Tyr Glu Asp Gly Lys Asn Gln Leu Glu Ala Leu Leu Ser Arg
                245                 250                 255
Leu His Ser Val Asn Val Pro Thr Leu Thr Ala Gly Ser Val Lys Leu
            260                 265                 270
Asn Val Gly Gln Phe Gly Ser Ala Leu Gln Lys Ser Ser Met Ser Arg
        275                 280                 285
Glu Asp Tyr Lys Lys Ala Val Val Gln Ala Lys Glu His Ile Leu Ala
    290                 295                 300
Gly Asp Ile Phe Gln Val Val Leu Ser Gln Arg Phe Glu Arg Arg Thr
305                 310                 315                 320
Phe Ala Asn Pro Phe Glu Val Tyr Arg Ala Leu Arg Ile Val Asn Pro
                325                 330                 335
Ser Pro Tyr Met Ala Tyr Leu Gln Ala Arg Gly Cys Ile Leu Val Ala
            340                 345                 350
Ser Ser Pro Glu Ile Leu Thr Arg Val Glu Lys Arg Thr Ile Val Asn
        355                 360                 365
Arg Pro Leu Ala Gly Thr Ile Arg Arg Gly Lys Ser Lys Ala Glu Asp
    370                 375                 380
Lys Val Leu Glu Gln Leu Leu Ser Asp Gly Lys Gln Cys Ala Glu
385                 390                 395                 400
His Ile Met Leu Val Asp Leu Gly Arg Asn Asp Val Gly Lys Val Ser
                405                 410                 415
Lys Pro Gly Ser Val Lys Val Glu Lys Leu Met Asn Val Glu Arg Tyr
            420                 425                 430
Ser His Val Met His Ile Ser Ser Thr Val Thr Gly Glu Leu Arg Asp
        435                 440                 445
Asp Leu Thr Cys Trp Asp Ala Leu Arg Ala Ala Leu Pro Val Gly Thr
    450                 455                 460
Val Ser Gly Ala Pro Lys Val Arg Ala Met Glu Leu Ile Asp Gln Met
465                 470                 475                 480
Glu Gly Lys Met Arg Gly Pro Tyr Ser Gly Gly Phe Gly Gly Val Ser
                485                 490                 495
Phe Arg Gly Asp Met Asp Ile Ala Leu Ala Leu Arg Thr Ile Val Phe
            500                 505                 510
```

Pro Thr Gly Ser Arg Phe Asp Thr Met Tyr Ser Tyr Thr Asp Lys Asn
            515                 520                 525

Ala Arg Gln Glu Trp Val Ala His Leu Gln Ala Gly Ala Gly Ile Val
        530                 535                 540

Ala Asp Ser Lys Pro Asp Asp Glu His Gln Glu Cys Leu Asn Lys Ala
545                 550                 555                 560

Ala Gly Leu Ala Arg Ala Ile Asp Leu Ala Glu Ser Thr Phe Val Asp
                565                 570                 575

Glu

<210> SEQ ID NO 14
<211> LENGTH: 24
<212> TYPE: DNA
<213> ORGANISM: Artificial Sequence
<220> FEATURE:
<223> OTHER INFORMATION: Synthetic DNA

<400> SEQUENCE: 14
accgctgcct cgtcagggag gacg                                      24

<210> SEQ ID NO 15
<211> LENGTH: 21
<212> TYPE: DNA
<213> ORGANISM: Artificial Sequence
<220> FEATURE:
<223> OTHER INFORMATION: Synthetic DNA

<400> SEQUENCE: 15
ctcaaaacgc tggcttaaga c                                         21

<210> SEQ ID NO 16
<211> LENGTH: 25
<212> TYPE: DNA
<213> ORGANISM: Artificial Sequence
<220> FEATURE:
<223> OTHER INFORMATION: Synthetic DNA

<400> SEQUENCE: 16
gagtcagttg acgaagcgta tgagg                                     25

<210> SEQ ID NO 17
<211> LENGTH: 24
<212> TYPE: DNA
<213> ORGANISM: Artificial Sequence
<220> FEATURE:
<223> OTHER INFORMATION: Synthetic DNA

<400> SEQUENCE: 17
gtacatttgc taacccctt gagg                                       24

<210> SEQ ID NO 18
<211> LENGTH: 23
<212> TYPE: DNA
<213> ORGANISM: Artificial Sequence
<220> FEATURE:
<223> OTHER INFORMATION: Synthetic DNA

<400> SEQUENCE: 18
caaaggggtt agcaaatgta cgc                                       23

<210> SEQ ID NO 19
<211> LENGTH: 26
<212> TYPE: DNA
<213> ORGANISM: Artificial Sequence -continued

```
<220> FEATURE:
<223> OTHER INFORMATION: Synthetic DNA

<400> SEQUENCE: 19
gttcaacgtt catcagtttc tccacc                                          26
```

GENE ENCODING α-SUBUNIT OF RICE ANTHRANILATE SYNTHASE AND DNA RELATING THERETO

TECHNICAL FIELD

The present invention relates to genes which respectively encode the a-subunits of the two isozymes (isoenzymes) of rice anthranilate synthase, as well as to DNAs relating to said genes. Specifically, the present invention relates to two novel DNA segments respectively encoding such proteins which are respectively the α-subunits of the two isozymes, i.e. the first isozyme and the second isozyme, of anthranilate synthase participating in the biosynthesis of tryptophan in rice plants.

Another aspect of the present invention relates to a novel DNA which encodes a novel protein having the activity of the α-subunit protein of the first isozyme of anthranilate synthase. The present invention also relates to a novel recombinant vector in which said novel DNA has been inserted. Further, *Escherichia coli*, plants and seeds which have been transformed with said novel DNA are embraced within the scope of the present invention.

Another aspect of the present invention relates to a method of increasing the tryptophan content of a plant by the use of the novel DNA of the present invention. Further, the present invention relates to a method of selecting a transformed plant cell containing the novel DNA of the present invention, and to a method of producing a transformed plant containing the novel DNA.

Another aspect of the present invention relates to a DNA which acts as a promoter for the rice anthranilate synthase gene.

BACKGROUND ART

Grains such as rice, maize and wheat are important nutrient source for humans and domestic animals. However, their nutritive value is low because they contain only a small amount of tryptophan, which is one of the essential amino acids. Thus, a need exists for a new plant variety capable of producing grain which has a high nutritive value with a high tryptophan content.

In the tryptophan biosynthetic pathway in a plant, anthranilic acid is biosynthesized from chorismic acid. It is known that anthranilate synthase (hereinafter sometimes referred to as ASA) catalyzes the formation of anthranilic acid and tryptophan is formed from anthranilic acid via indole through six-step enzyme reaction [Seikagaku Jikken Koza (Lectures on Experiments in Biochemistry), vol. 11, pp. 652–653 (1976) published by Tokyo Kagaku Dojin].

Plant anthranilate synthase enzymes so far known consist of plural subunits. For example, anthranilate synthase of Arabidopsis (Japanese name: shiroinunazuna, scientific name: *Arabidopsis thaliana*) is known to consist of two kinds of isozymes, the first isozyme and the second isozyme, each of which is a dimer consisting of the α-subunit and the β-subunit. The gene encoding the α-subunit of the first isozyme of Arabidopsis anthranilate synthase (abbreviated as ASA1) as well as the gene encoding the α-subunit of the second isozyme of Arabidopsis anthranilate synthase (abbreviated as ASA2) (the genes are referred to as asa1 and asa2, respectively) have been isolated, and their DNA sequences have been determined [The Plant Cell, vol. 4, pp. 721–733 (1992)].

On the other hand, we, the present inventors already took an interest in the α-subunit of anthranilate synthase as expected to have a functional domain which plays an important role in the regulation of tryptophan biosynthesis in rice, and we made studies in 1996 to isolate a gene encoding the anthranilate synthase protein, for the purpose of obtaining information about the biosynthetic regulation mechanism of tryptophan and a phytohormone IAA. According to the abstract of the report of these studies, we, the present inventors extracted mRNA and genomic DNA from rice (Norin No.8) as explant, and we prepared a cDNA library and a genomic DNA library, subjected these libraries to the genomic Southern analysis and made screening of the libraries with using cDNA fragments of the Arabidopsis asa gene as the probes, and thereby we obtained DNA which is supposed to be corresponding to the asa gene of rice anthranilate synthase [Ikushu (Breeding), vol. 46, suppl. vol. 2, p. 28 (1996)]. Although it is reported in this abstract that a DNA fragment corresponding to the ASA gene of rice anthranilate synthase was obtained, specific techniques used for obtaining said DNA fragment are not disclosed there, and it is reported that the nucleotide sequence of said DNA fragment has not been determined yet. The abstract of the above report also refers to the presence of two kinds of DNAs which are supposed to be corresponding to the gene for encoding the rice anthranilate synthase [Ikushu (Breeding), vol. 46, suppl. vol. 2, p. 28 (1996)].

There has also been a report on that DNA of the ASA gene encoding the α-subunit of the first isozyme of Arabidopsis ASA and also a DNA fragment as obtained by modifying said DNA are introduced into a tobacco plant with the expression of the function of said gene in tobacco [Massachusetts Institute of Technology, Cambridge, Mass. (1993)].

However, so far as the present inventors are aware of, no report has been made on the analysis of the amino acid sequence of a protein which is the α-subunit of rice ASA isozyme, and on the method which was actually used for obtaining a gene encoding the α-subunit of rice ASA isozyme. The promoter sequence relating to the expression of said gene is not known, either. Further, there has been no report on the utilization of a gene encoding the rice ASA.

One object of the present invention is to obtain from a rice plant a novel gene relating to the rice ASA, specifically, a new DNA for encoding the α-subunit of the first isozyme of the rice ASA. Another object of the present invention is to determine the nucleotide sequence of this DNA.

Another object of the present invention is to provide a novel DNA capable of encoding a novel protein having the activity of the α-subunit of the first isozyme of rice ASA. A further object of the present invention is to transform useful plants such as maize, rice, soybean, wheat, barley, tomato and potato, with said novel DNA, and to provide novel useful transformant plants capable of producing seeds which have a high tryptophan content. A yet further object of the present invention is to construct a novel DNA sequence capable of encoding a protein having the activity of the α-subunit of the first isozyme of rice ASA, and to provide an efficient method for obtaining cells and plants as transformed with said novel DNA.

The other objects of the present invention will be clear from by the descriptions below.

DISCLOSURE OF THE INVENTION

In order to accomplish the above-described objects, the present inventors have made a series of studies. First, a study has been made for obtaining such genes which respectively encode the α-subunits of the two ASA isozymes from rice.

In this study, we, the inventors have extracted a total RNA from tissue of an explant of rice such as disrupted green stem and leaf by a known technique for the gene engineering, and we have isolated mRNAs from the extracted total RNAs by a conventional method, and have successfully obtained cDNAs of rice from the mRNAs with using a commercially available cDNA synthesis kit. It has been found through trials and errors that recombinant vectors can be constructed by ligating the above cDNAs into such a phage vector (available from STRATAGENE) as prepared by treating the end of an EcoRI-cleaved fragment of λ gt11 phage vector with an alkaline phosphatase derived from calf small intestines, and that replicable recombinant λ phages can be constructed by packaging the obtained recombinant vectors in a λ phage.

Further, it has been found that a lot of recombinant λ phages can be obtained in the form of a large number of plaques, by incubation of *Escherichia coli* Y1088 as infected with the above recombinant λ phages, and that a group of recombinant λ phages present in the resultant plaques comprises various phages each containing the rice-derived cDNA and can be utilized as a rice cDNA library.

On the other hand, we, the present inventors have now prepared by chemical synthesis such two oligonucleotides which can be considered to be suitable for use as primers in PCR, and which are namely the first oligonucleotide consisting of 21 nucleotides and the second oligonucleotide consisting of 24 nucleotides, with our reference to the amino acid sequences of the proteins which are respectively the α-subunits of the first and second isozymes of Arabidopsis ASA, as well as the nucleotide sequences of the genes encode said proteins presumable from their amino acid sequences, which are described in the above-mentioned publication [The Plant Cell, vol. 4, pp. 721–733 (1992)].

PCR amplification has been carried out by us with using a mixture of the first and second oligonucleotides mentioned above with a commercially available Arabidopsis cDNA library (utilized as a template). And then it has now been found that the first and second oligonucleotides serve as primers (complementary DNAs) which are necessary in PCR, and that DNA fragments, which constitute parts of the DNA sequences corresponding to the genes encoding the α-subunits of the two isozymes of Arabidopsis ASA, can be amplified by PCR. The resulting products of the amplification of parts of the genes encoding the α-subunits of the first and second isozymes of Arabidopsis ASA have now been successfully recovered from the reaction mixture of PCR, as DNA probes.

The present inventors have succeeded, as a result of many errors and trials, in isolating eight plaques of the recombinant λ phages carrying the genes respectively encoding the α-subunits of the first and second isozymes of rice ASA, from the previously obtained rice cDNA library (three hundred thousand plaques of recombinant λ phages mentioned above), by the phage plaque hybridization method with using the DNA probe obtained above. The recombinant λ phages in said eight plaques have been separately amplified, and then each λ phage DNA has been isolated by a conventional method.

The DNA fragments are obtained by digesting with the restriction enzyme EcoRI the above recombinant phage DNAs which are carrying the DNA sequences assumable to be corresponding to the genes encoding the α-subunits of the first and second isozymes of rice ASA. Said DNA fragments have been inserted into the EcoRI cleavage site of the commercially available plasmid vector pBluescript II SK(+), by using a DNA ligation kit. *Escherichia coli* XLI-Blue MRF' has been transformed with the thus obtained recombinant plasmid vectors, and the resulting transformants have been incubated to give a large number of bacterial cells. Plasmid DNA fragments have been isolated from these cells, and their nucleotide sequences have been analyzed. As a result, we have now confirmed that one of the two DNA sequences, which are contained in the plasmid DNA fragments and assumable to be corresponding to the genes encoding the α-subunits of the first and second isozymes of rice ASA, has the nucleotide sequence shown in SEQ ID NO: 1 of Sequence Listing given hereinafter. It has also now been confirmed that the other one of the above-mentioned two DNA sequences has the nucleotide sequence shown in SEQ ID NO: 10 of Sequence Listing.

Further, so far as the present inventors are aware of, the DNAs having the nucleotide sequences shown in SEQ ID NOS: 1 and 10 of Sequence Listing, respectively, have not been disclosed in any publication, and thus they can be recognized as novel DNA sequences.

The protein, which is encoded by the DNA having the nucleotide sequence shown in SEQ ID NO: 1 of Sequence Listing, is recognized as the protein having the amino acid sequence shown in SEQ ID NO: 2 of Sequence Listing and is also recognized as the protein constituting the α-subunit of the first isozyme of rice ASA.

Accordingly, the first aspect of the present invention provides a DNA encoding a protein which is the α-subunit of the first isozyme of rice anthranilate synthase, and which protein has the amino acid sequence shown in SEQ ID NO: 2 of Sequence Listing.

The DNA according to the first aspect of the present invention can specifically be the DNA having the nucleotide sequence shown in SEQ ID NO: 1 of Sequence Listing.

The new DNA of the first aspect of the present invention is the DNA encoding the protein which is the α-subunit of the first isozyme of rice ASA. This new DNA has now been obtained from the rice cDNA library by recombinant DNA techniques, as described above, based on the study made by the present inventors. However, once the nucleotide sequence of the DNA has now been determined by the present invention, it can also be chemically synthesized from nucleotides, with referring to the nucleotide sequence of SEQ ID NO: 1. It is also possible to produce the DNA of the first aspect of the present invention in a known manner from a rice chromosomal DNA library by the known polymerase chain reaction (PCR) or hybridization, with using as a probe such a synthetic nucleotide as prepared with referring to the nucleotide sequence of SEQ ID NO: 1, or with using the prepared synthetic oligonucleotide as a primer.

The protein which is encoded by the DNA having the nucleotide sequence shown in SEQ ID NO: 10 of Sequence Listing, is recognized as the protein having the amino acid sequence shown in SEQ ID NO: 11 and is also recognised as the protein constituting the α-subunit of the second isozyme of rice ASA.

Accordingly, the second aspect of the present invention provides a DNA encoding a protein which is the α-subunit of the second isozyme of rice anthranilate synthase and which protein has the amino acid sequence shown in SEQ ID NO: 11 of Sequence Listing.

The DNA according to the second aspect of the present invention can specifically be the DNA having the nucleotide sequence shown in SEQ ID NO: 10 of Sequence Listing.

The new DNA of the second aspect of the present invention is the DNA encoding the protein which is the α-subunit of the second isozyme of rice ASA. This new DNA has been obtained from the rice cDNA library by recombinant DNA techniques, as described above, based on the study made by the present inventors. However, once the nucleotide sequence of the DNA has been determined by the present invention, it can also be chemically synthesized from nucleotides, with referring to the nucleotide sequence of SEQ ID NO: 10. It is also possible to produce the DNA of the second aspect of the present invention in a known manner from a rice chromosomal DNA library by the known polymerase chain reaction (PCR) or hybridization, with using as a probe a synthetic nucleotide as prepared with referring to the nucleotide sequence of SEQ ID NO: 10 or with using the prepared synthetic oligonucleotide as a primer.

Next, the process for preparing the DNAs of the first and second aspects of the present invention from stems and leaves of rice plant by the recombinant DNA techniques is outlined below.

(1) Preparation of Rice mRNA and Construction of Rice cDNA Library

Total RNA is extracted from tissues, e.g. stems and leaves, roots and callus, preferably green stems and leaves, of rice plant (*Oryza sativa*) by a conventional method. After removal of contaminants such as proteins, the total RNA is passed through a column of oligo dT cellulose to purify the poly(A)+RNAs, whereby rice mRNAs can be obtained.

Then, rice cDNAs are synthesized from the above mRNAs with using a commercially available cDNA synthesis kit. The so synthesized cDNAs are ligated into a phage vector such as λgt11 vector or λZAPII vector, and the resulting recombinant vectors are packaged in a λ phage. A number of recombinant phages can be thus prepared, and subsegment incubation of *Escherichia coli* cells as infected with these recombinant phages gives a large number of the recombinant phages as the plaques. The above procedure can be carried out by using a commercially available cDNA cloning kit.

The recombinant phages which are obtained as the plaques of host *E. coli* cells as described above, comprise various phages containing total rice-derived cDNAs and, therefore, can be used as the rice cDNA library.

(2) Construction of Primers for PCR

We, the present inventors have now constructed by chemical synthesis two kinds of oligonucleotides (the two oligonucleotides shown in SEQ ID NOS: 8 and 9 of Sequence Listing given hereinafter) as primers for PCR (complementary DNAs), while we are referring to the nucleotide sequence which is common to the known nucleotide sequences of the genes encoding the α-subunits of the first and second isozymes of Arabidopsis ASA (on-line data base EMBL: M92353), and while we are taking into account the fact that the first isozyme of Arabidopsis ASA has a higher expression level in a plant.

(3) Preparation of DNA Probes

The DNA probes are then prepared, which are to be used for selectively obtaining the desired DNAs encoding the rice ASA α-subunits from the rice cDNA library previously obtained as said plaques comprising a large number of recombinant phages. For the preparation of said DNA probes, the DNAs constituting some parts of the genes encoding the α-subunits of the first and second isozymes of Arabidopsis ASA are amplified by PCR, with using the above-mentioned synthetic oligonucleotides as the primers and an Arabidopsis cDNA library as the template.

After making repeated amplification reactions by PCR, the products of the amplification of DNA fragments which are some parts of the DNA sequences corresponding to the genes encoding the Arabidopsis ASA α-subunits are recovered from the reaction mixture of PCR as the desired DNA probes.

(4) Selection of cDNA clones of Rice ASA α-Subunit Genes from Rice cDNA Library

The rice cDNA library is thus obtained as a large number of plaques of the recombinant phages in the above, and it is next subjected to a screening by the phage plaque hybridization using the above DNA probes. There can be selected several plaques comprising recombinant phages carrying the DNA sequences which are corresponding, as a whole, to the desired rice ASA α-subunit genes.

The recombinant phages are thus obtained as the selected plaques, and they comprise the DNA fragments carrying the desired DNA sequences which are corresponding to the cDNA colone of the rice ASA α-subunit genes, as explained below.

In more detail, thus, a phage is obtained from each of the plaques selected by the plaque hybridization as described above, and a phage DNA is recovered from said phage. The phage DNA is then treated according to the dideoxy method or the like, to determine the nucleotide sequence of the rice-derived DNA fragment inserted therein. For this, the amino acid sequence determined based on the protein-encoding region (open reading frame) in the nucleotide sequence of the rice-derived DNA insert is compared with the known amino acid sequence of the Arabidopsis ASA α-subunit protein, for the judgment of homology. In this manner, the phage DNAs obtained as above can be specified to be the DNA fragments carrying the DNA sequences which are corresponding to the rice ASA α-subunit genes.

Thus, the DNA insert fragments, which are judged to carry the DNA sequences corresponding to the rice ASA α-subunit genes, can then be obtained by cleavage from the resulting phage DNAs of the phages selected in the above manner, with using restriction enzymes.

(5) Cloning of cDNA Corresponding to Rice ASA α-Subunit Genes

The above DNAs, which have been obtained by cleavage from the phages as the DNA fragments carrying the DNA sequences corresponding to the rice ASA α-subunit genes, are inserted into the EcoRI cleavage site of the plasmid vector pBluescript II SK(+) in order to construct recombinant plasmid vectors. *E. coli* XL1-Blue MRF' is transformed with the thus constructed recombinant plasmid vectors. The resulting *E. coli* transformants are cultured to effect cloning of the above recombinant plasmids comprising the DNA fragments which are carrying the DNA sequences corresponding to the rice ASA α-subunit genes. Thus, the DNA fragments carrying the DNA sequences corresponding to the rice ASA α-subunit genes can be cloned.

According to the present invention, as explained in the above, two kinds of DNA fragments which are different in number of nucleotides were obtained in the form of the DNA fragments, which can be prepared by ligation of them into the plasmid vector pBluescript II SK(+) and cloning of the vector in *E. coli* as described above, and which DNA fragments carry the DNA sequences corresponding to the rice ASA α-subunit genes. The smaller one of the two DNA fragments thus obtained by us is provisionally named as DNA fragment X, and the larger one is provisionally named as DNA fragment Y.

(6) Sequence Analysis of Cloned DNAs (i) The DNA fragments X and Y are then separately cleaved from the cloned recombinant plasmids mentioned above with the restriction enzyme EcoRI, as the two kinds of DNA fragments carrying the DNA sequences which are corresponding to the rice ASA α-subunit genes. When the treatment of the DNA fragments X and Y thus cleaved is made by means of a commercially available nucleotide sequence determination kit, the entire sequences of the DNA fragments X and Y carrying the DNA sequences, which are corresponding to the rice ASA α-subunit genes, can be determined. The DNA sequence encoding the α-subunit of the first isozyme of rice ASA was thus determined for the above DNA fragment X, and it exhibits the nucleotide sequence which is shown in SEQ ID NO: 1 of Sequence Listing given below and which consists of 1734 nucleotides. This DNA sequence, which is named as "OSASA-1 sequence", is an example of the DNA according to the first aspect of the present invention.

Incidentally, the above DNA fragment X was obtained in Example 1 given hereinafter, and the DNA fragment X carries the DNA sequence having the nucleotide sequence shown in SEQ ID NO: 1 of Sequence listing and corresponding to the gene encoding the α-subunit of the first isozyme of rice ASA. This DNA fragment X was inserted into the EcoRI cleavage site of the plasmid vector pBluescript II SK(+) (STRATAGENE). The obtained recombinant plasmid vector (named vector pOSASA-1) was introduced into *E. coli* XL1-Blue MRF', and the resulting transformant was named *Escherichia coli* XL1-Blue MRF', (OS-asa1). This *E. coli* transformant was deposited with the National Institute of Bioscience and Human-Technology, Agency of Industrial Science and Technology, Tsukuba-shi, Ibaraki-ken, Japan on Aug. 18, 1997 with accession number FERM P-16388. Further, *Escherichia coli* OS-asa1 was deposited with the above depository on Aug. 7, 1998 under the Budapest Treaty with accession number FERM BP-6453.

The DNA according to the first aspect of the present invention is useful in that the use of the information on the nucleotide sequence of the present DNA as determined by the present invention makes it possible to produce of a large amount of the α-subunit protein of the first isozyme of rice ASA by chemical synthesis. And thus the present DNA is capable of contributing to the development of enzymatic studies of the α-subunit protein of the first isozyme of rice ASA.

(ii) The DNA sequence encoding the α-subunit of the second isozyme of rice ASA was decided as described above for the above DNA fragment Y. DNA fragment Y exhibits the nucleotide sequence which is shown in SEQ ID NO: 10 of Sequence Listing and which consists of 1821 nucleotides. This DNA sequence is named "OSASA-2 sequence", and is an example of the DNA according to the second aspect of the present invention.

The above DNA fragment Y was obtained in Example 1, and it carries the DNA sequence having the nucleotide sequence shown in SEQ ID NO: 10 of Sequence Listing and corresponding to the gene encoding the α-subunit of the second isozyme of rice ASA. This DNA fragment Y was inserted into the EcoRI cleavage site of the plasmid vector pBluescript II SK(+). The obtained recombinant plasmid vector(named vector pOSASA-2) as introduced into *E. coli* XL1-Blue MRF', and the resulting transformant was named *Escherichia coli* XL1-Blue MRF', (OS-asa2). This *E. coli* transformant was deposited with the National Institute of Bioscience and Human-Technology, Agency of Industrial Science and Technology on Jun. 18, 1998 with accession number FERM P-16853, and also on Aug. 7, 1998 under the Budapest Treaty with accession number FERM BP-6454.

On the other hand, it is widely recognized in the art that even when a single or plural amino acid residues in the amino acid sequence of a protein having a certain physiological activity are deleted, and/or substituted by other amino acid residues, and/or a single or plural amino acid residues are added to said amino acid sequence, the resulting sequence sometimes retains the original physiological activity of the protein of the original amino acid sequence. Thus, the DNA of the first aspect of the present invention can be a DNA which encodes a protein having the activity of the α-subunit of the first isozyme of rice ASA, even after modification is made to one or several parts of its nucleotide sequence.

In other words, the DNA according to the first aspect of the present invention remains capable of encoding a protein having the activity of the α-subunit of the first isozyme of rice ASA, even after a single or plural nucleotides, for example, 1, 2 or 3 to 10 nucleotides in the nucleotide sequence thereof are altered to other nucleotides.

Accordingly, the third aspect of the present invention provides a DNA encoding a protein having the activity of the α-subunit of the first isozyme of anthranilate synthase and having such an amino acid sequence as formed by modification of the amino acid sequence shown in SEQ ID NO: 2 of Sequence Listing given below, said modification being made by deletion of a single or plural amino acid residues in said amino acid sequence, and/or by substitution of a single or plural amino acid residues in said amino acid sequence by other amino acid residues, and/or by insertion or addition of amino acid residues to said amino acid sequence.

The DNA according to the third aspect of the present invention is a modification of the DNA according to the first aspect of the present invention. It can be obtained by modifying the nucleotide sequence of the DNA of the first aspect of the present invention by a method such as site-specific mutagenesis, so that a modified DNA still will encode a protein having such an amino acid sequence in which amino acid residues at specific positions of the protein as encoded by the modified DNA have been deleted, substituted or added in the above-described manner.

The modified DNA according to the third aspect of the present invention can also be obtained by a method comprising mutating cells containing DNA fragments carrying the DNA of the first aspect of the present invention, and then selecting from the mutated cells such a DNA which can hybridize with the DNA having the nucleotide sequence shown in SEQ ID NO: 1 under stringent conditions, and which has a nucleotide sequence partially different from the sequence of SEQ ID NO: 1. The term "stringent conditions" as used herein will refer to the conditions under which so-called specific hybridization with the DNA of the first aspect of the present invention occurs and non-specific hybridization does not occur. Such stringent conditions are difficult to specify numerically, but may include, for example, those conditions which allow such two nucleic acids having a high homology, e.g. such DNAs having 98% or more homology to hybridize with each other, but which do not allow such two nucleic acids having a less homology to hybridize with each other.

Accordingly, an example of the DNA according to the third aspect of the present invention may be such a DNA which has a nucleotide sequence partially different from the nucleotide sequence shown in SEQ ID NO: 1, which has a high homology to the nucleotide sequence of SEQ ID NO: 1, which is capable of hybridizing with the DNA having the nucleotide sequence of SEQ ID NO: 1 under stringent conditions, and which encodes a protein having anthranilate synthase activity.

The DNA according to the third aspect of the present invention can be a DNA encoding a protein which has the amino acid sequence shown in SEQ ID NO: 13, and which is such a protein having the activity of the α-subunit of the first isozyme of rice anthranilate synthase but being insensitive to the feedback inhibition by tryptophan.

A specific example of the DNA according to the third aspect of the present invention is the DNA sequence which has the nucleotide sequence of SEQ ID NO: 12 of Sequence Listing, and which was obtained by the method described in Example 2 below and is named as "modified D sequence" therein.

The above DNA, named as the modified D sequence, has the nucleotide sequence of SEQ ID NO: 12 and is the DNA which encodes the above protein having the activity of the α-subunit of the first isozyme of rice ASA but being insensitive to the feedback inhibition by tryptophan.

Also encompassed by the third aspect of the present invention is a DNA fragment encoding such a protein which has been modified in a manner as described above, and which is capable of constituting a holo-enzyme having the anthranilate synthase activity, in association with the anthranilate synthase β-subunit. That is, the third aspect of the present invention may include within its scope a DNA encoding such a protein which has an amino acid sequence as constructed by deletion or substitution or insertion or addition of one to several amino acid residues within the amino acid sequence of SEQ ID NO: 2 and which protein is still capable of constituting a holo-enzyme having anthranilate synthase activity, in association with the anthranilate synthase β-subunit.

When the use of the DNA of the first aspect of the present invention or a part thereof is made as a probe, it is possible that the DNA sequence of the gene of the α-subunit of the first isozyme of ASA is produced from a plant chromosome by a conventional method. The ASA genes as derived from rice chromosome shall comprise the introns as described below. Such a DNA sequence segmented with the introns, which can be obtained in the above manner, is also embraced within the scope of the third aspect of the present invention, so far as the such DNA sequence encodes a protein capable of constituting the holo-enzyme having the anthranilate synthase activity, in association with the anthranilate synthase β-subunit.

By the expression "ASA α-subunit gene" as used herein is meant a DNA encoding the α-subunit protein which is capable of constituting the holoenzyme having anthranilate synthase activity, in association with the rice anthranilate synthase β-subunit. The term "α-subunit" as used here will refer to one or both of the α-subunits of the first and second isozymes of rice ASA.

As described above, the DNA of the first aspect of the present invention can be modified into the DNA of the third aspect of the present invention. Likewise, the DNA of the second aspect of the present invention, i.e. the DNA encoding the protein which is the α-subunit of the second isozyme of rice ASA, can also be modified by altering a part of the nucleotide sequence of the DNA of the second aspect invention.

Accordingly, the fourth aspect of the present invention provides a DNA encoding a protein having the activity of the α-subunit of the second isozyme of anthranilate synthase and having such an amino acid sequence as formed by modification of the amino acid sequence shown in SEQ ID NO: 11 of Sequence Listing; said modification being made by deletion of a single or plural amino acid residues in said amino acid sequence, and/or by substitution of a single or plural amino acid residues in said amino acid sequence by other amino acid residues, and/or by insertion or addition of amino acid residues to said amino acid sequence.

The DNA according to the fourth aspect of the present invention can be a DNA which encodes the protein having the activity of the α-subunit of the second isozyme of anthranilate synthase; said DNA having a nucleotide sequence partially different from the nucleotide sequence shown in SEQ ID NO: 10 of Sequence Listing, and said DNA having homology to the nucleotide sequence shown in said SEQ ID NO: 10, and being capable of hybridizing with the DNA having the nucleotide sequence shown in SEQ ID NO: 10, under stringent conditions.

As described above, a specific example of the novel DNA according to the third aspect of the present invention is the DNA sequence which is prepared by the method described in Example 2 and is named as the modified D sequence.

This modified D sequence is the DNA having the nucleotide sequence shown in SEQ ID NO: 12 of Sequence Listing given hereinafter. This modified D sequence corresponds to DNA which is a modified DNA derived from the DNA of the first aspect of the present invention having the nucleotide sequence of SEQ ID NO: 1, in such manner that G (guanine) at nucleotide 967 in the GAC sequence (codon for aspartic acid) at nucleotides 967, 968 and 969 in the sequence of SEQ ID NO: 1 is replaced by A (alanine) so as to provide the AAC a sequence of a codon for asparagine in the positions containing the nucleotide 967 in the sequence of SEQ ID NO:1. The protein encoded by this modified D sequence has the amino acid sequence shown in SEQ ID NO: 13 of Sequence Listing and exhibits the activity of the α-subunit of the first isozyme of rice ASA.

Further, the protein encoded by the modified D sequence according to the third aspect of the present invention is a novel protein whose enzyme activity has been so altered that ASA participating in the tryptophan biosynthetic pathway is made insusceptible of the feedback inhibition by tryptophan which is a biosynthetic product. The DNA encoding this novel protein may be used for the transformation of plants in order to increase the tryptophan content of plants as described after.

Generally, a DNA sequence can be partially altered by known methods such as the Kunkel method (Methods in Enzymology, vol. 154, no. 367) and the oligonucleotide-direct dual amber method.

We, the present inventors have discussed and studied about approaches to the partial alternation of the nucleotide sequence of the DNA of the first aspect of the present invention, for such purpose that the first isozyme of ASA encoded by the DNA of the first aspect of the present invention is modified to be insusceptible of the tryptophan feedback inhibition, while we are referring to the previous report on the known ASA gene of such an Arabidopsis mutant which is resistant to tryptophan analogues [published in "Plant Physiology", vol. 110, pp. 51–59 (1996)]. As a result, the present inventors have got such an anticipative conception that the modified DNA as prepared by replacing guanine (G) at nucleotide 967 in the nucleotide sequence of SEQ ID NO: 1 (OSASA-1 sequence) by adenine (A) will be effective for the above purpose.

On the basis of this conception, we, the present inventors have made various studies. Through many trials and errors, we have now constructed a recombinant plasmid vector by a method wherein a DNA fragment carrying the DNA sequence which is corresponding to the gene of the α-subunit of the first isozyme of rice ASA, i.e. OSASA-1 sequence, is inserted into the EcoRI cleavage site of the plasmid vector pBluescript II SK(+) by using a ligation kit. This recombinant plasmid vector (hereinafter referred to as pOSASA-1) so obtained has been recognized to be suitable as a starting material for the preparation of the desired novel modified DNA.

For the above purpose and in order to achieve the preparation of the desired novel modified DNA from the above starting material, i.e. the above recombinant plasmid vector pOSASA-1 according to by PCR method, we have prepared the following usable four primers by chemical synthesis; which four primers are primer OSASN1, that is, the oligonucleotide having the nucleotide sequence shown in SEQ ID NO: 16 of Sequence Listing given below; and primer OSASN2m, that is, the oligonucleotide having the nucleotide sequence shown in SEQ ID NO: 17; and primer OSASC1, that is, the oligonucleotide having the nucleotide sequence shown in SEQ ID NO: 18; and primer OSASC2, that is, the oligonucleotide having the nucleotide sequence shown in SEQ ID NO: 19 of Sequence Listing.

We, the present inventors have now succeeded in producing the DNA of SEQ ID NO: 12, i.e. the "modified D sequence", which is an example of the modified DNA of the present invention, when we have carryied out the procedure described in Example 2, with utilizing the above recombinant plasmid vector pOSASA-1 as well as the above-mentioned four kinds of the synthetic oligonucletides as the primers.

Outlined below is the process for modifying DNA which are comprising the steps as described in Example 2 herein after and which can be suitably employed for the preparation of a DNA fragment carrying the above "modified D sequence", an example of the third aspect of the present invention.

(1) Cloning of the DNA of the First Aspect of the Present Invention

A DNA fragment, which is carrying the DNA of the first aspect of the present invention having the nucleotide sequence of SEQ ID NO: 1 and consisting of the 1734 nucleotides, i.e. the above-mentioned OSASA-1 sequence, is inserted into the EcoRI cleavage site of the vector pBluescript II SK(+) by the use of a DNA ligation kit, thereby to obtain the above-mentioned recombinant plasmid vector pOSASA-1. This vector is introduced into *E. coli* XLI-Blue MRF', and the resulting *E. coli* transformant is cultured. From the cultured cells is isolated a large amount of the plasmid vector pOSASA-1 by means of ordinary extraction. By this procedure, the DNA sequence according to the first aspect of the present invention, i.e. the OSASA-1 sequence can be cloned.

(2) Construction of Primers for RCR

Four kinds of the oligonucleotides having the nucleotide sequences identified below are synthesized as the primers by using a DNA synthesizer (Model-391, Applied Biosystems, Inc.). Thus, the following four primers are prepared by chemical synthesis, which are the primer OSASN1, namely the oligonucleotide having the nucleotide sequence shown in SEQ ID NO: 16 of Sequence Listing; the primer OSASN2, namely the oligonucleotide having the nucleotide sequence shown in SEQ ID NO: 17; the primer OSASC1, namely the oligonucleotide having the nucleotide sequence shown in SEQ ID NO: 18; and the primer OSASC2, namely the oligonucleotide having the nucleotide sequence shown in SEQ ID NO: 19 of Sequence Listing.

(i) Primer OSASAN1 (primer having the following nucleotide sequence of SEQ ID NO: 16):
5'-GAGTCAGTTGACGAAGCGTATGAGG-3'

(ii) Primer OSASAN2 (primer having the following nucleotide sequence of SEQ ID NO: 17):
5'-GTACATTTGCTAACCCCTTTGAGG-3'

(iii) Primer OSASAC1 (primer having the following nucleotide sequence of SEQ ID NO: 18):
5'-CAAAGGGGTTAGCAAATGTACGC-3'

(iv) Primer OSASAC2 (primer having the following nucleotide sequence of SEQ ID NO: 19):
5'-GTTCAACGTTCATCAGTTTCTCCACC-3'

(3) Amplification of the Desired DNA Fragments by PCR and Recovery Thereof

In order to amplify the desired DNA fragments, the following two reactions, namely reactions (A) and (B), are carried out as the first step of PCR.

The reaction (A) is carried out by a method comprising adding the above recombinant plasmid vector pOSASA-1 as the template, as well as the above primer OSASAN1 (the synthetic oligonucleotide of SEQ ID NO: 16) and the above primer OSASAC1 (the synthetic oligonucleotide of SEQ ID NO: 18; wherein GTT at the 8th to 10th positions from the 5' end of OSASAC1 is capable of inducing the modification part AAC of the "modified D sequence"), to an ordinary reaction mixture for effecting PCR [comprising Tris-HCl, $MgCl_2$, KCl, four kinds of deoxynucleotide triphosphate (dNTP) and La Taq DNA polymerase], and subjecting the resulting mixture to the amplification reaction.

By this reaction (A), a DNA fragment carrying a partial nucleotide sequence of the modified D sequence (said DNA fragment is hereinafter referred to as "DNA fragment-A") may be formed as a product of the amplification.

The reaction (B) is carried out by a method comprising adding the above recombinant plasmid vector pOSASA-1 as the template, as well as the above primer OSASAC2 (the synthetic oligonucleotide of SEQ ID NO: 19) and the above primer OSASAN2 (the synthetic oligonucleotide of SEQ ID NO: 17; wherein AAC at the 12th to 14th positions from the 5' end of OSASAN2 is capable of inducing the modification part AAC of the modified D sequence), to the same reaction mixture for PCR as that used in the reaction (A), and subjecting the resulting mixture to the amplification reaction.

By this reaction (B), a DNA fragment carrying a partial nucleotide sequence of the modified D sequence (said DNA fragment is hereinafter referred to as "DNA fragment-B") may be formed as a product of the amplification.

The above amplification reactions by PCR can be carried out by the use of a commercially available PCR apparatus.

After the completion of amplification reactions, the reaction mixture resulting from the reaction (A) is fractionated by low-melting point agarose electrophoresis, and then a band containing the DNA fragment-A of 268 bp (base pairs) as the amplification product is cut out of the agarose gel. The reaction mixture resulting from the reaction (B) is likewise fractionated by low-melting point agarose electrophoresis, and then a band containing the DNA fragment-B of 336 bp (base pairs) is cut out of the agarose gel.

The so obtained two gel pieces are purified by using a DNA purification kit, e.g. Genclean II (Funakoshi), whereby the purified product of the DNA fragment-A and the purified product of the DNA fragment-B, respectively, are obtained.

Further, as the second step of PCR, a reaction is carried out in this step for the purpose of preparing a DNA fragment of 583 bp (base pairs) (fragment C), which is corresponding to a partial sequence of the DNA sequence having such nucleotide sequence wherein guanine is replaced by adenine at the nucleotide 967 of the nucleotide sequence of SEQ ID NO: 1 (thus, said DNA sequence is corresponding to the "modified D sequence" fragment according to the third aspect of the present invention, which has the nucleotide sequence of SEQ ID NO: 12).

This reaction just in the above is carried out by adding, as the templates, the purified product of DNA fragment-A (268 bp sequence) as produced by amplification in the above reaction (A) as well as the purified product of DNA fragment-B (336 bp sequence) as produced by amplification in the above reaction (B), to an ordinary amplification reaction mixture for effecting PCR (comprising Tris-HCl, MgCl$_2$, KCl, four kinds of dNTP and La Taq DNA polymerase), and subjecting the resulting mixture to the amplification reaction. After the completion of reaction, the reaction mixture is fractionated by low-melting point agarose electrophoresis, and then a band containing the desired DNA fragment of 583 bp (hereinafter referred to as "DNA fragment-C") is cut out of the agarose gel.

The obtained gel piece is purified by using a DNA purification kit, e.g. Genclean II (Funakoshi), thereby to obtain the purified product of the DNA fragment-C. This DNA fragment-C has the nucleotide sequence which is corresponding to a partial sequence of the "modified D sequence" according to the third aspect of the present invention, and which has such structure wherein cleavage sites for the restriction enzymes AflII and BglII are present.

When Cleavage of this DNA fragment-C is made with the restriction enzymes AflII and BglII, there is provided DNA fragment-α of 288 bp which has the desired nucleotide substitution in its sequence, and which has an AflII cleavage site at the 5' end, and has a BalII cleavage site at the 3' end.

(4) Cloning of a DNA Fragment Carrying the Modified D Sequence

The desired DNA fragment carrying the modified D sequence is then prepared by the use of the DNA fragment-C as obtained in the above (3).

First, the DNA fragment-C is treated with the restriction enzymes AflII and BglII, whereby there is isolated a DNA fragment which is carrying a partial sequence of the modified D sequence and which is having an AflII cleavage site at the 5' end and a BglII cleavage site at the 3' end. In this way, a DNA fragment sample (i) which contains the DNA sequence corresponding to the modified D sequence as intended is thus obtained.

Then the plasmid vector pOSASA-1 containing the DNA shown in SEQ ID NO: 1 (i.e. OSASA-1 sequence) is treated with the restriction enzymes AflII and BglII, thereby to obtain plasmid fragment (ii) which has a BglII cleavage site at the 5' end and an AflII cleavage site at the 3' end, and which comprises a sequence of nucleotides 1 to 933 and a sequence of nucleotides 1220 to 1734 in the DNA sequence of SEQ ID NO: 1.

The so obtained AflII-BglII plasmid fragment (ii) is mixed with the above DNA fragment sample (i) which is containing the DNA sequence corresponding to the modified D sequence. The resulting mixture is subjected to ligation reaction using a DNA ligation kit. Thereby, a recombinant plasmid containing the modified D sequence of SEQ ID NO: 12 (hereinafter referred to as "plasmid pBluescript-DNA-D") can be constructed.

The so obtained recombinant plasmid, pBluescript-DNA-D, is introduced into *E. coli* XLI-Blue MRF'. The resulting transformant (hereinafter referred to as *Escherichia coli* XL1-Blue MRF'/pBluescript-DNA-D) is cultured in a liquid medium to give a large number of transformant cells. The *E. coli* cells thus proliferated are containing copies of the above recombinant plasmid pBluescript-DNA-D. The modified D sequence can be cloned in this manner. A plasmid containing the modified D sequence is isolated from the cultured *E. coli* cells by means of ordinary extraction.

(5) Recovery of a DNA Fragment Carrying the Modified D Sequence

The plasmid containing the modified D sequence as obtained in the above (4) is then digested with the restriction enzyme EcoRI.

This treatment gives a reaction mixture containing a DNA fragment which is carrying the modified D sequence and which is having the nucleotide sequence ATG at the 5' end adjacent to the EcoRI cleavage site and also having an extended part containing an EcoRI cleavage site at the 3' end.

The above reaction mixture is fractionated by low-melting point agarose electrophoresis, and a band containing the above DNA fragment is cut out of the agarose gel. The obtained agarose gel piece is dissolved in TE buffer. The resulting solution is extracted with phenol, whereby the above DNA fragment is recovered as an extract. The phenol extract containing the above DNA fragment is mixed with a 3 M aqueous solution of sodium acetate and ethanol. The resulting mixture is allowed to stand at 20° C. about 6 hours and then centrifuged at a low temperature, whereby the above DNA fragment is precipitated. By drying the precipitate, the desired DNA fragment which carries the modified D sequence, is obtained as powder. This powdery DNA fragment carrying the modified D sequence is soluble in water.

Described above is a process for preparing the DNA fragment carrying the modified D sequencer which is an example of the DNA of the third aspect of the present invention, by utilizing the recombinant DNA techniques. However, the desired DNA can also be prepared by a known method for the chemical synthesis of polynucleotides, with referring to the nucleotide sequence shown in SEQ ID NO: 12 of Sequence Listing.

The foregoing are explanations of the mode for carrying out the third aspect of the present invention, in respect of such case when the modification is made to effect the "guanine to adenine change" at the nucleotide 967 in the sequence of the DNA of the first aspect of the present invention shown in SEQ ID NO: 1. It is also possible to prepare another modified DNA which contains a nucleotide substitution at a position different from the nucleotide 967 in the sequence of the DNA of the first aspect of the present invention shown in SEQ ID NO: 1, if the use of the DNA shown in SEQ ID NO: 1 is made as the template and then a combination of several synthetic oligonucleotides having appropriately designed nucleotide sequences is used as the primers.

We, the present inventors have made further studies. As a result, we have now found that both of the novel DNA of the first aspect of the present invention which encodes the α-subunit of the first isozyme of rice ASA, as well as the novel modified DNA of the third aspect of the present invention which is derived from the DNA encoding the α-subunit of the first isozyme of rice ASA can be introduced into a plant, when the novel DNA of this invention is incorporated in a recombinant vector, and also that the novel DNA can be expressed in the plant. To this end, there may be utilized the known techniques in biotechnology for the transformation of a plant, which comprise introduction of an exogenous gene and expression of the exogenous gene in the resultant transgenic plant.

Accordingly, the fifth aspect of the present invention provides a transformed plant, characterized by having a plant cell as transformed by introduction of such a recombinant vector which carries the DNA of the first aspect of the present invention for encoding the α-subunit of the first isozyme of rice anthranilate synthase; said DNA as introduced being capable of expression therein.

The sixth aspect of the present invention provides a transformed plant, characterized by having a plant cell as transformed by introduction of such a recombinant vector which carries carrying the DNA of the third aspect of the present invention for encoding a protein having the activity of the α-subunit of the first isozyme of rice anthranilate synthase but being insensitive to the feedback inhibition by tryptophan, and particularly, such a recombinant vector which carries the DNA for encoding the protein having the amino acid sequence shown in SEQ ID NO: 13 or the DNA having the nucleotide sequence shown in SEQ ID NO: 12 and, said DNA as introduced can be expressed therein.

Further, it has been found that when the transformed plant according to the fifth or sixth aspect of the present invention is a plant capable of producing seeds by culturing, seeds of said transformed plant can be harvested by culturing said plant under ordinary conditions.

Accordingly, the seventh aspect of the present invention provides seeds of a transformed plant which are harvested from culturing of transformed plant which is produced by introducing such a recombinant vector carrying the DNA of the first aspect of the present invention for encoding the α-subunit of the first isozyme of rice anthranilate synthase, or such a recombinant vector carrying the modified DNA of the third aspect of the present invention, into a plant cell, and in which transformed plant said DNA can be expressed.

The eighth aspect of the present invention provides a recombinant vector which comprises an inserted DNA fragment carrying the DNA sequence having the nucleotide sequence shown in SEQ ID NO: 1 or 10 of Sequence Listing, and which vector is capable of expressing said DNA sequence in a host cell.

The ninth aspect of the present invention provides a recombinant vector which comprises an inserted DNA fragment carrying such DNA sequence as named the modified D sequence having the nucleotide sequence shown in SEQ ID NO: 12 of Sequence Listing, and which vector is capable of expressing said DNA sequence in a host cell.

The tenth aspect of the present invention provides, as a novel microorganism, *E. coli* as transformed with such a recombinant vector which comprises an inserted DNA fragment carrying the DNA sequence having the nucleotide sequence shown in SEQ ID NO: 1 or 10 of Sequence Listing, and which vector is capable of expressing said DNA sequence in a host cell.

The eleventh aspect of the present invention provides, as a novel microorganism, *E. coli* as transformed with such a recombinant vector which comprises an inserted DNA fragment carrying the DNA sequence as named the modified D sequence having the nucleotide sequence shown in SEQ ID NO: 12 of Sequence Listing, and which vector is capable of expressing said DNA sequence in a host cell.

By proliferating the *E. coli* transformant according to the tenth aspect of the present invention, or the *E. coli* according to the eleventh aspect of the present invention, a large number of clones of the recombinant vector contained in the cells can be harvested. Examples of the *E. coli* according to the tenth aspect of the present invention include the above-mentioned *Escherichia coli* XL1-Blue MRF' (OS-asa-1) and *Escherichia coli* XL1-Blue MRF' (OS-asa-2), which have been deposited under the Budapest Treaty with accession numbers FERM BP-6453 and FERM BP-6454, respectively.

An example of the *E. coli* transformant according to the eleventh aspect of the present invention is the above-mentioned *Escherichia coli* XL1-Blue MRF'/pBluescript-DNA-D, which has been deposited under the Budapest Treaty with accession number FERM BP-6451.

The DNA according to the first aspect of the present invention and the DNA according to the third aspect of the present invention can be used as the exogenous genes for making the transformation of a wide variety of plants. Introduction of the DNAs of the present invention as the exogenous genes into plants for the transformation can be carried out by known techniques in biotechnology.

Outlined below is the process described in Example 3 which can be suitably employed for the introduction of the DNA according to the first or third aspect of the present invention, as an exogenous gene into rice plants.

(a) Construction of Recombinant Vectors for Introduction of Exogenous Genes

A known plasmid vector pUBA [Plant Molecular Biology, vol. 18, no. 4, pp. 675–689 (1992)], which contains the known maize ubiquitin promoter, 1st intron and NOS terminator as well as a phosphinothricin resistance gene and an ampicillin resistance gene capable of expressing its effect only in microorganisms, is treated with the restriction enzymes BamHI and SacI in a buffer. This treatment gives such a vector fragment of about 4.8 kb which has been cleaved at the BamHI cleavage site located downstream of the ubiquitin promoter and downstream of the 1st intron and also cleaved at the SacI cleavage site located upstream of the NOS terminator.

An aqueous solution of the so obtained vector DNA fragment is mixed with an aqueous solution of a DNA fragment carrying the DNA of the present invention. The resultant mixture is subjected to ligation reaction by using a DNA ligation kit. This reaction results in the construction of a recombinant vector containing the DNA fragment carrying the DNA of the present invention which is inserted between the ubiquitin promoter and the NOS terminator region of the vector DNA fragment.

The thus constructed recombinant vector is introduced into *E. coli* JM109, to obtain an *E. coli* transformant.

The obtained *E. coli* transformant is inoculated into a medium containing the antibiotic ampicillin and cultured, whereby several ampicillin-resistant *E. coli* colonies are obtained. These colonies are separately proliferated in a medium containing ampicillin.

Plasmids are isolated from the proliferated ampicillin-resistant *E. coli* cells of the respective colonies. The plasmids thus recovered include various plasmids, wherein the DNA is inserted in different orientations. The plasmids as recovered from the respective colonies are digested with appropriate restriction enzymes. The resulting reaction mixtures containing various DNA fragments resulting from the digestion are subjected to agarose gel electrophoresis. By analysis of the size and nucleotide sequence of these DNA fragments, there can be selected appropriate plasmids (about 6.5 kb) wherein the DNA of the present invention is inserted downstream of the ubiquitin promoter of the recombinant plasmid in the normal orientation.

The plasmid, wherein the DNA of the first aspect of the present invention shown in SEQ ID NO: 1 is incorporated, is named as vector pUBdW1; and the plasmid, wherein the DNA of the second aspect of the present invention shown in SEQ ID NO: 10 is incorporated is named as vector pUBdW2; and the plasmid, wherein the DNA of the modified D sequence shown in SEQ ID NO: 12 is incorporated, is named as vector pUBdD.

Further, for effecting the preparation of a recombinant vector for Use in the gene introduction according to the Agrobacterium method; a known plasmid vector pIG121-Hm [Plant Cell Physiol., vol. 31, pp. 805–813 (1990)] containing a hygromycin resistance gene is treated with the restriction enzymes PmeI and SacI in a buffer, thereby to obtain a vector fragment of about 9.8 kb.

Each of the above plasmid vectors pUBdW1, pUBdW2 and pUBdD is treated with SphI and SacI in a buffer, followed by the treatment for blunting the SphI-cleaved end, and there is afforded a vector fragment in which the DNA of the present invention is ligated downstream of the ubiquitin promoter and the 1st intron.

Ligation reaction, production of E. coli transformants and recovery of plasmids are carried out in the same manner as described above, with using the above vector fragments carrying the DNA of the present invention. Thereby, their can be obtained the recombinant vectors for the gene introduction according to the Agrobacterium method in which the DNA of the present invention is inserted in the normal orientation.

The plasmid, wherein the DNA of the first aspect of the present invention shown in SEQ ID NO: 1 is incorporated, is named as vector pUb-OSASAW1; and the plasmid, wherein the DNA of the second aspect of the present invention shown in SEQ ID NO: 10 is incorporated, is named as vector pUb-OSASAW2; and the plasmid, wherein the DNA of the modified D sequence of the third aspect of the present invention shown in SEQ ID NO: 12, is incorporated, is named as vector pUb-OSASA1D.

(b) Preparation of Rice Callus

After mature seeds of rice are hulled, the resulting rice seeds with coats are sterilized with an ethanol solution and then with a dilute aqueous solution of sodium hypochlorite, followed by washing with sterilized water.

The rice seeds with coats are placed on such a callus formation medium as prepared by adding sucrose, 2,4-PA as a phytohormone and agar to MS medium. Cultivation of seeds is carried out at 28° C. for 40–50 days with irradiation with sunlight at 1500–2500 lx for 15–18 hours per day, affording callus. The callus thus formed are cut from the albumen of the seeds.

(c) Introduction of an Exogenous Gene into Rice Callus Cells

In order to introduce the recombinant vector carrying the normally inserted DNA of the present invention which has been prepared by the method described in the above (a) (i.e. the above-mentioned vector pUb-OSASAW1, pUb-OSASAW2 or pUb-OSASA1D) into callus cells according to the known Agrobacterium method, the recombinant vector is first introduced into Agrobacterium tumefaciens as a host according to the known electroporation technique [Shokubutsu Soshiki Baiyo (Plant Tissue Culture), vol. 10, no. 2, pp. 194–196 (1993)].

The DNA of the present invention can be introduced into rice callus cells by co-cultivation of the thus obtained Agrobacterium with the callus cells as obtained in the above (b), according to a known method [Saibo Kogaku (Cell Engineering), suppl. vol. "Protocol for Experiments Using Model Plants", pp. 93–98 (1996) published by Shujunsha]. Hygromycin-resistant plant cells as transformed with the DNA of the present invention are thus obtained.

(d) Reselection of Transformed Plant Cells

From the hygromycin-resistant transformed plant cells obtained as above are reselected such transformed plant cells containing a sufficiently effective amount of the DNA of the present invention as the exogenous gene.

To this end, the transformed cells obtained as above are transplanted to a reselecting medium which has been prepared by adding sucrose, 2,4-PA, Gel lite and a tryptophan analogue 5MT (5-methyltryptophan) to N6 medium.

The transplanted cells are cultured there at 25–28° C. for 25–30 days with irradiation with light at 2000 lx for 16 hours per day.

The transformed plant cells, which contain a sufficiently effective amount of the DNA of the present invention as the exogenous gene, are resistant to 5MT, and they can grow on a medium containing 5MT which acts as a cell growth inhibitor. The cultured plant cells, which are resistant to 5MT grown on the above 5MT-containing medium, are selected in this way.

(e) Plant Regeneration from 5MT-Resistant Transformed Plant Cells Reselected

The 5MT-resistant cultured plant cells as reselected in the above manner are then transplanted to a differentiation medium for plant regeneration which has been prepared by adding sucrose, benzyladenine as a phytohormone, naphthaleneacetic acid and Gerite to MS medium for plant tissue culture.

The transplanted cells are then cultured at 25–28° C. for 25–30 days with irradiation with light at 2000 lx for 16 hours per day, whereby buds and roots can be regenerated from the cultured transformant plant cells by differentiation.

Plumules containing the regenerated buds and roots have grown to a length of 10–30 mm, and thereafter the plumules are transplanted to a habituation medium which has been prepared by adding sucrose and Gerite to MS medium. Cultivation is carried out at 25–28° C. for 18–20 days with irradiation with light at 2000 lx for 16 hours per day.

Transformed plants can be regenerated in this manner. The thus obtained transformed plants normally grow when they are transplanted into the soil in a greenhouse and are cultured under ordinary conditions. They can produce rice seeds after 3–6 months of cultivation.

(f) Confirmation of the Introduced Exogenous Gene

Green leaves are taken from the transformed rice plants as regenerated in the above manner The leaves are frozen in liquid nitrogen, followed by disruption. DNA is extracted from the disrupted leaves according to the method of J. Sambrook, et al. [Molecular Cloning, 2nd ed., Cold Spring Harbor Laboratory Press (1989)].

Separately, an oligonucleotide having the nucleotide sequence shown in SEQ ID NO: 14 of Sequence Listing, and an oligonucleotide having the nucleotide sequence shown in SEQ ID NO: 15, which are to be used as primers, are chemically synthesized.

PCR is carried out in the usual way with using the DNA extracted from the regenerated rice plants as above, as the template, and using the above two synthetic oligonucleotides as the primers in order to amplify the above DNA. The resulting amplification reaction mixture is fractionated by agarose electrophoresis in a conventional manner. A band containing a DNA fragment corresponding to the DNA of the introduced exogenous gene, among various DNA fractions derived from the DNA extracted from the regenerated rice plants, is cut out of the agarose gel.

It is possible to confirm whether the DNA fragment contained in the resultant band corresponds to the DNA of the present invention or not, by analyzing its nucleotide sequence by the known Southern analysis technique.

Extraction of tryptophan from plants and determination of tryptophan content of plants can be carried out by a known method [the Hopkins-Cole method, Seikagaku Jikken Koza (Lectures on Experiments in Biochemistry), vol. 11, published by Tokyo Kagaku Dojin], or by a method utilizing HPLC as described in the example given below. The procedures for the extraction of tryptophan and the determination of tryptophan content can be appropriately modified according to the kind, part and growth stage of a test plant.

The processes for the selection of cells as transformed by introduction of the DNA of the present invention and for the production of the transformed plants are described below.

(a) Construction of a Recombinant Vector for Selection

A recombinant vector, which is to be used for directly introducing a gene into a plant cell for the production of a transformed plant, is constructed in the following manner. That is, a known plasmid vector pBI221 (Clontech), which contains the known cauliflower mosaic virus 35S promoter and NOS terminator, as well as an ampicillin resistance gene cabafle of expressing its effect only in microorganisms, is treated with the restriction enzymes XbaI and SacI in a buffer. This treatment gives a vector fragment of about 3.8 kb which has been cleaved at the XbaI cleavage site located downstream of the 35S promoter and cleaved at the SacI cleavage site located upstream of the NOS terminator.

An aqueous solution of the obtained vector DNA fragment is mixed with an aqueous solution of a DNA fragment carrying the DNA of the third aspect of the present invention (the modified D sequence). The resulting mixture is subjected to ligation reaction by using a DNA ligation kit. This reaction results in the construction of a recombinant vector containing the DNA fragment which carries the DNA of the present invention (the modified D sequence) inserted between the 35S promoter and the NOS terminator region of the vector DNA fragment.

The thus constructed recombinant vector is introduced into *E. coli* JM109, to obtain an *E. coli* transformant.

The obtained *E. coli* transformant is inoculated into a medium containing the antibiotic ampicillin and is cultured, whereby several ampicillin-resistant *E. coli* colonies are obtained. These colonies are separately proliferated in a medium containing ampicillin.

Plasmids are isolated from the proliferated ampicillin-resistant *E. coli* cells of the respective colonies. The plasmids thus recovered include various plasmids wherein the DNA is inserted in different orientations. The plasmids as recovered from the respective colonies are digested with appropriate restriction enzymes. The resulting reaction mixtures containing various DNA fragments resulting from the digestion are subjected to agarose gel electrophoresis. By analysis of the size and nucleotide sequence of these DNA fragments, an appropriate plasmid (about 5.6 kb), wherein the DNA of the present invention (the modified D sequence) is inserted downstream of the 35S promoter of the recombinant plasmid in the normal orientation, can be selected. For the recombinant vector for selection and use in the production of a transformed plant, the above vector pUBdD can be employed in the case of the direct gene introduction into plant cells. The above vector pUb-OSASA1D can be employed in the case of the Agrobacterium method.

(b) Preparation of Rice Calluses

After mature seeds of rice are hulled, the resulting rice seeds with coats are sterilized with an ethanol solution and then with a dilute aqueous solution of sodium hypochlorite, followed by washing with sterilized water.

The rice seeds with coats are placed on a callus formation medium which has been prepared by adding sucrose, 2,4-PA as a phytohormone and agar to MS medium. Cultivation is carried out at 28° C. for 40–50 days with irradiation with sunlight at 1500–2500 lx for 15–18 hours per day, to afford callus. The callus thus formed are cut from the albumen of the seeds.

(c) Introduction of Recombinant Vectors usable for Selection into Rice Callus Cells The recombinant vector usable for the selection and carrying the normally inserted DNA of the present invention, which is prepared by the method described in the above (a), i.e. the vector pUBdD, is introduced into the callus cells by the known method for direct introduction with whiskers (Japanese Published Unexamined Patent Application No. . . . /98). The selecting recombinant vector pUb-OSASA1D is introduced into callus cells by the known Agrobacterium method [Saibo Kogaku (Cell Engineering), suppl. vol. "Protocol for Experiments Using Model Plants", pp. 93–98 (1996) published by Shujunsha].

(d) Selection of Transformed Plant Cells

The callus cells which are containing the recombinant vector usable for selection and which are obtained as above, are added onto and evenly spread over a selecting medium prepared by adding sucrose, 2,4-PA, Gerite and a tryptophan analogue as a selective drug in an amount of 10 mg/1–200 mg/l, preferably 30 mg/1–50 mg/l, to N6 medium. Cultivation is carried out at 25–28° C. for 20–60 days, preferably 25–30 days, in a dark place or with irradiation with light at 2000 lx for 16 hours per day.

Plant cells as transformed with the recombinant vector usable for selection, which are resistant to the tryptophan analogue, are thus selected.

(e) Selection of Transformed Plants

In order to obtain the target transformed plants from the resulting tryptophan-analogue-resistant and transformed plant cells obtained as above, these transformed plant cells are transplanted to such a selective differentiation medium for plant regeneration which has been prepared by adding sucrose, benzyladenine as a phytohormone, naphthaleneacetic acid, Gerite and a tryptophan analogue as a selective drug in an amount of 10 mg/1–200 mg/l, preferably 30 mg/1–50 mg/l, to MS medium.

The transplanted plant cells are cultured at 25–28° C. for 25–30 days with irradiation with light at 2000 lx for 16 hours per day. Thereby, buds and roots can be regenerated from the cultured transformant plant cells, by differentiation.

Plumules containing the regenerated buds and roots have grown to a length of 10–30 mm, and then the plumules are transplanted to a habituation medium as prepared by adding sucrose and Gerite to MS medium. Cultivation is carried out at 25–28° C. for 18–20 days with irradiation with light at 2000 lx for 16 hours per day.

Transformed plants as intended can be regenerated in this manner.

The DNA according to the present invention can be introduced as an exogenous gene, not only into the above-mentioned rice plants but also into other kinds of plants for the transformation of them.

Further, the use of the DNA according to the present invention for the increase of tryptophan content and for the selection of appropriate rice plant is not limited to the above-mentioned rice plants, but it can be extended to other kinds of plants.

Given below are general descriptions of the process for introducing the DNA of the present invention into general plants, and of the process for increasing the tryptophan content, as well as of the process for selecting transformed cells and transformed plants.

There is no specific limitation to the kind of plants into which the DNA of the present invention can be introduced. Representative plants include monocotyledons such as rice, maize, wheat and barley, and dicotyledons such as tobacco, soybean, cotton, tomato, Chinese cabbage, cucumber and lettuce. It is convenient to first prepare the cultured cells from these plants and then introduce the DNA of the present invention as an exogenous gene into the cultured cells.

The cultured cells to be used for the introduction of the DNA of the present invention can be prepared from any explant derived from a plant. For example, such explants derived from scutellum, meristem, pollen, anther, lamina, stem, petiole and root can be used.

It is convenient to introduce the DNA of the present invention into the cultured cells obtained by cultivation of said explant on a callus formation medium, for example, a medium which is prepared by adding a phytohormone such as 2,4-PA (2,4-dichlorophenoxyacetic acid) in an amount of 0.1–5 mg/l, a carbon source such as sucrose in an amount of 10–60 g/l and Gerite in an amount of 1–5 g/l, to a medium for plant tissue culture containing inorganic salts and vitamins as essential components, e.g. MS medium [Murashige, et al. "Physiologia Plantarum" (1962), vol. 15, pp. 473–497], R2 medium [Ojima, et al. "Plant and Cell Physiology" (1973), vol. 14, pp. 1113–1121] or N6 medium [Chu, et al. (1978) "In Proc. Symp. Plant Tissue Culture, Science Press Peking", pp. 43–50].

Preferred plant cells, which are usable for the introduction of the DNA of the present invention, include dedifferentiated cultured cells such as callus and suspended cells, cultured cells such as adventitious embryo and shoot primordium, as well as callus cells and suspended cells prepared from cells of plant tissues such as leaf, root, stem, embryo and meristem.

In the process for preparing the cultured cells for the introduction of the DNA of the present invention by cultivation of an explant on a callus formation medium, there is no specific limitation to the cultivation time. However, in view of the necessity of regenerating a transformed plant, it is required that the plant regeneration from said cultured cells be permissible, namely, that the cultured cells be obtained within the period during which the plant cells can retain the capability for plant regeneration.

The cultured cells for the introduction of the DNA of the present invention can be the suspended cells as cultured in a liquid medium, so far as they are the cultured cells having retained the capability for plant regeneration.

In order to introduce the DNA of the present invention into a plant cell, it is necessary first to construct a recombinant vector by inserting the DNA of the present invention into an expression vector. The recombinant vector to be used here needs to have such a structure that the DNA of the present invention is located downstream of an expression promoter and a terminator is located downstream of said DNA, so that the DNA of the present invention can be expressed in a plant after being introduced therein. Useful recombinant vectors include various vectors which are employed for ordinary plant transformation according to the kind of methods for the introduction of DNA into plants. For example, plasmid vectors replicable in *E. coli*, such as pUC plasmids and pBR322 plasmids, are preferably used in the direct DNA introduction by the electroporation technique or the techniques utilizing particle gun or whisker. And, plasmid vectors such as plan plasmids are preferably used in the DNA introduction by the Agrobacterium method.

Examples of the promoters, which is to be located upstream of the DNA of the present invention in the recombinant vector, include CaMV35S derived from cauliflower mosaic virus [The EMBO Journal, vol. 16, pp. 3901–3907 (1987); Japanese Published Unexamined Patent Application No. 315381/94]; maize ubiquitin promoter (Japanese Published Unexamined Patent Application No. 79983/90); and phaseolin promoter [Plant Cell, vol. 1, pp. 839–853 (1989)]. Suitable terminator, which is to be located downstream of the DNA of the present invention, includes the terminator derived from cauliflower mosaic virus; and the terminator derived from a nopaline synthase gene [The EMBO J., vol. 6, pp. 3901–3907 (1987)]. Nevertheless, these can be used any of the promoters and terminators which function in plants.

In order to efficiently select such plant cells as transformed by the introduction of the DNA of the present invention, it is preferred to introduce into the plant cells the above recombinant vector together with a plasmid vector carrying an appropriate selective marker gen. Useful examples of the selective marker genes include a hygromycin phosphotransferase gene which is resistant to the antibiotic hygromycin; a neomycin phosphotransferase gene which is resistant to kanamycin and gentamicin; and an acetyltransferase gene which is resistant to the herbicide phosphinothricin [The EMBO Journal, vol. 6, pp. 2513–2518 (1987); Japanese Published Unexamined Patent Application No. 171188/90].

Representative methods for the introduction of the DNA of the present invention as an exogenous gene into plant cells are the Agrobacterium method [Bio/technology, vol. 6, pp. 915–922 (1988)]; electroporation [Plant Cell Rep., vol. 10, pp. 106–110 (1991)]; the particle gun method [Theor. Appl. Genet., vol. 79, pp. 337–341 (1990)]; and the whisker method. However, the DNA introduction techniques are not restricted to these methods.

In order to efficiently reselect the transformed cells containing a sufficiently effective amount of the recombinant vector carrying the DNA of the present invention, cultivation is carried out on a medium containing a tryptophan analogue which is a cell growth inhibitor.

An example of the tryptophan analogue is 5-methyltryptophan (5MT), which can be added to the reselecting medium to a concentration of 10 mg/l–1000 mg/l, preferably 20 mg/l–100 mg/l.

Plants are regenerated from the thus reselected transformed plant cells which are containing the recombinant vector carrying the DNA of the present invention inserted as the exogenous gene, as well as the vector carrying the selective marker. The plant regeneration can be carried out by a known method, for example, by cultivation of the transformed plant cells as reselected above on a known medium for the plant regeneration.

The transformed cells are placed on the medium for the plant regeneration and are cultured at 15–30° C., preferably 20–28° C., for 20–60 days, preferably 30–40 days, with irradiation with light at 500–2000 lx, preferably 800–1000 lx.

In this manner, a plant, which has been transformed by the introduction of the recombinant vector carrying the exogenous gene comprising the DNA of the present invention, can be regenerated from each plant cell.

The plants as regenerated from the transformed cells are then cultured on a habituation medium. After the habituation, the regenerated plants are grown in a greenhouse under ordinary conditions. By 3–6 months of cultivation in the greenhouse, the regenerated plants grow into maturation and become capable of producing seeds.

The presence of the introduced exogenous gene in the thus regenerated and cultured transformant plant can be confirmed by analyzing the nucleotide sequence of the DNA present in the plant, according to the known PCR and Southern analysis techniques [Southern, "J. Mol. Biol.", vol. 98, pp. 503–517 (1975)].

In the above analysis process, extraction of the DNA from the transformant plant can be carried out by the known method of J. Sambrook, et al. [Molecular Cloning, 2nd ed., Cold Spring Harbor Laboratory Press (1989)].

Upon effecting the analysis of the exogenous gene comprising the DNA of the present invention which is present in the regenerated plant, according to PCR, the DNA which has been extracted from the regenerated plant as described above is used as the template, and synthetic oligonucleotides having nucleotide sequences which are appropriately selected based on the nucleotide sequence of the DNA or the modified DNA of the present invention, are used as the primers. A mixture of said template and primers is added to a reaction mixture effecting for PCR and is subjected to the amplification reaction. In the amplification reaction procedure, DNA denaturation, annealing and extension reaction are repeated several tens of times, whereby the product of amplification of the DNA fragment carrying the DNA sequence of the present invention can be obtained.

The reaction mixture of PCR containing the amplification product is fractionated by means such as agarose electrophoresis to afford fractions of various DNA fragments amplified. A band containing such a DNA fragment, which is recognized to carry the DNA sequence corresponding to the DNA of the present invention a the introduced exogenous gene, is cut out of the agarose gel. By analyzing the nucleotide sequence of the DNA sequence in the DNA fragment contained in the obtained agarose gel piece according to the Southern analysis, it can be confirmed whether or not said DNA sequence corresponds to the DNA of the present invention.

Tryptophan analogues are useful as the selective drug for the selection of the transformed cells and for the selection of the transformed plants according to the present invention. Examples of such useful drugs include the tryptophan analogues as well as their biosynthetic intermediates such as 5-methyltryptophan (5MT), 4-methyltryptophan (4MT), 6-methyltryptophan (6MT), 7-methyltryptophan (7MT), 6-methylanthranilic acid (6MA), 5-methylanthranilic acid (5MA), 3-methylanthranilic acid (3MA), 5-fluoroanthranilic acid (5FA) and 6-fluoroanthranilic acid (6FA).

As described above, the novel DNA according to the third aspect of the present invention can be introduced as an exogenous gene into a plant or plant cell in order to cause the transformation of plant or plant cell which will give a plant or plant cell having an increased tryptophan content.

Accordingly, the twelfth aspect of the present invention provides a method of increasing the tryptophan content of a plant, which comprises: introducing a recombinant vector into a plant cell callus, such a recombinant vector wherein said recombinant vector carries the DNA of the third aspect of the present invention for encoding a protein which is insensitive to the feedback inhibition by tryptophan and which protein has the activity of the α-subunit of the first isozyme of anthranilate synthase, and particularly, the DNA encoding the protein having the amino acid sequence of SEQ ID NO: 13 or the DNA having the nucleotide sequence of SEQ ID NO: 12 of Sequence Listing and wherein said recombinant vector is capable of expressing said DNA in a plant; and thus obtaining a plant callus cell as transformed with said DNA; and regenerating a plant from said plant cell.

The thirteenth aspect of the present invention provides a method of selecting a transformed plant cell, which comprises: introducing a recombinant vector into plant cells to confer or said plant cells the resistance to such a tryptophan analogue that can inhibit the growth of plant cells, wherein said recombinant vector carries the DNA of the third aspect of the present invention for encoding the protein which is insensitive to the feedback inhibition by tryptophan and which protein has the activity of the α-subunit of the first isozyme of anthranilate synthase, and wherein said recombinant vector carries particularly the DNA which encodes the protein having the amino acid sequence of SEQ ID NO: 13 or the DNA having the nucleotide sequence of SEQ ID NO: 12 of Sequence Listing, and wherein said recombinant vector further carries an antibiotic resistance gene and said recombinant vector is capable of expressing said DNA in a plant; and then selecting such transformed which express the resistance to said tryptophan analogue.

The fourteenth aspect of the present invention provides a method of producing a transformed plant having an increased tryptophan content, which comprises: introducing a recombinant vector into plant cells to confer on said plant cells the resistance to the tryptophan analogue that can inhibit the growth of plant cells, wherein said recombinant vector carries the DNA of the third aspect of the present invention for encoding the a protein which is insensitive to the feedback inhibition by tryptophan and which protein has the activity of the α-subunit of the first isozyme of anthranilate synthase, and wherein said recombinant vector carries particularly the DNA for encoding the protein having the amino acid sequence of SEQ ID NO: 13 or the DNA having the nucleotide sequence of SEQ ID NO: 12 of Sequence Listing, and wherein said recombinant vector further carries an antibiotic resistance gene and said recombinant vector is capable of expressing said DNA in a plant; selecting such transformed cells which express the resistance to said tryptophan analogue; and regenerating plants from the thus selected transformed cells.

We, the present inventors have made further studies with the purpose of isolating such a promoter DNA which is useful for the expression of the gene encoding the α-subunit of the first isozyme of rice ASA. As a result, we have now succeeded in obtaining a DNA fragment carrying a promoter DNA sequence which is effective for the expression of the gene encoding the α-subunit of the first isozyme of rice ASA, according to the following procedure. Outlined below are the steps for obtaining said DNA fragment. (A detailed description of the procedure is given in Example 5 hereinafter.)

(a) Preparation of Rice Genomic DNA

Genomic DNA is extracted from tissues, e.g. stems and leaves, roots and calli, preferably stems and leaves or callus, of rice (*Oryza sativa*) by a conventional method. After removal of contaminants such as proteins, the genomic DNA is further purified by ultracentrifugation.

(b) Preparation of Rice Genomic DNA Fragments

The purified genomic DNA obtained as above is partially digested with the restriction enzyme EcoRI, and the digestion product is subjected to agarose gel electrophoresis. The thus fractionated DNA fragments are transferred to a nylon membrane High Bond N, followed by denaturation to fix the DNA fractions on the membrane.

Each DNA fraction as fixed on the membrane is then subjected to the hybridization reaction with the DIG-labeled probe DNA as prepared from Arabidopsis as in Example 1(5) below. Thereby a DNA fragment emitting the signal can be detected at a DNA size of about 6 kb on the membrane. Such DNA fraction in the agarose gel which is corresponding to this DNA fraction emitting the signal, is partially digested with the restriction enzyme RcoRI in the agarose gel and then cut out of the gel. The thus obtained DNA is purified, and the resulting purified product of the DNA fragment a is dissolved in TE buffer, to obtain fractionated genomic DNA.

(c) Construction of Rice Fractionated Genomic DNA Library

The so obtained genomic DNA fractions are ligated into a phage vector. The resulting recombinant vectors are packaged in a λ phage. Incubation of *E. coli* cells as infected with the resultant recombinant λ phages is then made to give a large number of the recombinant λ phages, which can be utilized as a fractionated genomic DNA library of rice.

(d) Selection of a Promoter Gene from the Rice Genomic DNA Library

A recombinant phage carrying a DNA sequence corresponding to the promoter gene for the rice ASA gene can be obtained when the above recombinant phages as constructed as the rice genomic DNA library is subjected to screening by the plaque hybridization with utilizing the DIG-labeled probe DNA which has been prepared from Arabidopsis in Example 1(5). As a result of such screening, we have fortunately succeeded in harvesting three phage plaques presumably carrying the promoter gene for the ASA gene, from one hundred thousand phage plaques of said rice genomic DNA library.

These three plaques as harvested are separately digested with the restriction enzyme RcoRI, to give reaction mixtures which are respectively containing EcoRI-digested DNA fragments.

(e) Cloning of Genomic DNA

The EcoRI-digested DNA fragments obtained as above are then ligated into the EcoRI cleavage site of the plasmid vector pBluescript II SK(+). The resulting recombinant plasmid vectors are introduced into *E. coli* for cloning, followed by isolation of the recombinant plasmid vector clones from *E. coli*.

(f) Sequence Analysis of Cloned Plasmid DNA

The recombinant plasmid vector clones obtained as above are then digested with the restriction enzymes RcoRI and BamHI, followed by effecting the nucleotide sequence analysis of the resulting EcoRI-BamHI fragments.

From the genomic DNA clones obtained above could be isolated such a DNA fragment carrying the DNA sequence of the promoter region which acts for the expression of the gene encoding the α-subunit of the first isozyme of rice ASA (said DNA fragment is provisionally referred to as "DNA fragment Z"), with reference to its nucleotide sequence.

The entire nucleotide sequence of the thus obtained "DNA fragment Z" carrying the promoter DNA was determined by means of an ordinary sequencing kit. The so determined sequence was recognized to be the nucleotide sequence shown in SEQ ID NO: 3 of Sequence Listing The promoter DNA carried by this DNA fragments was recognized to have the nucleotide sequence shown in SEQ ID NO: 7 of Sequence Listing, by referring to the known nucleotide sequence of the DNA of the promoter region of the gene which encodes the α-subunit of the first isozyme of Arabidopsis.

It was confirmed by the test of Example 5 that the entire or partial nucleotide sequence of the "DNA fragment Z" had a promoter activity.

The DNA fragment Z carrying the promoter DNA having the nucleotide sequence of SEQ ID NO: 7 was cloned in pBluescript II SK(+) plasmid vector. The resulting recombinant vector was introduced into *E. coli* XLI-Blue MRF'. The obtained *E. coli* transformant was named *Escherichia coli* (Os-asa#7), and it was deposited with the National Institute of Bioscience and Human-Technology, Agency of Industrial Science and Technology on Aug. 18, 1997 with accession number FERM P-16387 and also on Aug. 7, 1998 under the Budapest Treaty with accession number FERM BP-6452.

(g) Promoter Activity Test

The promoter activity test is now carried out for such promoter region of the gene encoding the α-subunit of the first isozyme of ASA, which is carried by the above DNA fragment Z as isolated from the said rice genomic DNA clone in the above, in order to confirm that it can function as a promoter. Thus, the above DNA fragment Z was inserted into a restriction enzyme cleavage site of the commercially available pBI101 plasmid vector (Clontech) carrying β-glucuronidase gene, which is a reporter gene. There was constructed a recombinant plasmid vector. This recombinant plasmid vector was introduced into plant cells, e.g. rice cultured cells, by a conventional method. It can be confirmed that said promoter region is effective to achieve the expression of the GUS activity, when using a commercially available GUS activity determination kit.

The fifteenth aspect of the present invention provides a DNA which has the nucleotide sequence shown in SEQ ID NO: 7 of Sequence Listing and has a promoter activity for the expression of the rice anthranilate synthase gene.

The sixteenth aspect of the present invention provides a DNA which has the nucleotide sequence shown in SEQ ID NO: 3 of Sequence Listing and comprises a DNA region having a promoter activity for the rice anthranilate synthase gene, as well as the exon DNA sequences and the intron DNA fragment for said DNA region having the promoter activity.

It is widely recognized in the art that even when one to several nucleotides in the nucleotide sequence of DNA having the promoter activity are deleted, substituted, inserted or added, the resulting modified sequence sometimes retains the promoter activity.

The DNAs according to the fifteenth and sixteenth aspects of the present invention can include such DNA fragments which result from such modifications and express the promoter activity in plant cells and plants. Namely, the fifteenth aspect of the present invention includes within the scope such modified DNA having the promoter activity and having a nucleotide sequence as formed by modification of the nucleotide sequence shown in SEQ ID NO: 7, wherein said modification is made by deletion, substitution, insertion or addition of one to several nucleotides. Such modified DNA can be obtained when the nucleotide sequence of the promoter DNA of the present invention is modified by a method such as site-specific mutagenesis, so that amino acid residues at specific positions will be deleted, substituted or added. The promoter activity test can be carried out for the modified DNA in the same manner as above.

In accomplishing the present invention, the ASA isozyme α-subunit genes of the present invention and the promoter sequence for them were isolated from the cDNA library or the genomic DNA library, as described above. As the nucleotide sequence of the promoter DNA has been determined by the present invention as shoun in Sequence Listing, the promoter DNA can also be prepared by chemical synthesis, with reference to the nucleotide sequence shown in Sequence Listing. It is also possible to obtain the promoter DNA from a rice cDNA library or a rice chromosomal DNA library by the known PCR when using a synthetic oligonucleotide primer as prepared based on the above-mentioned nucleotide sequence.

BEST MODE FOR CARRYING OUT THE INVENTION

Figure 1:
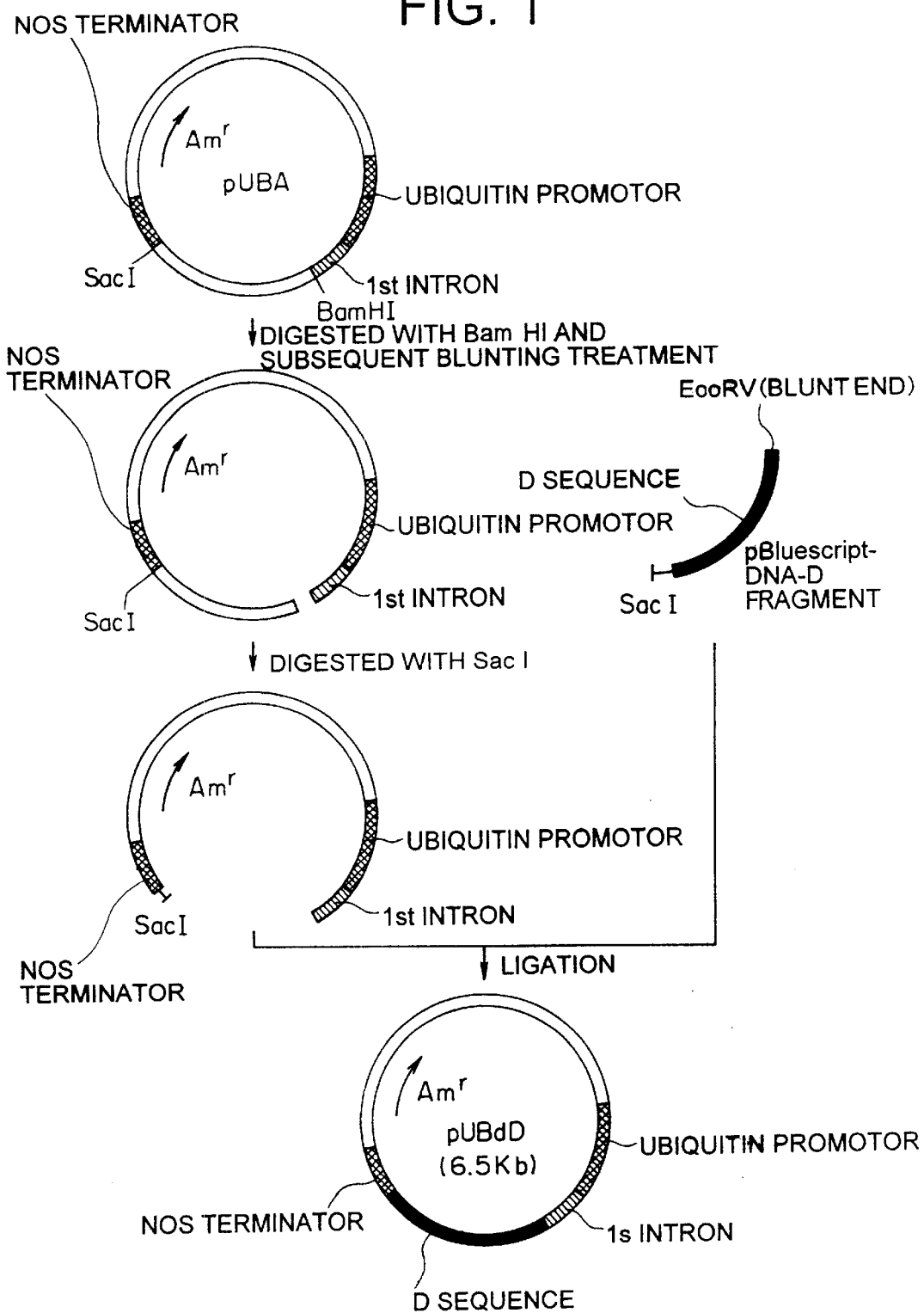
FIG. 1 is a schematic illustration of the process employed in Example 3(1) wherein there was constructed from the vector pUBA, the recombinant vector pUBdD which is a recombinant vector for the exogenous gene introduction used for transforming rice callus cells by direct introduction of an exogenous gene according to the whisker method, and which vector pUBdD carries the modified D sequence as provided by the third aspect of the present invention and having the nucleotide sequence of SEQ ID NO: 12.

The present invention will be further described by reference to the following examples, which are not intended to be limiting.

The procedures taken in the following Examples were carried out according to the methods as described in "Molecular Cloning", 2nd ed. by J. Sambrook, et al., Cold Spring Harbor Laboratory Press (1989), unless otherwise specified.

EXAMPLE 1

This Example illustrates a process for isolating the gene which encodes the α-subunit of the first isozyme (ASA1) of rice anthranilate synthase (ASA), as well as the gene which encodes the α-subunit of the second isozyme of ASA (ASA2).
(1) Preparation of Rice mRNA Seeds of rice (variety: Nihonbare) were sown, and on the 7th day of cultivation, 2 g of stems and leaves was taken from the rice plants in the juvenile form and frozen in liquid nitrogen. The frozen stems and leaves were disrupted in a mortar, and then about 2 mg of total RNA was extracted therefrom by the known AGPC method (the method using Acid Guanidinium thiocyanate-phenol-chloroform) [Experimental Medicine, Vol. 9, No. 15 (November issue), pp. 99–102 (1991)]. From the thus obtained total RNA were isolated the mRNAs by using an mRNA purification kit (mRNA Purification Kit, Pharmacia Biotech). In this manner, about 30 μg of rice mRNAs was obtained.
(2) Construction of Rice cDNA Library Rice cDNAs were produced from the rice mRNAs as obtained in (1) above, by using a DNA synthesis kit (TimeSaver cDNA Synthesis Kit, Pharmacia Biotech).

The cDNAs were ligated into a phage vector, i.e. such λgt11 phage vector, whose the EcoRI-cleaved end had been treated with alkaline phosphatase derived from calf small intestines (Lambda gt11/EcoRI/CIAP-Treated Vector Kit, STRATAGENE). The obtained recombinant vectors were packaged in a lambda phage by using an in vitro packaging kit (Gigapack II Gold Packaging Extract).

By conducting the incubation of E. coli Y1088 as infected with the recombinant lambda phages in which the recombinant vectors were packaged, there was obtained the above recombinant lambda phages in large numbers as the proliferated E. coli plaques. The recombinant lambda phages present in these plaques comprised such various phages containing total rice-derived cDNAs. These various phages were then utilized as a rice cDNA library.

(3) Construction of Primers for PCR

Primers were designed in order to prepare the DNA probes for PCR which are to be used for the cloning of cDNA fragments respectively encoding the α-subunits of the first isozyme (ASA1) and the second isozyme (ASA2) of rice anthranilate synthase (ASA). Two kinds of oligonucleotides having the following nucleotide sequences were prepared as primer No. 1 and primer No. 2 by chemical synthesis, with referring to the known nucleotide sequences and amino acid sequences of the genes which respectively encode the α-subunits of the first and second isozymes of Arabidopsis (Japanese name: shiroinunazuna) anthranilate synthase.

Primer No. 1 (oligonucleotide having the nucleotide sequence of SEQ ID NO: 8):
5'-CATATGTCTTCCTCTATGAAC-3'

Primer No. 2 (oligonucleotide having the nucleotide sequence of SEQ ID NO: 9):
5'-GGATCCTCATTTTTTCACAAATGC-3'

The above two oligonucleotides were prepared by synthesizing the oligonucleotides by the use of a DNA synthesizer (Model 391, Applied Biosystems), followed by purification of them by ion exchange HPLC.
(4) Preparation of Probe DNAs The thus constructed two synthetic oligonucleotides (10 p. M each) were used as the first primer and the second primer, respectively. 1 μl of a commercially available Arabidopsis cDNA library (STRATAGENE) was used as the template. The first and second primers and the Arabidopsis cDNA library were added to 50 μl of an amplification reaction mixture for effecting PCR [10 mM Tris-HCl (pH 8.3), 1.5 mM $MgCl_2$, 50 mM KCl, 0.001% gelatin, pH 8.3; a mixture of four kinds of nucleotide dNTP (2.5 mM each) and 2.5 units of DNA polymerase Takara Ex Taq], and the amplification reaction was carried out. The above amplification reaction mixture was prepared by using a PCR kit (PCR Amplification Kit, Takara Shuzo Co., Ltd.).

The above DNA amplification reaction by PCR was carried out by repeating 35 times a reaction cycle which consisted of denaturation at 94° C. for 30 seconds, annealing at 55° C. for one minute and extension at 72° C. for 2 minutes, with using a PCR reaction apparatus (DNA Thermal Cycler 480, PERKIN ELMER).

The above PCR procedure results in the formation of the products of the amplification of such DNA fragments which are parts of the DNA sequences corresponding to the genes encoding the α-subunits of the two isozymes of Arabidopsis ASA. The amplification products thus formed were recovered as probe DNAs and then were used in the cloning with using the rice cDNA library, as described below.
(5) Selection of DNAs of the Genes Encoding the α-Subunits of the Two Isozymes (ASA1 and ASA2) of Rice ASA from Rice cDNA Library The recombinant lambda phages, which had been constructed as the rice cDNA library in the above (2), were subjected to the screening by the plaque hybridization with using the probe DNAs as prepared from the Arabidopsis DNA library in the above (4). There was thus obtained such recombinant lambda phages which carry the DNA sequences corresponding to the genes encoding the α-subunits of the two isozymes of rice ASA.

In the first step of the screening, plaques of the recombinant lambda phages which are the rice cDNA library as obtained in the above (2) were formed on a 1.5% agar medium. The resultant phage plaques were transferred to nylon membranes (High Bond N, Amersham). The phage DNAs contained in said phage plaques as transferred to the nylon membranes were then treated with an alkaline denaturation solution (comprising 1.5 M NaCl and 2.0M NaOH) and with a neutralization solution (comprising 1.0 M Tris-HCl, pH 5 and 2.0 M NaCl) for 10 minutes each, followed by treating with UV irradiation so as to fix the phage DNAs on the nylon membranes.

Then, labeled probe DNAs were prepared by labeling the probe DNAs as obtained from the Arabidopsis cDNA library in the above (4), with digoxigenin (DIG). The labeled probe DNAs were used for plaque hybridization of the above phage DNAs (i.e. rice cDNA library) as fixed on the nylon membranes. The labeling of the probe DNAs was carried out by using DIG-ELISA DNA Labeling & Detection Kit (Boehringer Mannheim).

The above plaque hybridization was carried out in such a way that the nylon membranes having the above phage DNAs fixed thereon was soaked in a hybridization solution (comprising 500 mM Na-Pi buffer, pH 7.2, 7% SDS, 1 mM EDTA) at 65° C. for 10 minutes, followed by adding the above DIG-labeled probe DNAs (10 ng/ml) thereto, and incubating the membranes at 65° C. for 15 hours.

After the completion of reaction, the nylon membranes were washed with a washing solution (comprising 40 mM NaPi buffer, pH 7.2, 1% SDS) three times for 20 minutes each, followed by conducting the detection of the desired recombinant phages carrying the DNAs encoding the rice ASA α-subunits, by means of the above DIG-ELISA Labeling & Detection Kit. As a result, such eight recombinant phage plaques which hybridized and emitted a strong signal on an X-ray film, that is, such eight phage plaques which were considered to carry therein the genes encoding rice ASA, could be detected from among the three hundred thousand phage plaques presented on the nylon membranes. The above eight recombinant phage plaques carrying the rice ASA genes were thus selected and isolated.

Then, λ DNA was isolated from each of said isolated eight recombinant phage plaques, by using a λ DNA isolation kit (Lambda DNA Purification Kit, STRATAGENE).

The isolation of λ DNA was carried out in the following manner. The phages of the said eight plaques were separately proliferated in large numbers. To 5 ml of each of the resulting culture broths were added 50 μl of DNase I (20 mg/ml) and 200 μl of RNase A (2 mg/ml). Each of the resultant mixture was allowed to stand at room temperature for 15 minutes. The resulting proliferated phage solution was centrifuged at 15000 rpm at 4° C. for 10 minutes, and then 25 ml of 80% DEAE-cellulose was added to the supernatant, followed by effecting the incubation at room temperature for 10 minutes. After the incubated mixture was centrifuged, 2 ml of 0.5 M EDTA and 770 μl of Pronase (50 mg/ml) were added to the supernatant. The resultant mixture was allowed to stand at 37° C. for 15 minutes. To this mixture was further added 1.5 ml of 5% CTAB solution [1% CTAB (Cetyltrimethylammonium bromide), 50 mM Tris-HCl, pH 8.0, 10 mM EDTA]. After treatment at 65° C. for 3 minutes, the resulting mixture was allowed to stand in ice for 5 minutes. To the resulting reaction mixture were added a 1/10 volume of 3 M sodium acetate and a two-fold volume of ethanol, and then the mixture as obtained was allowed to stand at −20° C. for about 6 hours, followed by centrifugation. The so precipitated phage DNA was dried and then dissolved in 5 ml of water for storage.

By the above procedure, eight kinds of phage DNAs were isolated from the respective phage plaques. Then, 5 μl of each DNA was digested with 10 units of the restriction enzyme EcoRI in H buffer, followed by effecting the analysis of each digestion mixture.

When the cleavage of the phage DNAs of the phages selected as above was made with said EcoRI digestion in the above, there were afforded such DNA insert fragments in the phage DNAs which could be judged to carry the DNA sequences corresponding to the genes for encoding the α-subunits of the two isozymes of rice ASA.

(6) Cloning of cDNAs Carrying the DNA Sequences Corresponding to the Genes Encoding the α-Subunits of Two Isozymes (ASA1 and ASA2) of Rice ASA As described above, the eight kinds of the DNA insert fragments were obtained from the digestion of the above-mentioned eight kinds of recombinant phages, and they were the DNA fragments which were judged to carry the DNA sequences corresponding to the genes for encoding the α-subunits of the two isozymes of rice ASA. Each of these eight DNA fragments so obtained was inserted into the EcoRI cleavage site of the plasmid vector pBluescript II SK(+) by using a DNA ligation kit, so as to construct a recombinant plasmid vector. The thus constructed recombinant plasmid vector was introduced into *E. coli* XLI-Blue MRF' for the transformation.

The introduction of the recombinant plasmid vector into *E. coli* XLI-Blue MRF' for the transformation in the above was carried out in the following manner. That is, 10 μg of each of the recombinant phage DNA obtained above was digested with 10 units of the restriction enzyme EcoRI in H buffer, thereby to obtain a digestion mixture. Separately, 10 μg of the plasmid vector pBluescript II SK(+) was likewise digested with EcoRI, to obtain a digestion mixture. To each of the thus obtained DNA digestion mixtures were added a 1/10 volume of 3 M sodium acetate and a two-fold volume of ethanol. Each mixture so obtained was allowed to stand at −20° C. for about 6 hours, followed by centrifugation. The DNAs so precipitated from the respective DNA solutions were then separately dried and then dissolved in 5 μl of water. The resulting aqueous solution of the phage-derived DNA and the resulting aqueous solution of the plasmid-derived DNA (5 μl each) were mixed together. The resultant mixture was treated with DNA Ligation Kit (Takara Shuzo Co., Ltd.) to ligate the said two kinds of DNAs. To the resulting DNA-ligation mixture were added a 1/10 volume of 3 M sodium acetate and a two-fold volume of ethanol. After being allowed to stand at −20° C. for about 6 hours, the resultant mixture was centrifuged. The so precipitated DNA was dried. The resulting ligated vector DNA was thus recovered and then dissolved in 10 μl of water.

Then, 10 μl of the aqueous solution of the said ligated vector DNA (DNA 10 ng), as well as 100 μl of the commercially available *E. coli* XLI-Blue MRF' competent cells (STRATAGENE) were together put into a 1.5-ml tube, followed by the incubation in ice for 30 minutes, at 42° C. for 30 seconds and further in ice for 2 minutes. To the so incubated mixture was added 900 μl of SOC liquid medium (comprising 2% Bacto-tryptone, 0.5% Bacto-yeast extract, 10 mM NaCl, 2.5 mM KCl, 10 mM MgSO$_4$, 10 mM MgCl$_2$, 20 mM glucose), followed by shaking the resultant *E. coli* culture at 37° C. for one hour.

The above resulting *E. coli* culture (100 μl) was plated on LB agar medium (comprising 1% Bacto-tryptone, 0.5% Bacto-yeast extract, 0.5% NaCl, 0.1% glucose, pH 7.5, 1.5% agar) containing 50 mg/l ampicillin, 20 mg/l X-gal (5-bromo-4-chloro-3-indolyl-b-D-galactoside) and 20 mg/l IPTG (isopropyl-b-D-thiogalactopyranoside). After cultivation at 37° C. for 16 hours, the *E. coli* colonies showing a white coloration were selected and then isolated as the *E. coli* which was transformed with the recombinant plasmid vector DNA containing the DNA fragment as derived from the aforesaid recombinant phage.

The so isolated 10 colonies of the ampicillin-resistant *E. coli* transformant, which were showing a white coloration, were grown in a liquid medium containing 50 mg/l ampicillin. Plasmid DNA was then isolated from the so grown *E. coli* cells and purified by using a plasmid purification kit (QIA filter Plasmid Midi Kit, QIAGEN). By such purification, 50 μg (50 μl) of the recombinant plasmid DNA could be obtained from the ampicillin-resistant *E. coli* transformant colonies isolated in the above.

From the recombinant phages as isolated above (the eight kinds of the phages in total), eight kinds of recombinant plasmid DNAs were recovered by the cloning of said phages as described above. The nucleotide sequences of these eight kinds of the plasmid DNAs were analyzed in the following manner.

(7) Sequence Analysis of Cloned DNAs

The resultant recombinant plasmid DNAs, which are the eight kinds of DNAs as cloned in the above, were separately treated with a commercially available nucleotide sequence determination kit. Thereby, the entire nucleotide sequence of the plasmid DNA fragments was determined. As a result, could be identified the nucleotide sequences of such DNAs which are corresponding to the genes for encoding the α-subunits of rice ASA1 and ASA2, and which were carried by the said plasmid DNA fragments.

The above mentioned DNA-sequence determination was carried out by first denaturing the DNA by use of a nucleotide sequence determination kit (Autoread Sequencing Kit, Pharmacia Biotech), and then determining the nucleotide sequence with an automatic DNA sequencer (ALF DNA Sequencer II, Pharmacia).

The above determination of the nucleotide sequence of the above DNA fragments could reveal that the DNA sequences for encoding the rice ASA α-subunits are comprising two different nucleotide sequences. This indicates that rice ASA consists of two isozymes (isoenzymes), and that the nucleotide sequence of the DNA for encoding the α-subunit of the first isozyme (ASA1) is different from that of the DNA for encoding the α-subunit of the second isozyme (ASA2) of rice.

The DNA corresponding to the gene for encoding the rice ASA1 α-subunit was identified as described above, and said DNA was found to have the nucleotide sequence shown in SEQ ID NO: 1 of Sequence Listing given hereinafter.

The DNA corresponding to the gene for encoding the rice ASA2 α-subunit was identified as described above, and said DNA was found to have the nucleotide sequence shown in SEQ ID NO: 10 of Sequence Listing given hereinafter.

The nucleotide sequence of the DNA of the gene for encoding the rice ASA1 α-subunit according to the present invention consists of such 1734 nucleotides shown in SEQ ID NO: 1, which are within a single open reading frame set out in SEQ ID NO:1. The nucleotide sequence of the DNA of the gene for encoding the rice ASA1 α-subunit according to the present invention as shown in SEQ ID NO: 1 will encode the protein which consists of 577 amino acid residues shown in SEQ ID NO: 2 Sequence Listing. The amino acid sequence of SEQ ID NO: 2 shows a 68% homology to the known amino acid sequence of the Arabidopsis ASA1 α-subunit protein [The Plant Cell, vol. 4, pp.721–733 (1992)]; but it is clearly different from the amino acid sequence of the Arabidopsis ASA1 α-subunit in the other regions, and thus it shall be the particular sequence peculiar to rice.

The nucleotide sequence of the DNA of the gene for encoding the rice ASA2 α-subunit according to the present invention consists of such 1821 nucleotides shown in SEQ ID NO: 10, which are within a single open reading frame set out in Sequence Listing, SEQ ID NO: 1. The nucleotide sequence of the DNA of the gene for encoding the rice ASA2 α-subunit according to the present invention as shown in SEQ ID NO: 10 will encode the protein which consists of 606 amino acid residues shown in SEQ ID NO: 11. The amino acid sequence of SEQ ID NO: 11 shows a 72% homology to the known amino acid sequence of the Arabidopsis ASA2 α-subunit protein [The Plant Cell, vol. 4, pp. 721–733 (1992)], but it is clearly different from the amino acid sequence of the Arabidopsis ASA2 α-subunit in the other regions and thus it is the particular sequence peculiar to rice.

(8) Deposit of *E. coli* Transformants Carrying Rice ASA α-Subunit Genes

The procedure set out in the above (6) gave the eight kinds of recombinant plasmid DNAs as the end products. The entire nucleotide sequence of each DNA fragment of these eight recombinant plasmid DNAs was determined with using a nucleotide sequence determination kit in the above (7).

(i) Next, from the above-mentioned eight kinds of recombinant plasmid DNA fragments was selected such one recombinant plasmid DNA which was judged to carry the DNA sequence consisting of 1734 nucleotides shown in SEQ ID NO: 1 (named as DNA sequence OSASA-W1) (i.e. the DNA for encoding the rice ASA1 α-subunit). The so selected one recombinant plasmid DNA fragment was digested with the restriction enzyme EcoRI, and the digestion product was fractionated by low-melting point agarose electrophoresis, to obtain such a DNA fragment which was judged to carry the DNA sequence OSASA-W1 (and which DNA fragment was named as DNA sequence OSASA-1). The thus obtained DNA sequence OSASA-1 was ligated into the EcoRI cleavage site of the plasmid vector pBluescript II SK(+) by using a DNA ligation kit (Takara Shuzo Co., Ltd.), thereby to construct the recombinant plasmid vector pOSASA-1.

The thus constructed plasmid vector pOSASA-1 was then introduced into *E. coli* XLI-Blue MRF' by the method described in the above (6). The *E. coli* which was transformed by the introduction of the plasmid vector pOSASA-1, was named *Escherichia coli* XLI-Blue MRF' (Os-asa1), and it was deposited with the National Institute of Bioscience and Human-Technology, Agency of Industrial Science and Technology, Tsukuba-shi, Ibaraki-ken, Japan on Aug. 18, 1997 with accession number FERM P-16388. This *E. coli* transformant was also deposited with the above depository on Aug. 7, 1998 under the Budapest Treaty with accession number FERM BP-6453.

(ii) From the above eight kinds of the recombinant plasmid DNA fragments was selected such one recombinant plasmid DNA which was judged to carry the DNA sequence consisting of 1821 nucleotides shown in SEQ ID NO: 10 (named as DNA sequence OSASA-W2) (i.e. the DNA for encoding the rice ASA2 α-subunit). The so selected recombinant plasmid DNA fragment was digested with the restriction enzyme EcoRI, and the digestion product was subjected to low-melting point agarose electrophoresis, to obtain such a DNA fragment which was judged to carry the DNA sequence OSASA-W2 (and which DNA fragment was named as DNA sequence OSASA-2). The thus obtained DNA sequence OSASA-2 was ligated into the EcoRI cleavage site of the plasmid vector pBluescript II SK(+) by using a DNA ligation kit (Takara Shuzo Co., Ltd.), thereby to construct the recombinant plasmid vector pOSASA-2.

The thus constructed plasmid vector pOSASA-2 was introduced into *E. coli* XLI-Blue MRF' by the method described in the above (6). The *E. coli* which was transformed by the introduction of the plasmid vector pOSASA-2 was named *Escherichia coli* XLI-Blue MRF' (Os-asa2), and it was deposited with the National Institute of Bioscience and Human-Technology, Agency of Industrial Science and Technology, Tsukuba-shi, Ibaraki-ken, Japan on Jun. 18, 1998 with accession number FERM P-16853. This *E. coli* transformant was also deposited with the above depository on Aug. 7, 1998 under the Budapest Treaty with accession number FERM BP-6454.

EXAMPLE 2

This Example illustrates the preparation of a DNA fragment carrying therein the DNA sequence which was obtained by the third aspect of the present invention and was named as the modified D sequence (i.e. the DNA sequence having the nucleotide sequence consisting of 1734 nucleotides shown in SEQ ID NO: 12).

(1) Construction of Synthetic Oligonucleotides as Primers for PCR

Four kinds of primers were synthesized by using a DNA synthesizer (Model-391, Applied Biosystems, Inc.). Thus, the following four primers were prepared by chemical synthesis: -primer OSASN1, that is, the oligonucleotide having the nucleotide sequence shown in SEQ ID NO: 16 of Sequence Listing; and primer OSASN2 having the nucleotide sequence shown in SEQ ID NO: 17; and primer OSASC1 having the nucleotide sequence shown in SEQ ID NO: 18; and primer OSASC2 having the nucleotide sequence shown in SEQ ID NO: 19 of Sequence Listing.

(2) Preparation of Template for PCR

In Example 1(8), the DNA fragment OSASA-1 was obtained from the recombinant phage by the EcoRI digestion and was deemed as the DNA fragment which was judged to carry the DNA sequence corresponding to the rice ASA1 α-subunit gene, and which was named the DNA sequence OSASA-W1. This DNA fragment OSASA-1 was ligated into the EcoRI cleavage site of the plasmid vector pBluescript II SK(+) by using a DNA ligation kit, thereby to construct the recombinant plasmid vector which was named pOSASA-1. This plasmid vector pOSASA-1 was now utilized as the template in the PCR described below.

(3) Amplification of the Desired DNA Fragments by PCR and Recovery Thereof (i) First Step of PCR In order to amplify the desired DNA fragments by PCR, the following reactions (A) and (B) were carried out as the first step of PCR.

The reaction (A) was carried out by adding 5 µl of the above recombinant plasmid vector pOSASA-1 as the template, 1 µM of the above primer OSASAN1 and 1 µM of the primer OSASAC1, to 100 µl of a mixture for amplification reaction [comprising 10 mM Tris-HCl (pH 8.3), 1 mM $MgCl_2$, 50 mM KCl, a mixture of 0.2 mM each of four kinds of nucleotide dNTP, and 2.5 units of LA Taq DNA polymerase], and subjecting the resulting mixture to the amplification reaction. The DNA amplification product was obtained by this reaction (A) and was named DNA fragment-A.

The reaction (B) was carried out by adding 5 µl of the above plasmid vector pOSASA-1 as the template, 1 µM of the primer OSASAC2 and 1 µM of the primer OSASAN2 to the same mixture for amplification reaction as used in the reaction (A), and subjecting the resulting mixture to the amplification reaction. The DNA amplification product was obtained by this reaction (B) and was named DNA fragment-B.

The above amplification reactions were carried out by repeating 20 times a reaction cycle which consisted of denaturation at 94° C. for 30 seconds, annealing at 55° C. for 30 seconds and extension at 72° C. for one minute in a PCR reaction apparatus (Program Temp Control System PC-700, ASTEC).

After the completion of the amplification reactions, the reaction mixture resulting from the reaction (A) was fractionated by low-melting point agarose electrophoresis, and a band containing the DNA fragment-A of 268 bp as the DNA amplification product was cut out of the agarose gel. The reaction mixture resulting from the reaction (B) was fractionated by low-melting point agarose electrophoresis, and a band containing the DNA fragment-B of 336 bp as the DNA amplification product was cut out of the agarose gel.

The purified product of DNA fragment-A and the purified product of DNA fragment-B were obtained from the above two gel pieces, respectively, by using GENECLEAN II Kit (Funakoshi).

(ii) Second Step of PCR

Next, in the second step of PCR, 1 µl of the purified product of DNA fragment-A as amplified by the above reaction (A), as well as 1 µl of the purified product of DNA fragment-B as amplified by the above reaction (B), were added to 100 µl of a mixture for amplification reaction [comprising 10 mM Tris-HCl (pH 8.3), 1 mM $MgCl_2$, 50 mM KCl, a mixture of 0.2 mM each of dNTP, and 2.5 units of LA Taq DNA polymerase]. The resulting mixture was subjected to the amplification reaction. The amplification reaction was carried out by conducting once a reaction cycle which consisted of denaturation at 94° C. for 5 minutes, annealing at 65° C. for 10 minutes and at 55° C. for 10 minutes and extension at 72° C. for one minute.

After the completion of the amplification reaction, the resulting reaction mixture was fractionated by low-melting point agarose electrophoresis, and a band containing the desired DNA fragment-C of 583 bp as the DNA amplification product was cut out of the agarose gel. From this gel piece was obtained the purified product of DNA fragment-C by using GENECLEAN II Kit (Funakoshi).

(4) The DNA fragment-C obtained as above was used in the next step to produce by coloning a sufficient amount of a DNA fragment carrying the desired modified D sequence of the second aspect of the present invention.

(i) The DNA fragment-C obtained as above (10 µg) was digested with 10 units each of the restriction enzymes AflII and BglII in H buffer (Takara Shuzo Co., Ltd.). The DNA fragment as obtained by this AflII-BglII digestion was named DNA fragment-α. Separately, 10 µg of the above plasmid vector pOSASA-1 was digested with 10 units each of AflII and BglII in H buffer (Takara Shuzo Co., Ltd.), to obtain a shortened plasmid. To each of the digestion mixtures respectively containing the sadi DNA fragment-α and the shortened plasmid, were added a 1/10 volume of 3 M sodium acetate and a two-fold volume of ethanol, followed by incubation at −20° C. for about 6 hours. The so incubated solutions were centrifuged, and the DNAs so precipitated from the respective solutions were separately dried and then dissolved in 5 µl of water.

The resulting aqueous solution(5 µl) of the DNA fragment-α and the resulting aqueous solution(5 µl) of the shortened plasmid DNA were mixed together. The resulting mixture (10 µl) was subjected to reaction for ligating both the DNAs, by using DNA Ligation Kit (Takara Shuzo Co., Ltd.). To the ligation mixture so obtained were added a 1/10 volume of 3 M sodium acetate and a two-fold volume of ethanol, followed by incubation at −20° C. for about 6 hours.

The resulting incubated reaction mixture was centrifuged, and the ligated DNA as precipitated was dried and dissolved in 5 µl of water.

The above ligated DNA, which was contained in the so prepared aqueous solution, is such a circular double strand recombinant plasmid, which was constructed from the ligation of the above DNA fragment-α with the above shortened plasmid as obtained by the AflII-BglII digestion of the plasmid vector pOSASA-1 (that is, said double strand recombinant plasmid was named as the pBluescript-DNA-D plasmid), and which carries the modified D sequence within the DNA insert present in said recombinant plasmid DNA.

(ii) Said pBluescript-DNA-D plasmid was introduced into E. coli XLI-Blue MRF', to transform the latter.

The thus transformed E. coli was named as *Escherichia coli* XLI-Blue MRF'/pBluescript-DNA-D, and it was deposited with the above-mentioned National Institute of Bioscience and Human-Technology on Aug. 7, 1998 under the Budapest Treaty with accession number FERM BP-6451. Cells of this E. coli transformant were then cultured in a liquid medium.

A plasmid was extracted from the so cultured *E. coli* cells. In this manner, the recombinant plasmid pBluescript-DNA-D carrying the modified D sequence was cloned.

(5) Recovery of a DNA Fragment Carrying the Modified D Sequence

The plasmid pBluescript-DNA-D obtained as above (10 µl) was then digested with 10 units of EcoRI in H buffer (Takara Shuzo Co., Ltd.). The resulting digestion mixture was fractionated by low-melting point agarose electrophoresis, and a band of a DNA fragment (named DNA fragment-β) carrying the 1734 bp OSASA-W1 sequence was cut out of the agarose gel.

To this agarose piece containing the DNA fragment-β was then added an equal amount of TE buffer (10 mM Tris-HCl and 1 mM EDTA, pH 8), followed by heating at 68° C. for 20 minutes, to dissolve the agarose in the buffer. The resulting solution was extracted twice with saturated phenol to remove the agarose. To the resulting phenol extract containing the DNA were then added a 1/10 volume of 3 M sodium acetate and a two-fold volume of ethanol, followed by incubation at −20° C. for about 6 hours. The so incubated solution was centrifuged at 15000 rpm at 4° C. for 10 minutes. The precipitated DNA was dried under reduced pressure. The resultant DNA powder was dissolved in 10 µl of water.

This DNA powder comprised the DNA fragment-β carrying the desired modified D sequence.

The DNA fragment-β as obtained in the above Example 2(5) was then analyzed by means of an automatic DNA sequencer, ALF DNA Sequencer II, using a nucleotide sequence determination kit in the same manner as in Example 1(7). The result of this analysis was to confirm that the DNA fragment-β was the DNA fragment carrying the modified D sequence which has the nucleotide sequence of SEQ ID NO: 12 of Sequence Listing and consists of the 1734 nucleotides.

EXAMPLE 3

This Example illustrates a process for the transformation of a rice plant, which comprises introducing, as an exogenous gene, either the DNA sequence of SEQ ID NO: 1 according to the first aspect of the present invention, or the modified DNA sequence having the nucleotide sequence of SEQ ID NO: 12 according to the third aspect of the present invention into the rice plant by the Agrobacterium method. This Example also demonstrates that such transformation increases the tryptophan content of the plant.

(1) Construction of Recombinant Vector pUBdD for Introduction of an Exogenous Gene into a Rice Plant (i) First, 10 µg of pUBA plasmid DNA, (which is a known 5.6 kb plasmid vector containing the maize ubiquitin promoter, 1st intron and NOS terminator and an ampicillin resistance gene) was digested with 10 units of the restriction enzyme BamHI in K buffer (Takara Shuzo Co., Ltd.). DNA was precipitated from the resulting digestion mixture, centrifuged and dried. After being dissolved in 10 µl of sterilized water, the DNA was subjected to the blunting treatment using a DNA blunting kit (Takara Shuzo Co., Ltd.). The resulting DNA having the blunt ends was precipitated, centrifuged and dried. The dried DNA was dissolved in 10 µl of sterilized water and then digested with 10 units of the restriction enzyme SacI in L buffer (Takara Shuzo Co., Ltd.). DNA was precipitated from the digestion mixture, centrifuged and dried. This procedure gave a ca. 4.8 kb vector fragment which carryed the ubiquitin promoter, the 1st intron, the NOS terminator and the ampicillin resistance gene (see the left part of FIG. 1 in the attached drawings).

(ii) Separately, 10 µg of the recombinant plasmid pBluescript-DNA-D (1.7 kb) carrying the modified D sequence (which is the DNA of the third aspect of the present invention) was digested with 10 units of the restriction enzyme EcoRV in H buffer (Takara Shuzo Co., Ltd.). DNA was precipitated from the digestion mixture, centrifuged and dried. The dried DNA was dissolved in 10 µl of sterilized water and then digested with 10 units of the restriction enzyme SacI in L buffer (Takara Shuzo Co., Ltd.). Dried DNA was obtained from the digestion mixture in the same manner as above. Thereby, pBluescript-DNA-D vector fragment was obtained (see the right part of FIG. 1 in the attached drawings).

(iii) The ca. 4.8 kb vector fragment as obtained in the above (i) and the vector fragment as obtained in the above (ii) were separately dissolved in 5 µl of sterilized water. The resulting two aqueous solutions of the vector fragments (5 µl each) were mixed together. The resultant mixture was subjected to DNA ligation reaction by using a DNA ligation kit (Takara Shuzo Co., Ltd.). This reaction gave such a 6.5 kb circular recombinant vector in which the above pBluescript-DNA-D-derived vector fragment was ligated with the vector fragment as derived from the plasmid vector pUBA. This circular recombinant vector was named pUBdD (see the lower part of FIG. 1). The vector pUBdD had a size of 6.5 kb and was found to carry the 1st intron region downstream of the ubiquitin promoter region, and the modified D sequence of the third aspect of the present invention inserted between the 1st intron region and the NOS terminator region, as well as the ampicillin resistance gene.

(2) Construction of Recombinant Vector pUBdW1 for Introduction of an Exogenous Gene into a Rice Plant (i) First, 10 µg of pUBA plasmid DNA (which is a known 5.6 kb plasmid vector containing the maize ubiquitin promoter, 1st intron and NOS terminator and an ampicillin resistance gene) was treated in the same manner as in the above (i) and (ii), thereby to obtain the ca. 4.8 kb vector fragment which carryed the ubiquitin promoter, the 1st intron, the NOS terminator and the ampicillin resistance gene (see the left part of FIG. 1).

(ii) Separately, 10 µg of the recombinant plasmid pOSASA-W1 (4.7 kb) carrying the sequence OSASA-W1 (which is the DNA sequence of SEQ ID NO: 1 according to the first aspect of the present invention) was digested with 10 units of the restriction enzyme EcoRV in H buffer (Takara Shuzo Co., Ltd.). DNA was precipitated from the digestion mixture, centrifuged and dried. The dried DNA was dissolved in 10 μl of sterilized water and then digested with 10 units of the restriction enzyme SacI in L buffer (Takara Shuzo Co., Ltd.). Dried DNA was obtained from the digestion mixture in the same manner as above.

(iii) The ca. 4.8 kb vector fragment as obtained in the above (i) and the vector fragment as obtained in the above (ii) were separately dissolved in 5 μl of sterilized water. The resulting two aqueous solutions of the vector fragments (5 μl each) were mixed together. The resultant mixture was subjected to DNA ligation reaction by using a DNA ligation kit (Takara Shuzo Co., Ltd.). This reaction gave such a circular recombinant vector in which the above pOSASA-W1-derived vector fragment was ligated with the pUBA-derived vector fragment. This circular recombinant vector was named pUBd-W1. The vector pUBd-W1 was found to carry the 1st intron region downstream of the ubiquitin promoter region, and the sequence OSASA-W1 inserted between the 1st intron region and the NOS terminator region, as well as the ampicillin resistance gene.

Figure 2:
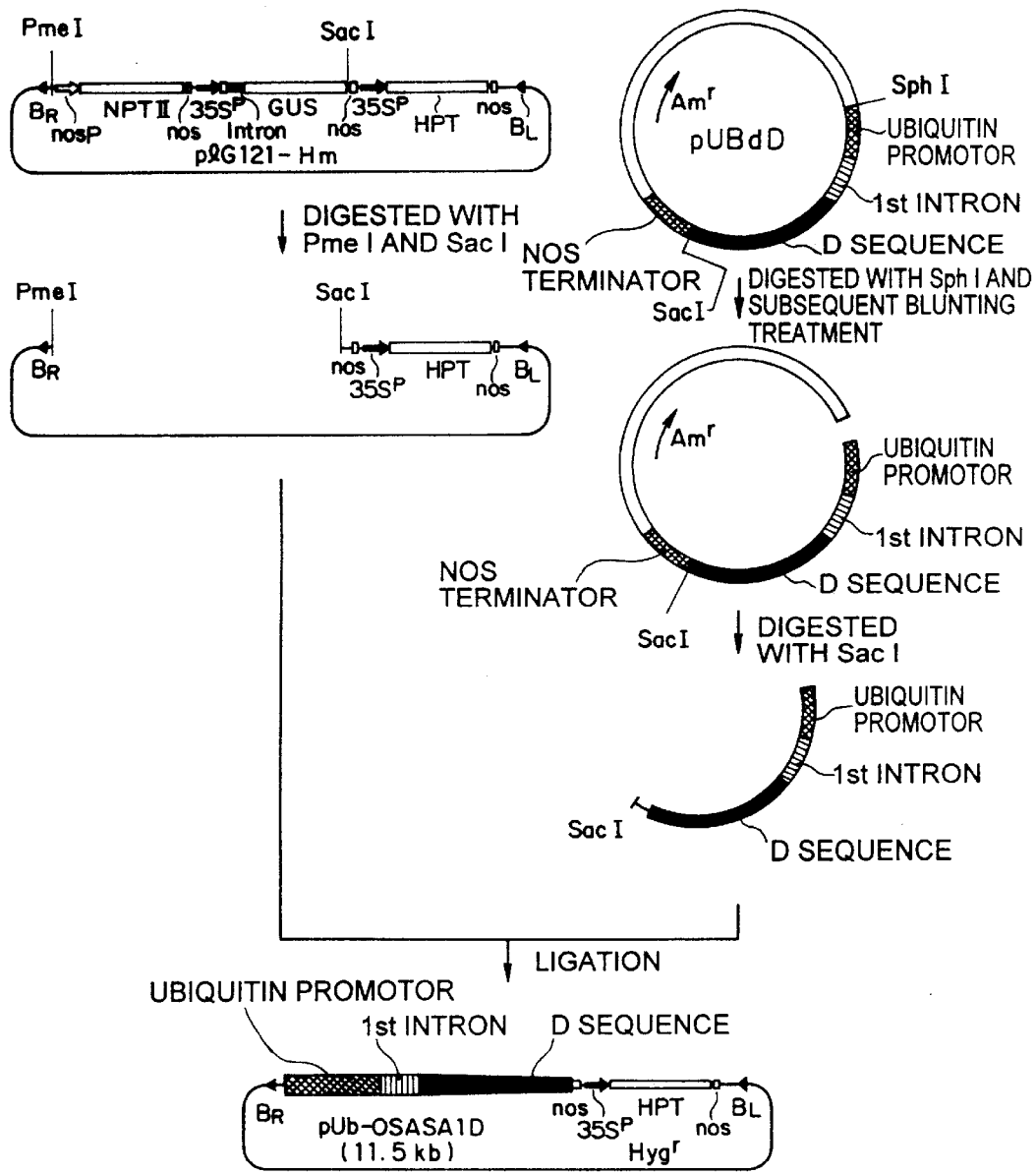
FIG. 2 is a schematic illustration of the process employed in Example 3(3) wherein there was constructed from the vector pIG121-Hm, the vector pUb-OSASA1D which is a recombinant vector for the exogenous gene introduction used for transforming rice callus cells by introduction of an exogenous gene according to the Agrobacterium method, and which vector pUb-OSASA1D carries the "modified D sequence" mentioned above.

(3) Construction of Recombinant Vectors pUb-OSASA1D or pUb-OSASAW1 for Introduction of Exogenous Genes into Rice Plants (i) The pUbdD plasmid vector DNA as obtained in the above (2) (iii) (10 μg) was digested with 10 units of the restriction enzyme SphI in H buffer (Takara Shuzo Co., Ltd.). DNA was precipitated from the resulting digestion mixture, centrifuged and dried. The thus obtained vector fragment was dissolved in 10 μl of sterilized water (see the right part of FIG. 2 in the attached drawings). Then, 10 μl of the resultant aqueous solution of the vector fragment was subjected to the reaction for blunting the enzyme-cleaved end, with using a DNA blunting kit (Takara Shuzo Co., Ltd.). DNA was precipitated from the reaction mixture, centrifuged and dried. After the dried vector fragment DNA was dissolved in 10 μl of sterilized water, 10 μg of this vector fragment DNA was digested with 10 units of the restriction enzyme SacI in L buffer (Takara Shuzo Co., Ltd.). DNA was precipitated from the resulting digestion mixture, centrifuged and dried. This procedure gave such a vector fragment which carryed the ubiquitin promoter and the modified D sequence of SEQ ID NO: 12 according to the third aspect of the present invention (see the third figure in the right part of FIG. 2 in the attached drawings).

(ii) Separately, 10 μg of pIG121Hm plasmid DNA (which is a known 15 kb plasmid vector containing a hygromycin resistance gene) was digested with 10 units of the restriction enzyme SacI in L buffer (Takara Shuzo Co., Ltd.). DNA was precipitated from the digestion mixture, centrifuged and dried. The dried DNA was dissolved in 10 μl of sterilized water and then digested with 10 units of the restriction enzyme PmeI in NEB4 buffer (New England Biolab). Dried DNA was obtained from the digestion mixture in the same manner as in the above (1) (i). This procedure gave such a ca. 9.8 kb vector fragment carrying the hygromycin resistance gene (see the left part of FIG. 2).

(iii) The ca. 9.8 kb vector fragment as obtaint in the above (ii) and the D sequence-carrying vector fragment as obtained in the above (i) were separately dissolved in 5 μl of sterilized water. The resulting two aqueous solutions of the vector fragments (5 μl each) were mixed together. The resultant mixture was subjected to DNA ligation reaction by using a DNA ligation kit (Takara Shuzo Co., Ltd.). This reaction gave such a circular recombinant vector in which the D sequence fragment was ligated with the PmeI-SacI fragment as derived from the plasmid vector pIG121Hm. This circular recombinant vector was named pUb-OSASA1D (see the lower part of FIG. 2). The vector pUb-OSASA1D had a size of 11.5 kb and was found to carry the 1st intron region downstream of the ubiquitin promoter region, and the D sequence inserted between the 1st intron region and the NOS terminator region, and the hygromycin resistance gene capable of expression in a plant, as well as a kanamycin resistance gene.

Separately, the aforesaid OSASAW1 fragment, instead of the above D sequence fragment, was ligated with the ca. 9.8 kb vector fragment as obtained in the above (ii), in the same manner as described above, thereby to construct a circular recombinant vector. The so obtained recombinant vector was named pUb-OSASAW1.

(4) Preparation of Agrobacterium Bacteria

Agrobacterium (*Agrobacterium tumefaciens* LBA4404, purchased from Clontech) was inoculated into 300 ml of LB liquid medium (comprising 10 g/l Bacto-tryptone, 5 g/l Bacto-yeast extract, 5 μl NaCl, pH 7), followed by making the shaking culture at 30° C. for 16 hours. The resulting bacterial culture was cooled at 4° C. for 10 minutes and then centrifuged to precipitate the bacterium. After the precipitated bacterium was subjected to washing with ice-cooled 10% glycerol and to centrifugation three times, the resulting precipitate was dissolved in 10 ml of 10% glycerol.

Then, 40 μl portions of the obtained solution were put into Eppendorf tubes, and 5 μl each of solutions of the above recombinant vectors pUb-OSASA1D or pUb-OSASAW1 (40 ng) were respectively added to the tubes, followed by thorough mixing. Each mixture so obtained was allowed to stand on ice for 3 minutes and then transferred into an electroporation cuvette (distance between the electrodes: 0.2 cm) Electroporation was carried out using an electroporation apparatus (Gene Pulser, Bio Rad) under the following conditions: voltage, 12.5 kV/cm; condenser capacity, 25 μF; resistance, 600. To the cuvette was added 0.8 ml of SOC medium (GIBCO BRL), and the resulting suspension was transferred into a 2-ml test tube, followed by the shaking culture at 30° C. for one hour. The resulting culture was spread over an agar medium as prepared by adding 50 mg/l kanamycin to LB medium. After cultivation was made at 300° C. for 36 hours, the colonies grown on the medium were obtained as the desired transformed Agrobacterium carrying the recombinant vector as employed.

The Agrogacterium bacterium as transformed with the recombinant vector pUb-OSASA-D was named pUb-OSASA-1D/LBA4404. The Agrogacterium bacterium as transformed with the vector pUb-OSASAW1 was named pUb-OSASAW1/LBA4404.

(5) Preparation of Rice Calluses

Ripe seeds of rice (variety: Nihonbare) were hulled, and the resulting seeds with coats were sterilized by immersion in a 70% ethanol solution for 60 seconds and then in a sodium hypochlorite solution containing about 1% effective chlorine for 6 minutes, followed by washing with sterilized water.

The thus sterilized rice seeds were placed on a medium as prepared by adding 30 g/l sucrose, 2 mg/l 2,4-PA as a phytohormone and 8 g/l agar to the inorganic component composition of MS medium. Incubation was carried out at 28° C. for 21 days with irradiation with light at 2000 lx for 16 hours per day to form callus. The formed callus was cut from the albumen of the seeds and then transplanted to a medium having the same composition as above, followed by cultivation for 3 days.

(6) Introduction of Exogenous Genes into Rice Callus

The transformed Agrobacterium for the gene introduction obtained as above (namely, pUb-OSASA1D/LBA4404 or pUb-OSASAW1/LBA4404) was suspended in 30 ml of a liquid medium as prepared by adding 20 g/l sucrose, 2 mg/l 2,4-PA, 0.2 mg/l kinetin and 10 mg/l acetosyringone to the inorganic salt composition of AA medium. Then, the resulting bacterium suspension was put in a petri dish (9 cm), and the rice callus as obtained in the above (5) (100 calluses) were then soaked in the bacterium suspension for 5 minutes. After removal of excess of the bacterium suspension with a paper towel, the soaked callus (20 callus per petri dish) were placed on a solid medium as prepared by adding 30 g/l sucrose, 10 g/l glucose, 2 mg/l 2,4-PA, 2 g/l Gerite and 10 mg/l acetosyringone to the inorganic salt composition of N 6 medium. Cultivation of the bacterium was carried out in the dark at 28° C. for 3 days so as to infect the rice callus with the Agrobacterium.

(7) Selection of Callus as Transformed with the Introduced Vectors

The transformed callus, which carryed the recombinant vectors as introduced in the above (6), were washed with sterilized water containing 500 mg/l carbenicillin, to remove the Agrobacterium bacteria. After removal of excess water, the calli (20 calli per petri dish) were transplanted to a solid medium as prepared by adding 30 g/l sucrose, 2 mg/l 2,4-PA, 500 mg/l carbenicillin, 50 mg/l hygromycin and 2 mg/l Gel lite to the inorganic salt composition of N 6 medium. Cultivation was carried out at 25° C. for 21 days with irradiation with light at 2000 lx for 16 hours per day, to obtain the hygromycin-resistant transformed callus.

(8) Reselection of Callus as Transformed with Vector pUb-OSASA1D

From the hygromycin-resistant transformed calli obtained as above were then reselected such transformed calluses which sufficiently contained the modified D sequence as introduced as the exogenous gene, with said modified D sequence being carried by the vector pUb-OSASA1D and being capable of expressing its function in a plant. To this end, 15 transformed calli (diameter: 5 mm) were transplanted to a solid medium as prepared by adding 30 g/l sucrose, 2 mg/l 2,4-PA, 250 mg/l carbenicillin, 2 g/l Gel lite and $3 \times 10^{-4}$ M 5-methyltryptophan (hereinafter referred to as 5MT) (a tryptophan analogue) (which acts as a cell growth inhibitor) to the inorganic salt composition of N6 medium. Cultivation of callus was carried out at 25° C. for 21 days with irradiation with light at 2000 lx for 16 hours per day. The callus observed to be growing on the above 5MT-containing medium were reselected as the transformed callus containing the D sequence capable of expressing its function in a plant.

(9) Plant Regeneration from Transformed Callus Cells

The resulting hygromycin-resistant and 5MT-resistant transformed calli obtained as above (14–15 calli) were respectively transplanted to solid media as prepared by adding 30 g/l sucrose, 30 g/l sorbitol, 2 g/l casamino acid, 1 mg/l NAA, 2 mg/l BA, 50 mg/l hygromycin and 4 g/l Gerite to the inorganic salt composition of MS medium. Cultivation was carried out at 25° C. for 30 days with irradiation with light at 2000 lx for 16 hours per day, whereby buds and roots could be regenerated from the transformed calluses. The regenerated explants (buds grown to a length of 10–30 mm) were transplanted into MS medium containing 30 g/l sucrose and 2 g/l Gerite in a test tube (diameter: 45 mm, length: 25 cm). By cultivation of the plumules for 20 days, the transformed rice plants were obtained.

By the above procedure, 10 rice plants were regenerated from the 15 transformed calli containing the OSASAW1 sequence of SEQ ID NO: 1 as an exogenous gene.

Similarly, 10 rice plants were regenerated from the 14 5MT-resistant transformed calli containing the modified D sequence of SEQ ID NO: 12 as an exogenous gene.

(10) Gene Analysis of Regenerated Transformed Rice Plants

The ASA-encoding DNAs contained in the rice plants, which were regenerated as above, were analyzed by PCR according to the following procedure.

(i) Leaves were taken from each of the rice plant as regenerated in the above (9). The leaves (50 mg) were put in a 1.5-ml microtube, and 300 μl of 20 mM Tris-HCl buffer (pH 7.5) containing 10 mM EDTA was added thereto. After the leaves were disrupted, 20 ml of 20% SDS was added, followed by heating at 65° C. for 10 minutes. To the mixture was added 100 μl of 5 M potassium acetate. The resulting mixture was allowed to stand in ice for 20 minutes and then centrifuged at 17000×g for 20 minutes. To the supernatant was added 200 μl of isopropanol, and the mixture was agitated by inversion, followed by centrifugation at 17000×g for 20 minutes. The precipitated DNA was dried under reduced pressure and then dissolved in 100 μl of TE buffer.

(ii) The above-mentioned oligonucleotide having the nucleotide sequence shown in SEQ ID NO: 14 and the above-mentioned oligonucleotide having the nucleotide sequence shown in SEQ ID NO: 15 were used as the PCR primers.

These two kinds of the oligonucleotides (1 μM each) as the primers as well as the above DNA as derived from the regenerated rice plant (5 μl) as the template, were added to 100 μl of a mixture for amplification reaction [comprising 10 mM Tris-HCl (pH 8.3), 1.0 mM $MgCl_2$, 50 mM KCl, 0.01% gelatin, pH 8.3, a mixture of dNTP (0.2 mM each) and 2.5 units of Taq DNA polymerase]. The amplification reaction was carried out. The said mixture for amplification reaction was prepared by using a PCR kit (PCR Amplification Kit, Takara Shuzo Co., Ltd.).

The amplification reaction was carried out by repeating 30 times a reaction cycle each consisting of denaturation at 94° C. for one minute, annealing at 60° C. for 30 seconds and extension at 72° C. for one minute in a PCR reaction apparatus (Program Temp Control System PC–700, ASTEC).

(iii) The resulting PCR reaction mixture was analyzed by agarose electrophoresis in a usual manner. Thereby, various DNA bands having been amplified from the DNA as extracted from the regenerated rice plant were confirmed.

When analysis of these amplified DNA sequences was made using a nucleotide sequence determination kit, it was confirmed that the DNA fragments as extracted from the regenerated rice plant were containing either the DNA fragment corresponding to the DNA sequence OSASA-W1 (SEQ ID NO: 1) according to the first aspect of the present invention, or the modified D sequence (SEQ ID NO: 12) according to the third aspect of the present invention.

The regenerated rice plants, which were confirmed to carry the introduced exogenous gene by the gene analysis according to he PCR method described above, were respectively transplanted into pots containing culture soil, and then cultured. These regenerated rice plants showed the normal growth and yielded self-fertilized seeds.

(11) Determination of Tryptophan Content of Regenerated Body of Transformed Rice Plants Green leaves were taken from the regenerated, transformed rice plants having plant cells containing the introduced recombinant vector pUb-OSASAW1 carrying the OSASA-W1 sequence of the first aspect of the present invention. Also green leaves were taken from the regenerated transformed rice plants having plant cells containing the introduced recombinant vector pUb-OSASA1D carrying the modified D sequence. The above regenerated plants were obtained in the above (10).

The leaves were thus taken from each plant in an amount of 1 g, and 100 mg of the leaves was put into the first 1.5-ml tube, followed by addition of 1 ml of 50% acetonitrile and disruption. The disrupted mixture was transferred into the second 1.5-ml tube and centrifuged at 1700×g for 20 minutes. The obtained supernatant was transferred into the third tube, and 1 ml of 50% acetonitrile was added thereto. After being thoroughly agitated by inversion, the mixture was centrifuged. The obtained supernatant was put into the first tube. This procedure was repeated three times, whereby an acetonitrile extract containing tryptophan as extracted from the leaves was obtained.

This acetonitrile extract was dried under reduced pressure, and 1 ml of distilled water was added thereto to make an aqueous solution. The aqueous solution was centrifuged at 17000×g for 20 minutes to obtain 0.5 ml of the supernatant. To 100 µl of the supernatant was added 100 µl of 5 mM DNFB (2,4-dinitro-1-fluorobenzene). The resulting mixture was subjected to reaction overnight. To the reaction mixture was added 200 µl of acetonitrile, and after stirring, the mixture was centrifuged at 17000×g for 20 minutes whereby a tryptophan extract was obtained as the supernatant. The extract was subjected to high performance liquid chromatography (HPLC) using an HPLC apparatus (Model 8020, Tosoh Corporation), to determine the free tryptophan content. HPLC was carried out under the following conditions: column, CAPCELL PAK-C18 (Shiseido Co., Ltd.); developing solvent, acetonitrile-water (concentration gradient with 60%–72% acetonitrile); flow rate, 0.8 ml/min; measurement, absorbance at 350 nm.

As a control rice plant, was used an ordinary rice plant (variety: Nihonbare) which had not been transformed. The results of the measurements are shown in Table 1.

TABLE 1

| Rice Plant Tested | Free Tryptophan Content (nmol/FWg) |
|---|---|
| Control Rice Plant | 33 |
| Rice Plant Carrying Vector pUb-OSASAW1: W1 | 143 |
| Rice Plant Carrying Vector pUb-OSASAW1: W2 | 186 |
| Rice Plant Carrying Vector pUb-OSASA1D: D19 | 354 |
| Rice plant Carrying Vector pUb-OSASA1D: D20 | 1522 |

As obvious from the data in Table 1, it was confirmed that the free tryptophan content of rice plants could be increased by the introduction of the novel DNA sequence of the present invention with utilizing the novel DNA sequence of the present invention as an exogenous gene and also a recombinant vector containing a promoter capable of expressing said gene in plant cells.

EXAMPLE 4

This Example illustrates the process for selecting a transformed cell according to the thirteenth aspect of the present invention, which comprises introducing the DNA sequence of the present invention as an exogenous gene into a rice plant, and the process for producing a transformed plant according to the fourteenth aspect of the present invention.
(1) Construction of Recombinant Vectors for Introduction of Exogenous Genes The recombinant vector pUb-OSASA1D or recombinant vector pUbdD described in Example 3 were used as the recombinant vectors for introduction of exogenous genes.

(2) Introduction of an Exogenous Gene into Rice Callus Cells by the Agrobacterium Method or the Whisker Method and Selection of Transformed Cells
  (i) Agrobacterium Method Preparation of Agrobacterium bacterium was carried out in the same manner as in Example 3(4) using the recombinant vector pUb-OSASA1D mentioned in the above (1). Preparation of rice callus cells was carried out in the same manner as in Example 3(5). And, gene introduction into the rice callus cells was carried out in the same manner as in Example 3(6).

The obtained calli as transformed with the recombinant vector were washed with sterilized water containing 500 mg/l carbenicillin, to remove the Agrobacterium bacterium. After removal of excess water, the calli (20 calli per petri dish, 500 calli in total) were transplanted to a solid medium as prepared by adding 30 g/l sucrose, 2 mg/l 2,4-PA, 500 mg/l carbenicillin, 2 g/l Gerite and $3×10^{-4}$ M 5MT as a selective drug, to the inorganic salt composition of N6 medium. Cultivation of the callus was carried out at 25° C. for one month with irradiation with light at 2000 lx for 16 hours per day.

After one month of cultivation, the number of the transformed calli thus selected was counted. The result is shown in Table 2. For a control group, a solid medium containing 50 mg/l hygromycin instead of 5MT was used.

The transformed calli as selected by the above cultivation in view of their 5MT resistance were transplanted to a solid regeneration medium which was prepared by adding 30 g/l sucrose, 30 g/l sorbitol, 2 g/l casamino acid, 1 mg/l NAA, 2 mg/l BA, 4 g/l Gel lite and $3×10^{-4}$M 5MT to the inorganic salt composition of MS medium. Cultivation of callus was carried out at 25° C. for 30 days with irradiation with light at 2000 lx for 16 hours per day. The number of the transformed plants regenerated from the transformed calluses was counted. The result is shown in Table 2. For a control group, a solid medium containing 50 mg/l hygromycin instead of 5MT was used.
  (ii) Direct Introduction Using Whiskers Ripe seeds of rice (variety: Nihonbare) were hulled, and the resulting seeds with coats were sterilized by immersion in a 70% ethanol solution for 60 seconds and then in a sodium hypochlorite solution containing about 1% effective chlorine for 6 minutes, followed by washing with sterilized water.

The thus sterilized rice seeds were placed on a medium as prepared by adding 30 g/l sucrose, 2 mg/l 2,4-PA as a phytohormone and 8 g/l agar to the inorganic component composition of MS medium. Incubation of seeds was carried out at 28° C. for 45 days with irradiation with light at 2000 lx for 16 hours per day, to form callus. The formed calli were cut from the albumen of the seeds, and those calli having a size of 1 mm or less were obtained in an amount of 3 ml in term of PCV (Packed Cell Volume), with using a stainless steel sieve (mesh size: 1 mm).

Separately, 5 g of potassium titanate whiskers (LS20, Titan Kogyo K.K.) was put into a 1.5-ml tube, and 0.5 ml of ethanol was added thereto. The mixture was allowed to stand overnight, and ethanol was evaporated completely to obtain sterilized whiskers. To this tube containing the whiskers was added 1 ml of sterilized water, followed by sufficient stirring. The whiskers and the sterilized water were separated by centrifugation, and the supernatant water was discarded. The whiskers were washed in this manner. Such washing step was carried out three times. Then, 0.5 ml of R2 liquid medium was added to the tube, to obtain a whisker suspension.

To the tube containing the obtained whisker suspension was added 250 μl of the callus having a size of 1 mm or less, followed by stirring. The resulting mixture was centrifuged at 1000 rpm/min for 10 seconds, to precipitate the callus and the whiskers. The supernatant was discarded to obtain a mixture of the callus and the whiskers.

To the tube containing the callus-whisker mixture was added 10 μl of the recombinant vector (the above-mentioned recombinant vector pUBdD) (containing 10 μg of DNA), followed by sufficient mixing and shaking, to obtain a uniform mixture.

The resulting uniform mixture in the tube was centrifuged at 18000 ×g for 5 minutes and then mixed again by shaking. This step of centrifugation and mixing and shaking was repeated three times.

Then, the tube containing the callus cells, the whiskers and the recombinant vector carrying the DNA sequence of the present invention was placed in a bath of an ultrasonic generator, so that the tube was adequately immersed therein. Ultrasonic waves at the frequency of 40 kHz were applied to the tube at the intensity of 0.25 W/cm$^2$ for one minute, followed by incubation at 4° C. for 30 minutes.

The ultrasonic-treated mixture was washed with R2 liquid medium, to obtain the desired transformed callus cells which carried the introduced recombinant vector pUBdD.

The calli having the transformed cells, which were obtained by the above introduction of the recombinant vector, were put in a petri dish (3.5 cm), followed by addition of 3 ml of a liquid medium which was prepared by adding 30 g/l sucrose and 2 mg/l 2,4-PA to the inorganic component composition of R2 medium. The callus cells were then cultured on a rotary shaker (50 rpm) at 28° C. with irradiation with light at 2000 lx for 16 hours per day, to obtain the divided cells.

On the third day of culturing, 3 ml of the resulting divided cell suspension (number of divided cells: 2000) was spread evenly over a medium which was prepared by adding 30 g/l sucrose, 2 mg/l 2,4-PA, 3 g/l Gerite and 10$^{-4}$M 5MT as the selective drug, to the inorganic component composition of N6 medium. Cultivation of the cell was carried out at 28° C. for one month with irradiation with light at 2000 lx for 16 hours per day.

After one month of cultivation, the number of the transformed calli thus selected was counted. The result is shown in Table 2. For a control group, a solid medium containing 50 mg/l hygromycin instead of 5MT was used.

The transformed calli, which were selected by the above cultivation based on 5MT resistance, were transplanted to a solid regeneration medium which was prepared by adding 30 g/l sucrose, 30 g/l sorbitol, 2 g/l casamino acid, 1 mg/l NAA, 2 mg/l BA, 4 g/l Gerite and 3×10$^{-4}$ M 5MT to the inorganic salt composition of MS medium. Cultivation was carried out at 25° C. for 30 days with irradiation with light at 2000 lx for 16 hours per day. The number of the transformed plants as regenerated from the transformed callus was counted. The result is shown in Table 2. For a control group, a solid medium containing 50 mg/l hygromycin instead of 5MT was used.

TABLE 2

| | | Callus Cells Tested | Transformed Callus Cells Selected | Transformed Plants Selected |
|---|---|---|---|---|
| Test Group | Agrobacterium Method | 500 | 45 | 43 |
| | Direct | 2000 | 102 | 85 |
| Control Group | Introduction Using Whiskers Agrobacterium Method | 500 | 42 | 40 |
| | Direct Introduction Using Whiskers | 2000 | 98 | 82 |

EXAMPLE 5

This Example illustrates a process for obtaining DNA corresponding to the promoter gene for the rice ASA gene.

(1) Preparation of Rice Genomic DNA

From 2 g of callus of rice (variety: Nihonbare) was extracted 2 mg of genomic DNA according to the known CTAB method (Cloning and Sequence: 1989, pp. 262–264, Nosonbunkasha).

(2) Construction of Rice Genomic DNA Library

10 μg of the above genomic DNA was partially digested with the restriction enzyme EcoRI, and then the resulting DNA fragments were subjected to 0.8% agarose gel electrophoresis. The fractionated DNA fragments were transferred to a nylon membrane, High Bond N (Amersham). The DNAs as transferred to the nylon membrane were treated with an alkaline denaturation solution (1.5 M NaCl, 2.0 M NaOH) and with a neutralization solution (1.0 M Tris-HCl, pH 5, 2.0 M NaCl) for 10 minutes each, followed by treatment at 80° C. for 2 hours so as to fix the DNAs on the nylon membrane.

Then, the DNAs fixed on the nylon membrane were subjected to hybridization reaction in the same manner as in Example 1(5), with using the DIG-labeled probe DNA as obtained in Example 1(5).

As a result, the DNA emitting a strong signal on an X-ray film was detected at a DNA size of about 6 kb on the nylon membrane. After separation of the DNA, the DNA was partially digested with the restriction enzyme EcoRI in the same manner as in Example 1(5). A portion of about 6 kb of the electrophoresed DNA fragments of the digested DNA was cut out of the agarose gel, followed by purification using a DNA purification kit (Gene Clean II Kit, Bio 101). The resulting purified DNA fragments were dissolved in 20 μl of TE buffer [10 mM Tris-HCl (pH 7.5), 1 mM EDTA]. The resultant fractionated rice genomic DNA was ligated into a vector by using a cloning kit (Lambda ZAPII/EcoRI/CIP Cloning Kit, STRATAGENE). The resulting recombinant vectors were packaged in a lambda phage by using Gigapack II Gold Packaging Extract. Then E. coli XLI-Blue MRF' was infected with the thus obtained recombinant λ phages, to obtain a large number of such recombinant phages, which can be used as a fractionated rice genomic DNA library.

(3) Selection of a Promoter Gene from the Rice Genomic DNA Library

The rice genomic DNA library which was obtained as the recombinant phages in the above (2), was screened for selection of such recombinant phages which carried a DNA sequence corresponding to the promoter gene for the expression of the rice ASA gene, by utilizing the labeled probe DNA as prepared in Example 1(5).

For the screening, the recombinant phages were fixed on nylon membranes and then hybridized with the labeled probe DNA in the same manner as in Example 1(5). The phages carrying the desired DNA sequence were thus selected. As a result, three phage plaques, which were judged to carry the promoter gene for the ASA gene, were selected and isolated from one hundred thousand phage plaques. From each of the isolated three recombinant phages, λ DNA was isolated in the same manner as in Example 1(6).

The thus isolated three kinds of phage DNAs (5 μl each) were separately digested with 10 units of the restriction enzyme EcoRI. The resultant digestion mixtures were analyzed. By this analysis, the RcoRI fragments as derived from the above three phage DNAs were recognized to have the same nucleotide sequence.

(4) Cloning of Genomic DNA Carrying the DNA Sequence Corresponding to the Promoter Gene for the Rice ASA Gene The 6.2 kb DNA fragments, which were obtained by the EcoRI digestion of the three phage DNAs as the DNA fragments assumably carrying the DNA sequence corresponding to the rice ASA promotor gene as described above, were inserted into the EcoRI-cleavage site of the plasmid vector pBluescript II SK(+) by using a DNA ligation kit, thereby to construct recombinant plasmid vectors. The obtained recombinant plasmid vectors were introduced into *E. coli* XLI-Blue MRF' for transformation. The resulting *E. coli* transformant was named *Escherichia coli* XLI-Blue MRF' (Os-asa#7), and it was deposited with the National Institute of Bioscience and Human-Technology on Aug. 18, 1997 with accession number FERM P–16387 and also on Aug. 7, 1998 under the Budapest Treaty with accession number FERM BP–6452.

The above construction of the recombinant plasmid vectors and introduction thereof into *E. coli* were carried out in the same manner as in Example 1(6).

Plasmids were isolated and purified from the *E. coli* carrying the introduced recombinant plasmid vectors by using a plasmid purification kit (QIAfilter Plasmid Midi Kit, QIAGEN). Thereby, three kinds of plasmid DNAs (50 μg, 50 μl) were obtained.

DNAs of about 1.5 kb having the EcoRI- and BamHI-cleaved ends, which were carried by the above three kinds of plasmids as cloned from the isolated respective recombinant phages, were then subjected to nucleotide sequence analysis in the following manner.

(5) Sequence Analysis of Cloned DNAs

When treatment of the recombinant plasmids which are the above three kinds of cloned DNAs was made with a commercially available nucleotide sequence determination kit, the entire nucleotide sequence of their DNA fragments can be determined. Also the DNA sequence corresponding to the promoter gene for the rice ASA gene as carried by said DNA fragments can be identified.

Said determination of the nucleotide sequence was carried out in the same manner as in Example 1(7).

Such nucleotide sequence analysis revealed that the recombinant plasmids which are the above three kinds of the cloned DNAs were all identical to each other.

The thus obtained promoter DNA for the ASA gene was recognized to have the nucleotide sequence shown in SEQ ID NO: 7 of Sequence Listing. The nucleotide sequence of SEQ ID NO: 7 determined here embraces an intron, and its protein-encoding region thereof completely agrees with the cDNA clone. Among the nucleotide sequences as determined for the resulting recombinant plasmid DNAs, the nucleotide sequence of the DNA sequence comprising the promoter region of the ASA gene and the exon and intron regions thereof is shown in SEQ ID NO: 3 of Sequence Listing.

SEQ ID NO: 3 also shows a partial amino acid sequence of the protein which is the α-subunit of the first isozyme of rice ASA. Further, SEQ ID NO: 4 shows the amino acid sequence of the amino acid-encoding region of the nucleotide sequence shown in SEQ ID NO: 3. SEQ ID NO: 5 shows the amino acid sequence of exon-1 in the DNA of SEQ ID NO: 3. SEQ ID NO: 6 shows a partial sequence of exon-2 in the DNA of SEQ ID NO: 3.

(6) Promoter Activity Assay Test (i) Construction of a Recombinant Vector for Activity Test In order to examine the promoter DNA obtained above (SEQ ID NO: 7) for its promoter activity, the DNA [the EcoRI-BamHI fragment obtained in the above (4)] was inserted upstream of the β-glucuronidase (GUS) gene of the plant cell transformation vector pBI101 (Clontech), thereby to construct a transformation vector, pGUS#3.

Figure 3:
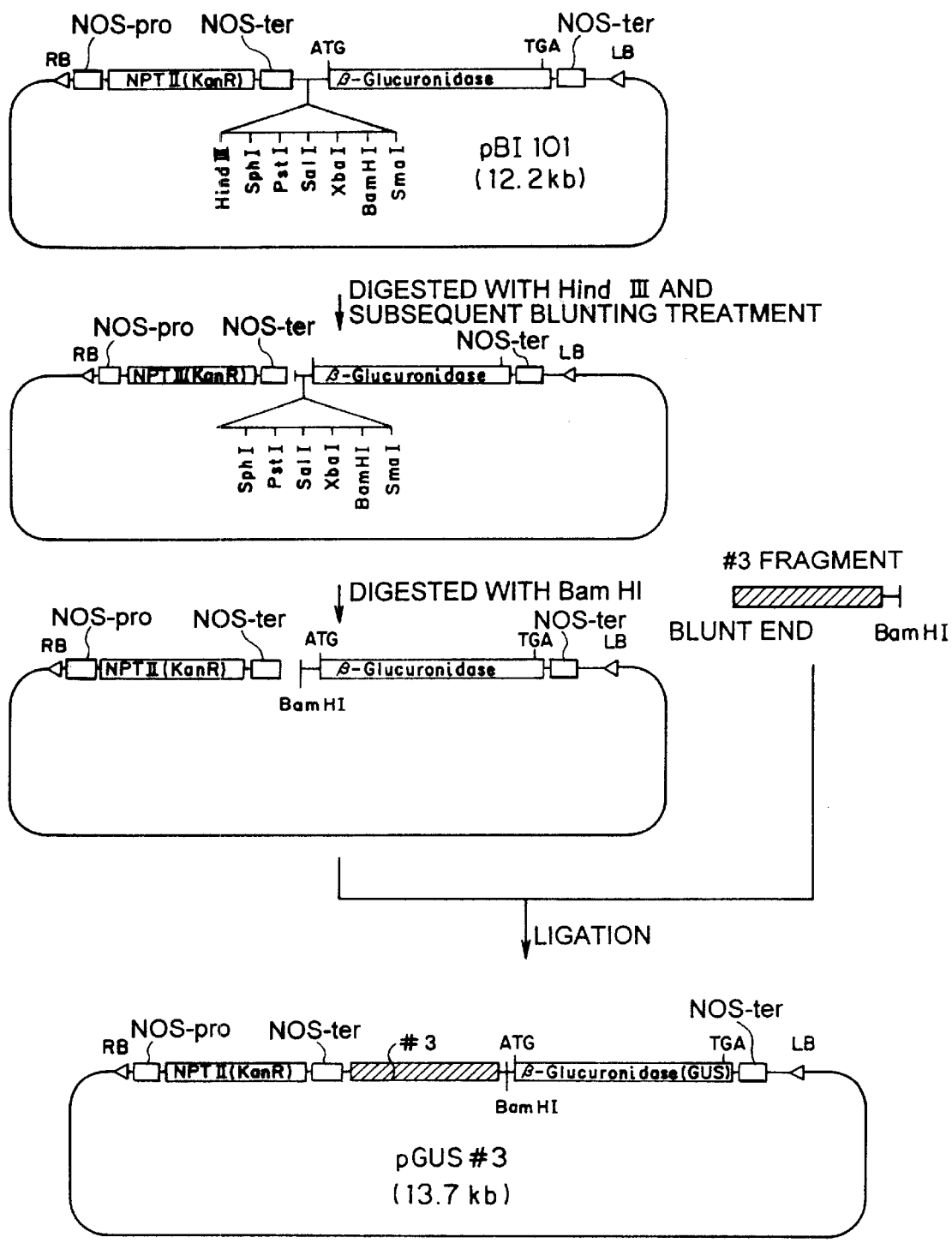
FIG. 3 is a schematic illustration of the process employed in Example 5(6) wherein there was constructed from the vector pBI101, the recombinant vector pGUS#3 which is a recombinant vector carrying the promoter sequence for rice ASA of the sixteenth aspect of the present invention as an exogenous gene to be used for transforming rice callus cells in the activity test of said promoter sequence, and in which vector GUS#3 is legated the DNA fragment #3 carrying the promoter sequence of the present invention and having the nucleotide sequence shown in SEQ ID NO: 3.

That is, the transformation vector was constructed in the following manner. First, 10 μg of pBI101 plasmid DNA (Clontech) (which is a 12.2 kb plasmid vector containing the NOS terminator for the GUS gene and a kanamycin resistance gene) was digested with 10 units of the restriction enzyme HindIII in M buffer. DNA was precipitated from the digestion mixture, centrifuged and dried. After being dissolved in 10 μl of sterilized water, the DNA was treated with a DNA blunting kit (Takara Shuzo Co., Ltd.), to blunt the cleaved ends, followed by purification using a DNA purification kit (Gene Clean II Kit, Bio 101). The purified DNA was dissolved in 10 μl of sterilized water and then digested with 10 units of the restriction enzyme BamHI in K buffer. DNA was precipitated from the digestion mixture, centrifuged and dried. This procedure gave such a 12.2 kb vector fragment which has one blunt end and one BamHI-cleaved end (see the left part of FIG. 3 in the attached drawings).

Separately, 10 μg of the above plasmid vector containing the promoter DNA fragment for the rice ASA gene was digested with 10 units of the restriction enzyme EcoRI in H buffer. DNA was precipitated from the digestion mixture, centrifuged and dried. After being dissolved in 10 μl of sterilized water, the DNA was treated with a DNA blunting kit (Takara Shuzo Co., Ltd.), to blunt the cleaved ends, followed by purification using a DNA purification kit (Gene Clean II Kit, Bio 101). The purified DNA was dissolved in 10 μl of sterilized water and then digested with 10 units of the restriction enzyme BamHI in K buffer. The digestion mixture was subjected to agarose electrophoresis, and a band at about 1.5 kb was cut out of the gel, followed by purification using a DNA purification kit. The purified DNA was dissolved in 10 μl of sterilized water. This procedure gave such a 1.5 kb promoter DNA fragment which has one blunt end and one BamHI-cleaved end (see the right part of FIG. 3).

The above aqueous solution of the plasmid vector fragment (5 μl) and the above aqueous solution of the promoter DNA fragment (5 μl) were mixed together. The resulting mixture was subjected to DNA ligation reaction by using a DNA ligation kit.

This reaction gave such a circular recombinant vector, in which the blunt end-BamHI fragment as derived from the above promoter DNA for the rice ASA gene was ligated with the blunt end-BamHI vector fragment as derived from the plasmid vector pBI101. This circular recombinant vector was named as pGUS#3 (see the lower part of FIG. 3).

The vector pGUS#3 had a size of 13.7 kb and was found to carry the GUS gene downstream of the promoter DNA for the rice ASA gene, and the NOS terminator downstream of the GUS gene, as well as and the kanamycin resistance gene.

(ii) Introduction of the Recombinant Vector for Activity Test into Rice Callus Cells The recombinant vector pGUS#3 obtained as above was introduced into rice callus cells in the same manner as in Example 3(6).

Rice callus cells so transformed with the recombinant vector pGUS#3 were thus obtained.

(iii) Measurement of GUS Activity

The rice callus cells, which were transformed with the recombinant vector pGUS#3 obtained as above, were cultured at 28° C. for 3 days, and about 0.5 g of the cultured callus cells was put in a mortar. After addition of 500 μl of an extraction buffer [50 mM NaPO$_4$ (pH 7), 10 mM EDTA, 0.1% Triton X100, 0.1% Sarkosyl, 10 mM β-mercaptoethanol], the callus cells were disrupted. The disrupted cell suspension was transferred to a 1.5-ml tube. The cell suspension was centrifuged at 17000×g for 20 minutes, and 10 μl of the supernatant was transferred to another tube, followed by admixing with 100 μl of a 1 mM solution of 4-methylumbelliferyl glucuronide (4-MUG), which is a substrate. The resulting admixture was subjected to reaction at 37° C. for 3 hours. To this resulting reaction mixture was added 1.8 ml of a 3% sodium hydrogen carbonate solution, followed by mixing. The resulting mixture was subjected to a fluorescense absorption measurement by a fluorospectrophotometer (F2000, Hitachi, Ltd.) (excitation at 365 nm, emission at 455 nm), to determine the GUS activity.

The results of the determination of the GUS activity are shown in Table 3. The numerical values of Table 3 indicate the amount of 4-methylumbelliferone (4-MU) which was formed by the action of the GUS enzyme in one hour per 1 gram of protein as extracted from the callus. A control experiment was carried out with using such callus in which pBI101 vector carrying no promoter had been used for the introduction of the gene.

TABLE 3

|  | GUS Activity |
| --- | --- |
| Test | 348 n mol |
| Control | 0 n mol |

As evidenced by the expression of the GUS activity shown in the above, the promoter region which was identified on the basis of the result of the above nucleotide sequence analysis is able to function as a promoter.

INDUSTRIAL APPLICABILITY

The present invention provides genes for encoding the α-subunits of the two isoenzymes of rice ASA, which genes are capable of increasing the content of tryptophan, an essential amino acid, in a plant, when the genes are introduced into the plant either alone or in combination with other genes and thus are useful for breeding plants of high nutritive value. The DNAs of the α-subunits of the two isoenzymes of rice ASA which are provided by the present invention, are also useful for selecting the transformed cells or transformed plants when said DNAs are introduced into plant cells. The present invention also provides such a promoter DNA for the rice ASA gene, which can be used as a promoter in expressing a useful exogenous gene in a plant and thus is useful for producing the transformed plants.

What is claimed is:

1. An isolated DNA encoding a protein having the amino acid sequence shown in SEQ ID NO: 13; said protein having the enzymatic activity of an α-subunit of a first isozyme of anthranilate synthase, said isozyme being insensitive to the feedback inhibition by tryptophan or a tryptophan analogue.

2. The isolated DNA according to claim 1; wherein said DNA has the nucleotide sequence shown in SEQ ID NO: 12.

3. A transformed plant comprising a transformed plant cell comprising a recombinant vector comprising the DNA of claim 1 that encodes a protein having the enzymatic activity of an α-subunit of a first isozyme of rice anthranilate synthase, said isozyme being insensitive to feedback inhibition by tryptophan or a tryptophan analogue; said DNA being expressed in said plant.

4. A recombinant vector which comprises a DNA sequence encoding a protein having the amino acid sequence shown in SEQ ID No. 13, wherein said DNA sequence is expressible in a host cell.

5. A recombinant vector which comprises an inserted DNA fragment comprising the nucleotide sequence shown in SEQ ID NO: 12, wherein said DNA sequence is expressible in a host cell.

6. An *Escherichia coli* as transformed with a recombinant vector which comprises an inserted DNA fragment comprising a DNA sequence encoding a protein having the amino acid sequence shown in SEQ ID No. 13, wherein said DNA sequence is expressible in said *Escherichia coli*.

7. An *Escherichia coli* transformed with a recombinant vector which comprises an inserted DNA fragment comprising the DNA sequence having the nucleotide sequence shown in SEQ ID NO: 12, wherein said DNA sequence is expressible in said *Escherichia coli*.

8. A method of increasing the tryptophan content of a plant, said method comprising:

introducing into a plant callus cell, a recombinant vector where said recombinant vector comprises the DNA of claim 1 encoding a protein having the enzymatic activity of an α-subunit of a first isozyme of anthranilate synthase, said isozyme insensitive to the feedback inhibition by tryptophan, wherein said DNA is expressed in the plant cell, and regenerating a plant from said plant callus cell.

9. A method of selecting a transformed plant cell that is resistant to tryptophan or a tryptophan analogue, said method comprising:

introducing a recombinant vector into plant cells wherein said recombinant vector comprises the DNA of claim 1 encoding a protein having the enzymatic activity of an α-subunit of a first isozyme of anthranilate synthase, said isozyme being insensitive to feedback inhibition by tryptophan or a tryptophan analogue and wherein said recombinant vector further comprises an antibiotic resistance gene; and selecting a plant cell that exhibit resistance to an inhibitory amount of tryptophan or a tryptophan analogue, as compared to a nontransformed plant cell.

10. A method of producing a transformed plant having an increased tryptophan content, said method comprising introducing a recombinant vector into plant cells wherein said recombinant vector comprises the DNA of claim 1 encoding a protein having the enzymatic activity of an α-subunit of a first isozyme of anthranilate synthase, said isozyme being insensitive to feedback inhibition by tryptophan and wherein said recombinant vector further comprises an antibiotic resistance gene;

selecting cells that exhibit resistance to an inhibitory amount of tryptophan or a tryptophan analogue, as compared to a nontransformed plant cell; and regenerating a plant from the selected cells.

\* \* \* \* \*